(12) United States Patent
Nuccio et al.

(10) Patent No.: US 11,814,632 B2
(45) Date of Patent: Nov. 14, 2023

(54) MODIFIED EXCISABLE MON87701 SOYBEAN TRANSGENIC INSECT RESISTANCE LOCUS

(71) Applicant: INARI AGRICULTURE TECHNOLOGY, INC., Cambridge, MA (US)

(72) Inventors: Michael Lee Nuccio, Salem, NH (US); Michael Andreas Kock, Rheinfelden (DE); Joshua L. Price, Cambridge, MA (US)

(73) Assignee: INARI AGRICULTURE TECHNOLOGY, INC., Cambridge, MA (US)

( * ) Notice: Subject to any disclaimer, the term of this patent is extended or adjusted under 35 U.S.C. 154(b) by 0 days.

(21) Appl. No.: 18/058,156

(22) Filed: Nov. 22, 2022

(65) Prior Publication Data

US 2023/0147013 A1    May 11, 2023

Related U.S. Application Data

(63) Continuation of application No. PCT/US2021/043933, filed on Jul. 30, 2021.

(60) Provisional application No. 63/203,137, filed on Jul. 9, 2021, provisional application No. 63/202,569, filed on Jun. 16, 2021, provisional application No. 63/201,030, filed on Apr. 9, 2021, provisional application No. 63/201,029, filed on Apr. 9, 2021, provisional application No. 63/199,951, filed on Feb. 4, 2021, provisional application No. 63/199,949, filed on Feb. 4, 2021, provisional application No. 63/199,930, filed on Feb. 3, 2021, provisional application No. 63/059,813, filed on Jul. 31, 2020, provisional application No. 63/059,860, filed on Jul. 31, 2020, provisional application No. 63/059,916, filed on Jul. 31, 2020, provisional application No. 63/059,963, filed on Jul. 31, 2020.

(51) Int. Cl.

| | |
|---|---|
| *C12N 15/82* | (2006.01) |
| *C12Q 1/6895* | (2018.01) |
| *C12N 9/22* | (2006.01) |
| *C12N 15/11* | (2006.01) |
| *A01H 6/54* | (2018.01) |
| *A01H 5/10* | (2018.01) |
| *C12Q 1/6834* | (2018.01) |
| *A01H 6/46* | (2018.01) |
| *C07K 14/415* | (2006.01) |

(52) U.S. Cl.
CPC .......... *C12N 15/8201* (2013.01); *A01H 5/10* (2013.01); *A01H 6/4684* (2018.05); *A01H 6/542* (2018.05); *C07K 14/415* (2013.01); *C12N 9/22* (2013.01); *C12N 15/11* (2013.01); *C12N 15/8213* (2013.01); *C12N 15/8286* (2013.01); *C12Q 1/6834* (2013.01); *C12Q 1/6895* (2013.01); *C12N 2310/20* (2017.05); *C12N 2800/80* (2013.01); *C12Q 2600/13* (2013.01); *C12Q 2600/156* (2013.01); *C12Q 2600/158* (2013.01)

(58) Field of Classification Search
None
See application file for complete search history.

(56) References Cited

U.S. PATENT DOCUMENTS

| | | |
|---|---|---|
| 7,632,985 B2 | 12/2009 | Malven et al. |
| 7,956,246 B2 | 6/2011 | Bing et al. |
| 8,049,071 B2 | 11/2011 | Gao et al. |
| 8,232,456 B2 | 7/2012 | Long et al. |
| 8,450,561 B2 | 5/2013 | Beazley et al. |
| 8,455,198 B2 * | 6/2013 | Gao .................. C12N 15/8286 435/6.12 |
| 8,455,720 B2 | 6/2013 | Long et al. |
| 8,466,346 B2 | 6/2013 | DeFramond et al. |
| 8,575,434 B2 | 11/2013 | Diehn et al. |
| 9,540,655 B2 | 1/2017 | Cui et al. |
| 11,041,172 B2 | 6/2021 | Cermak |
| 11,214,811 B1 | 1/2022 | Nuccio et al. |
| 11,242,534 B1 | 2/2022 | Nuccio et al. |
| 11,359,210 B2 | 6/2022 | Price et al. |
| 2010/0162428 A1 | 6/2010 | Brown et al. |
| 2011/0191899 A1 | 8/2011 | Ainley et al. |
| 2014/0196169 A1 | 7/2014 | D'Halluin et al. |
| 2015/0059010 A1 | 2/2015 | Cigan et al. |
| 2015/0082478 A1 | 3/2015 | Cigan et al. |

(Continued)

FOREIGN PATENT DOCUMENTS

| | | |
|---|---|---|
| WO | 2022026375 A1 | 2/2022 |
| WO | 2022026379 A1 | 2/2022 |

(Continued)

OTHER PUBLICATIONS

Baliga et al., "Investigation of direct repeats, spacers and proteins associated with clustered regularly interspaced short palindromic repeat (CRISPR) system of Vibrio parahaemolyticus," Molecular Genetics and Genomics, Oct. 24, 2018, vol. 294, pp. 253-262.

(Continued)

*Primary Examiner* — Matthew R Keogh
(74) *Attorney, Agent, or Firm* — McKee, Voorhees & Sease, PLC

(57) ABSTRACT

Transgenic INIR20 soybean plants comprising modifications of the MON87701 soybean locus which provide for facile excision of the modified MON87701 transgenic locus or portions thereof, methods of making such plants, and use of such plants to facilitate breeding are disclosed.

13 Claims, 7 Drawing Sheets

Specification includes a Sequence Listing.

(56) References Cited

U.S. PATENT DOCUMENTS

| | | |
|---|---|---|
| 2016/0333363 A1 | 11/2016 | Srivastava |
| 2017/0166912 A1 | 6/2017 | Brower-Toland et al. |
| 2018/0057878 A1 | 3/2018 | Bing et al. |
| 2018/0163218 A1 | 6/2018 | Corbin et al. |
| 2019/0112614 A1 | 4/2019 | Russell et al. |
| 2019/0136249 A1 | 5/2019 | Sakai et al. |
| 2019/0352655 A1 | 11/2019 | Niu et al. |
| 2020/0157554 A1 | 5/2020 | Cigan et al. |
| 2020/0405649 A1 | 12/2020 | Wang et al. |
| 2022/0030806 A1 | 2/2022 | Price et al. |
| 2022/0030822 A1 | 2/2022 | Nuccio et al. |
| 2022/0033833 A1 | 2/2022 | Gilbertson et al. |
| 2022/0033836 A1 | 2/2022 | Price et al. |
| 2022/0098602 A1 | 3/2022 | Nuccio et al. |
| 2022/0154194 A1 | 5/2022 | Nuccio et al. |
| 2022/0251584 A1 | 8/2022 | Nuccio et al. |
| 2022/0364105 A1 | 11/2022 | Price et al. |
| 2023/0077473 A1 | 3/2023 | Price et al. |
| 2023/0078387 A1 | 3/2023 | Kock et al. |
| 2023/0083144 A1 | 3/2023 | Nuccio et al. |
| 2023/0087222 A1 | 3/2023 | Kock et al. |
| 2023/0147013 A1 | 5/2023 | Nuccio et al. |

FOREIGN PATENT DOCUMENTS

| | | |
|---|---|---|
| WO | 2022026390 A1 | 2/2022 |
| WO | 2022026395 A2 | 2/2022 |
| WO | 2022026403 A2 | 2/2022 |
| WO | 2022026801 A1 | 2/2022 |

OTHER PUBLICATIONS

Biopesticides Registration Action Document, "Bacillus thuringiensis Vip3Aa20 Insecticidal Protein and the Genetic Material Necessary for Its Production (via Elements of Vector pNOV1300) in Event MIR162 Maize (OECD Unique Identifier: SYN-IR162-4)," PC Code: 006599, U.S. Environmental Protection Agency, Office of Pesticide Programs, Biopesticides and Pollution Prevention Division, Mar. 2009, 175 pages.

Bissler, J.J., "Triplex DNA and human disease," Frontiers in Bioscience, May 1, 2007, vol. 12, pp. 4536-4546.

Bortesi et al., "The CRISPR/Cas9 system for plant genome editing and beyond," Biotechnology Advances, Dec. 20, 2014, vol. 33, Issue 1, pp. 41-52.

Charpentier et al., "Biogenesis pathways of RNA guides in archaeal and bacterial CRISPR-Cas adaptive immunity," FEMS Microbiology Reviews, May 19, 2015, vol. 39, Issue 3, pp. 428-441.

Cho et al., "Nonallelic homologous recombination events responsible for copy number variation within an RNA silencing locus," Plant Direct, vol. 3, Aug. 27, 2019, 16 pages.

Du et al., "Construction of Marker-Free Genetically Modified Maize Using a Heat-Inducible Auto-Excision Vector," Genes, May 17, 2019, vol. 10, No. 374, 17 pages.

Du et al., "Infection of Embryonic Callus with Agrobacterium Enables High-Speed Transformation of Maize," International Journal of Molecular Sciences, Jan. 11, 2019, vol. 20, No. 279, 15 pages.

Finnigan et al., "mCAL: A New Approach for Versatile Multiplex Action of Cas9 Using One sgRNA and Loci Flanked by a Programmed Target Sequence," G3: Genes, Genomes, Genetics, Jul. 1, 2016, vol. 6, pp. 2147-2156.

Gurusaran et al., "RepEx: Repeat extractor for biological sequences," Genomics, Jul. 21, 2013, vol. 102, pp. 403-408.

International Searching Authority in connection with PCT/US21/43897 filed Jul. 30, 2021, "Invitation to Pay Additional Fees And, Where Applicable, Protest Fee," dated Oct. 27, 2021, 3 pages.

International Searching Authority in connection with PCT/US21/43935 filed Jul. 30, 2021, "Invitation to Pay Additional Fees And, Where Applicable, Protest Fee," dated Oct. 26, 2021, 3 pages.

International Searching Authority in connection with PCT/US21/43945 filed Jul. 30, 2021, "Invitation to Pay Additional Fees And, Where Applicable, Protest Fee," dated Oct. 27, 2021, 3 pages.

Kim et al., "CRISPR/Cpf1-mediated DNA-free plant genome editing," Nature Communications, Feb. 16, 2017, vol. 8, Article No. 14406, 7 pages.

Li et al., "Expanding the Scope of CRISPR/Cpf1-Mediated Genome Editing in Rice," Molecular Plant, Jul. 2, 2018, vol. 11, No. 7, pp. 995-998, 14 pages.

Luo et al., "Improperly Terminated, Unpolyadenylated mRNA of Sense Transgenes is Targeted by RDR6-Mediated RNA Silencing in Arabidopsis," The Plant Cell, Mar. 23, 2007, vol. 19, pp. 943-958.

Malzahn et al., "Application of CRISPR-Cas1 2a temperature sensitivity for improved genome editing in rice, maize, and Arabidopsis," BMC Biology, Jan. 31, 2019, vol. 17, No. 9, 14 pages.

Non-Final Office Action in U.S. Appl. No. 17/248,936, dated Mar. 25, 2021, 25 pages.

Non-Final Office Action in U.S. Appl. No. 17/249,640, dated Jun. 29, 2021, 10 pages.

Non-Final Office Action in U.S. Appl. No. 17/302,110, dated Jun. 29, 2021, 22 pages.

Non-Final Office Action in U.S. Appl. No. 17/302,121, dated Jul. 8, 2021, 10 pages.

Non-Final Office Action in U.S. Appl. No. 17/302,739, dated Aug. 3, 2021, 24 pages.

Notice of Allowance in U.S. Appl. No. 17/249,640, dated Sep. 22, 2021, 7 pages.

Que et al., "Maize transformation technology development for commercial event generation," Frontiers in Plant Science, Aug. 5, 2014, vol. 5, Article No. 379, 19 pages.

Srivastava et al., "Gene Stacking by recombinases," Plant Biotechnology Journal, Feb. 2016, vol. 14, pp. 471-482.

Srivastava, et al., "Dual-targeting by CRISPR/Cas9 for precise excision of transgenes from rice genome," Plant Cell Tissue and Organ Culture, Jan. 20, 2017, vol. 129, pp. 153-160.

Ward et al., "Petition for Determination of Nonregulated Status for Insect-Resistant MIR162 Maize," Syngenta Biotechnology, Inc., Aug. 31, 2007, 271 pages.

"What is a CRISPR-Cas system?," CRISPR-CAS++, Universite Paris-Saclay, accessed Nov. 2, 2021. Retrieved from the Internet <URL:https://crisprcas.i2bc.paris-saclay.fr/Home/About>, 2 pages.

Xing et al., "Revealing frequent alternative polyadenylation and widespread low-level transcription read-through of novel plant transcription terminators," Plant Biotechnology Journal, Sep. 2010, vol. 8, pp. 772-782.

Young et al., "CRISPR-Cas9 Editing in Maize: Systematic Evaluation of Off-target Activity and Its Relevance in Crop Improvement," Scientific Reports, Apr. 30, 2019, vol. 9, No. 6729, 11 pages.

Danilo et al., "The DFR locus: A smart landing pad for targeted transgene insertion in tomato," PLoS One, Dec. 6, 2018, vol. 13, No. 12, 14 pages.

Eaglesham et al., "New DNA-Editing Approaches: Methods, Applications & Policy for Agriculture," North American Agricultural Biotechnology Council Report, NABC Report 26, 2014, 255 pages.

Gleditzsch et al., "PAM identification by CRISPR-Cas effector complexes: diversified mechanisms and structures," RNA Biology, 2019, vol. 16, No. 4, pp. 504-517.

Rudgers et al., "EXZACTTM Precision Technology: Scientific and Regulatory Advancements in Plant-Genome Editing with ZFNs," North American Biotechnology Council, 2014, pp. 113-124.

Shi et al., "ARGOS8 variants generated by CRISPR-Cas9 improve maize grain yield under field drought stress conditions," Plant Biotechnology Journal, 2017, vol. 15, pp. 207-216.

Yau et al., "Less is more: strategies to remove marker genes from transgenic plants," BMC Biotechnology, 2013, vol. 13, No. 36, 23 pages.

Office Action in U.S. Appl. No. 18/058,081, dated Apr. 11, 2023, 27 pages.

Office Action in U.S. Appl. No. 18/058,161, dated Apr. 11, 2023, 23 pages.

Begemann et al., "Precise insertion and guided editing of higher plant genomes using Cpf1 CRISP nucleases," Scientific Reports, Sep. 14, 2017, vol. 7, No. 11606, pp. 1-6.

Begemann et al., Supplementary Data—Precise insertion and guided editing of higher plant genomes using Cpf1 CRISPR nucleases, Scientific Reports, Sep. 14, 2017, vol. 7, No. 11606, 18 pages.

(56) References Cited

OTHER PUBLICATIONS

International Search Report in PCT/US2021/043161, dated Jan. 5, 2022, 6 pages.
International Search Report in PCT/US2021/043170, dated Jan. 5, 2022, 6 pages.
International Search Report in PCT/US2021/043187, dated Jan. 6, 2022, 6 pages.
International Search Report in PCT/US2021/043192, dated Jan. 27, 2022, 7 pages.
International Search Report in PCT/US2021/043207, dated Jan. 27, 2022, 6 pages.
International Search Report in PCT/US2021/043851, dated Dec. 30, 2021, 6 pages.
International Search Report in PCT/US2021/043919, dated Jan. 20, 2022, 8 pages.
International Search Report in PCT/US2021/043933, dated Dec. 30, 2021, 6 pages.
International Search Report in PCT/US2021/044198, dated Jan. 19, 2022, 6 pages.
Non-Final Office Action in U.S. Appl. No. 17/302,110, dated May 24, 2023, 27 pages.
Non-Final Office Action in U.S. Appl. No. 17/650,031, dated May 26, 2023, 11 pages.
Non-Final Office Action in U.S. Appl. No. 17/680,647, dated Jun. 23, 2022, 11 pages.
Non-Final Office Action in U.S. Appl. No. 18/057,860, dated Jun. 1, 2023, 49 pages.
Non-Final Office Action in U.S. Appl. No. 18/057,867, dated Jun. 7, 2023, 17 pages.
Non-Final Office Action in U.S. Appl. No. 18/058,144, dated Jun. 7, 2023, 49 pages.
Non-Final Office Action in U.S. Appl. No. 18/058,156, dated May 19, 2023, 24 pages.
Non-Final Office Action in U.S. Appl. No. 18/162,134, dated Jun. 21, 2023, 28 pages.
Zhang et al., "Off-target Effects in CRISPR/Cas9-mediated Genome Engineering," Molecular Therapy—Nucleic Acids, Nov. 17, 2015, vol. 4, pp. 1-8.
Zhong et al., "Plant Genome Editing Using FnCpf1 and LbCpf1 Nucleases at Redefined and Altered PAM Sites," Molecular Plant, Jul. 2018, vol. 11, No. 7, pp. 999-1002.
Zhong et al., "Supplementary Data—Plant Genome Editing Using FnCpf1 and LbCpf1 Nucleases at Redefined and Altered PAM Sites," Molecular Plant, Jul. 2018, vol. 11, No. 7, 36 pages.

\* cited by examiner

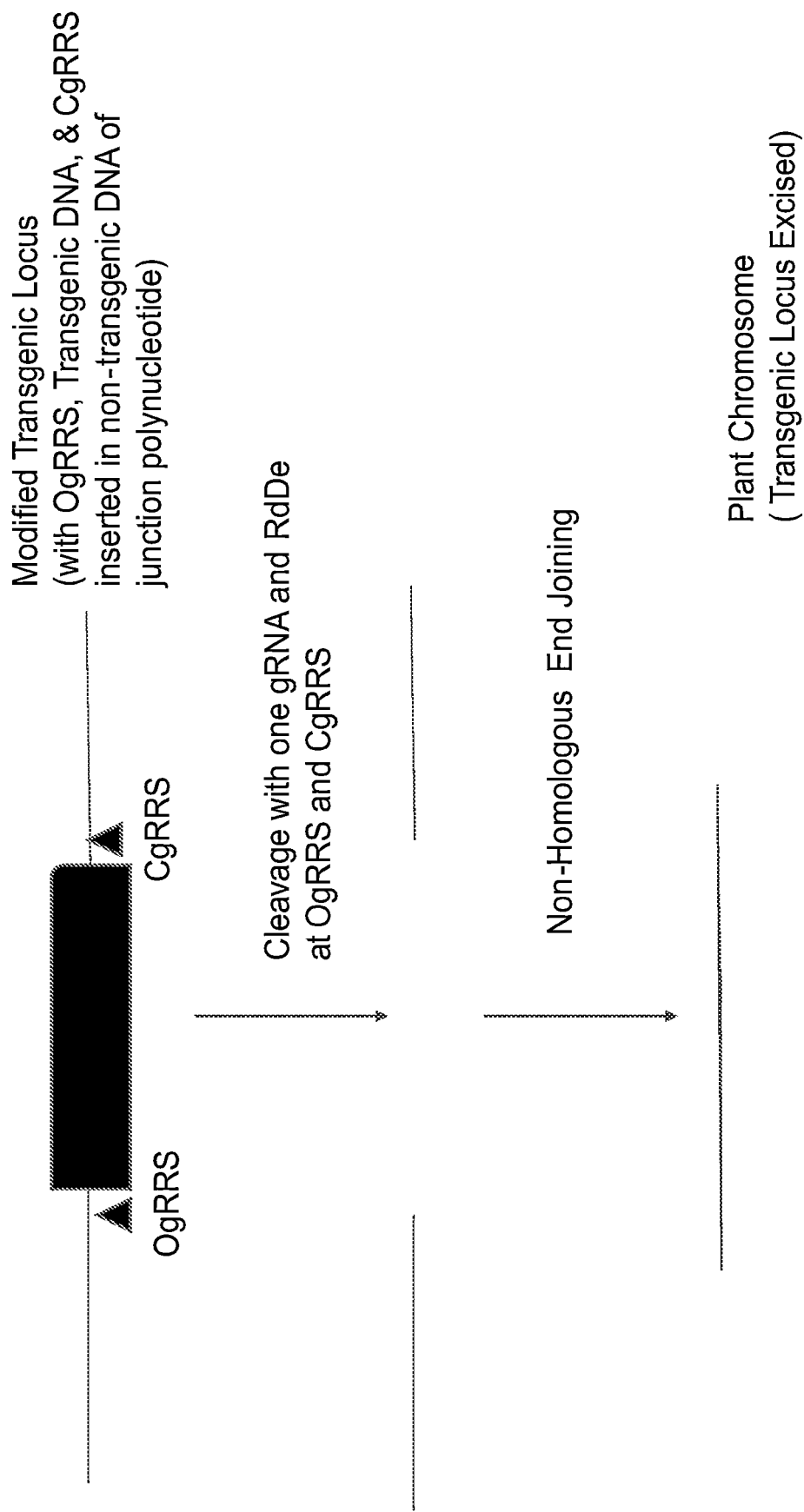

SEQUENCE LISTING

```
Sequence total quantity: 21
SEQ ID NO: 1              moltype = DNA   length = 14416
FEATURE                   Location/Qualifiers
source                    1..14416
                          mol_type = other DNA
                          organism = synthetic construct
SEQUENCE: 1
gggaaaatcc ctcttccata ttaagaacat aaaaatcaac aggaaaaata agttcaccaa   60
cccgaaccag cacatcctct atgaaacctg cggggtaagc agcacttcta ttttccaaat  120
gaatcaccac atctgtagat tgcaaaggtc caagagataa agaattgaaa atggacagag  180
gggtgacact aactgatgct cctagatcta gcattgtatt atcaaattta ctgttcccaa  240
taatgcaagg tatacagaaa gtacctgggt ccttacattt ctcaggaatg taaggaacaa  300
atttacctat caatgctgac acatttctgc ccatgctaat cctttcattg cctttgagct  360
tccttttgtg ggtgacaaac tccttagaa acttgacaca tcttggaatc tgcttgatgg  420
catctagcag aggtatgttc acctctactt tcctgaaggt ctccaagatc tcctttctg   480
cttcttccat ttttttttgtt tggaattgct caaggttgga atggaagagg gataagaggc  540
tgcggtaagt cagaattact agaagaaggt ccacctgcat gaaaattttt gttaggaagc  600
tttctctttt gtgcaactat ctcatcctct ttttcaggtg tagaatgaag cttgacaggt  660
tcaggtgcgg gtgctgctac tggtggaggt acttgaattt ggttgtcaga cctcaaggtg  720
atgacactca catttttcgg attttgcaca gtttgtgaag gcaatttgtc agaattttgg  780
gaatgagctt ggttcaactg agtagccatc cgccccatct gatttgtcag actctgaatg  840
aaggctcttg tctcttgctg aaattgcata ttctggatgg tcatttgcct cactaactct  900
tctaaggaag gttaaggagg agtctcagtt gcttgttgtc tttgttgtga ctgttgttgt  960
tgttgctgct gtattggagg aggaacatat ggtttgcttg gaccagcaac attctggaaa 1020
ggagggacag actgttgttg ttgtgaagga cttgcccatc tcatatttgg atgatttctc 1080
caacctggat tgtatctgtt gcttggaaga tcataattat tttgctattg ttggttttgc 1140
tgttgagggg gtctattata aatgtttgca gcataagctt caggttgttc attgactcca 1200
gattactgca aagaaggaca aagatctgta tggtgatctg cagaagaaca tataccacag 1260
actcttgtaa caggtgcaaa tttctgattc atggcaagct gagttactag gttgaccaag 1320
gcatcaagtt ttccctcaag ctttttattt tcagtagata aagatgaatc tgtggccacc 1380
tcatcgactc ctctaaggac aatagcatca tttcttgcac tgaattgttg ggagttgaaa 1440
gccttcttct caatcaaatt cctagcctca gcaggggtca tatcacgaag agctccacca 1500
ctgcagcat caatcatact cctctccatg ttgctaagtc cctcatagaa atattgaaga 1560
aggagttgct cagaaatctg gtggtgagga cagcttgcac acaatttctt gaatctttct 1620
cagtactcat acaagctctc tccactaagt tgcctgatgc ctgaaatttc ttttctgatg 1680
gcagtggtcc tagatgcagg gaagaatttc tccaagaaca ccctcttaag gtcatcccag 1740
ctgaaaatgg acctgggagc aaggtagtag agccaatctt ttgtcactac ctccagaaa  1800
tgaggaaaag ccttagaaa gatatgatct tcttggacat cagggggctt catggtgaa   1860
caaacaatat ggaactcctt aagatgctta tgaggatctt cacctagaag accatgaaac 1920
ttgggtagca aatgtattag tccagtcttg agaacatatg gaacaccctc atcaggatat 1980
tgaatgcaca agttttcata agtgaaatca ggtgcagcca tctcccctaag agtcctctca 2040
cgaggtggag gtttagccat gttctcagta tgaaaattag tagttgaatg ctcaaaatca 2100
gaatattcag aatcaccaga aacaaatac tcagaatgct caaaatgctc aaaatgcaca  2160
taatgattag gatgcacact atgcctaact aatctatgaa aggttctatc tatttcagga 2220
```

```
tcgaagggtt ataaatcacc tagattgccc ctagtcatgc actatatgta gcaaataatg    2280
tgttctcaaa caagcaccaa gggagggtta aaactacaac tatagtcaaa tgatatccaa    2340
atgagttgaa attttgtgag cagcacccta aaatcatgaa aagatagcac aaaaaatttc    2400
aaacgaaaat tcaaagtcta actatgaaaa ctacttaaga aaagtttaga aaaataggac    2460
aataatactt gaaaaataaa aaaaaacata gtaaacagct gattttttcga gtttgggaga    2520
ctccaaccgg ctaaaacggg ttgccacaat atgagaaatt ttttttctacc ccaaatgcca    2580
caatatgaga aagttttgct aaaatctagt tcccaaaatt tttgtctctc tcaaattcaa    2640
ccacaccaag tgctcctagt attttttcaca caaaaaatca gccaaaaata caactctaa     2700
ctatcaaaac aaaaacagct aattaaattg caaaatcagt cgctaattcc tagtcactaa    2760
tcactgttca cagcaaaaca ccaactgaat cagtcgctaa acagtcgcta aacaggagac    2820
gcaactgaaa tgcaaaacag aatgctacac aaaacaaaac aactaaacac tattatgaac    2880
ctttggccca ctgctcccg acaacggcgc caaatttgat cgaggtcgta cccgaatcaa     2940
ataaacatta aaaatgcagt atctaggaag tgatcctagg tcatctccca acgagcaatg    3000
gtcaaccaat gttcataata gatagtgata aaacaataac gaattggggg gggggggtat    3060
ttgtttttgt aatttaaaca acaagcaaat tttaattaga aaataacaga attaaaacat    3120
gttatttccc cttgattcat aagcaagtct cttatcctag gttaggagga tttatcccta    3180
accagttcaa ccacttaatc caaccctaaa ttaaattact aagcgaaaat taacataagg    3240
ttgtctttat atgattaagc aacacataca ccaattaatc atgaacaaaa tcgatcatta    3300
agcatcaaca taaattaagc gcaaagataa ttaatcaagc actaagcatg catggattag    3360
tagcaacaaa tacagagtaa ttggtggaga tgaaaaactg atcaatattc aatagtaata    3420
acaaaacctc aaagagagtt gtgcttgatt ctcaagagaa acaacgctg gagacttagc      3480
cttccattaa tcagtagaaa acgaaattgt agaaaacgaa ttttattcta tgtgaacaat    3540
gtgcatgaac agtaataaaa actggaattg caaaacccta aaattattct tctctccaaa    3600
aaaactccct aaactaaaac cctggtgcta ttatataggt cctcagcccc aaagcttaca    3660
aatctatttt cagtccaaac ccataaacga aataaaataa aatctggaca agataagata    3720
agattggatg aaataaaatc tggacgaaat aaaatctgga taagataaga tttgataaaa    3780
taaaattgtc tgctcttttc aagtccaagc ccaattccgg attcaagccc aattttttat    3840
aattcttctg aaattaaatt aaaaatacga aattagtcaa gtaggcccaa atgataaaac    3900
tgcataatta atttgacaat taaggctaat cagtaattaa aatagtgaca aaaagggtta    3960
agaaatagga gaataatgac acatcaccca tatggggagc aattctaaaa tgcatttgag    4020
ttctttaacc tgagacacag tgcagtagag tctccaagga ttcattgtgc cttttatttt    4080
atatgatggg gtcactacat tggccttgtc aaagaaactg aatttggggg attaaagaaa    4140
cacaaaataa aaacaaatga aactagttaa tagaaatgtt gcctattgct tcttggaaaa    4200
agtccaacca tttgtgattt ggataaaatt catattaccc acttgtagct tgttcaatca    4260
aacactagat ttggataaaa tctcactcct agatataacct caagggataa tatgaccaac    4320
attagtcatt tttagaaagt aaagtggaca aatttgagat ttcattcctt aatgacatta    4380
taaacatgta ttttttccat gacccttttt caatgtaagt acaatttatc ccttagttta    4440
gatactctat atatgcatgt tacgtagttg atgaaaacat acctaagttg ttgtgtatgg    4500
ttaagtttgc gactacctct gatatcaaac tcctcatctc caatctcata caaaagatac    4560
ttgtcacttg gtacctgaac cttgtcagtt tgcagttgtg agtttcttct gaagccacac    4620
gcttgtatag taaccagaag ccaggaggga gtccctaag gctctaactc gtattttccg      4680
tggaagtaca ttttttttct taaagaaaac agagatagtt taccaatgat aatatttctt    4740
tagccaaata ggaccatcat agaaaacaaa actcttcttc taagtattta atgcaactac    4800
atattaggg tgcgtttgat tcgctaaaaa ataagggtct agacaacaca aaaatatttt      4860
tccaacgttt gattttaaaa atggctgaga gacaatacaa aataaagaat gatgaactgg    4920
acaaaaacct aaaaacttgt aactcactga atctcataca acttttttgtt cagtgtctaa    4980
aaaaagtaaa aatacaatat tattcctatt tttttacttg attatctcac accttctttc    5040
tactcatttg tttcacttca cctctccagt gggcaccttg gtttgtcggc gagagtcgta    5100
tggactttg ttgtttcctt tttgctcatt atttctttct tttcattgtt aatttattca     5160
aatgttccca tcatcatctt actccttctt gttatgtttt ttttcttttgg ccaactccaa    5220
cgaggccgtg ccgcgaccac catcatcacg accttatggc ggcctcacgc cgcaaggccc    5280
tgcacccagt ggcatcaggg gtcatgcctc cttcttaaag gtgtctctct tttgttatgt    5340
cgtcaaagtg ttgctaattc acctagaatt tttcaatgaa tccctttact tgtgggttag    5400
tctaggtcgc tctgcccggt tccaacccta gcccaaaaaa aatgaaatg ggtaggaaag      5460
gcgggcctag tttgaattaa aataaatcat gctaagatat tgataactgc tatgtatagg    5520
tatattttgg gattaaatta tataggaatt agtaattttc ctctcttatt tcttcctttt    5580
tgttcaaata attggaattc taacatcatt taagttttta tgtagaaaat attaaaagtt    5640
gatgaattta tgatacttag tgaataatta gagtagaaaa ataaagtaaa gcccaaaaaa    5700
gaaaattggt gatatgaaga tacatgctta gcatgcccca ggcacgctta gtgtgtgtgt    5760
caaacactga tagtttaaac tgaaggcggg aaacgacaat ctgatcccca tcaagcttga    5820
tatcgaattc ctgcagcccg ggggatccac tagttctaga gcggccgcgt taactgcagg    5880
tcgacggatc cccgggtacc gagctcgaat tcaaatttat tatgtgtttt ttttccgtgg    5940
tcgagattgt gtattattct ttagttatta caagactttt agctaaaatt tgaaagaatt    6000
tacttttaaga aaatcttaac atctgagata atttcagcaa tagattatat ttttcattac    6060
tctagcagta tttttttgcaga tcaatcgcaa catatatgt tgttagaaaa aatgcactat    6120
atatatatat attattttt caattaaaag tgcatgatat ataatatata tatatatata    6180
tatgtgtgtg tgtatatggt caaagaaatt cttatcaaaa tatacacgaa cacatatatt    6240
tgcaaaaatc aaagtattac actaaacaat gagttggtgc atggccaaaa caatatgta    6300
gattaaaaat tccagcctcc aaaaaaaaaat ccaagtgttg taaagcatta tatatatata    6360
gtagatccca aatttttgta caattccaca ctgatcgaat ttttaaagtt gaatatctga    6420
cgtaggattt tttaatgtc ttacctgacc atttactaat aacattcata cgttttcatt     6480
tgaaatatcc tctataatta tattgaattt ggcacataat aagaaaccta attggtgatt    6540
tatttttacta gtaaatttct ggtgatgggc tttctactag aaagctctcg gaaaatcttg    6600
gaccaaatcc atattccatg acttcgattg ttaaccctat tgttttttcac aaacatacta    6660
tcaatatcat tgcaacgaa aaggtacaag taaaacatt atcccgatg ggaagtgatg        6720
taggaggttg ggaagacagg cccagaaaga gatttatctg acttgttttg tgtatagttt    6780
tcaatgttca taaaggaaga tggagacttg agaagttttt tttggacttt gtttagcttt    6840
gttgggcgtt ttttttttg atcaataact ttgttgggct tatgatttgt aatatttcg      6900
tggactcttt agtttattta gacgtgctaa ctttgttggg cttatgactt gttgtaacat    6960
```

```
attgtaacag atgacttgat gtgcgactaa tctttacaca ttaaacatag ttctgttttt      7020
tgaaagttct tatttcatt tttatttgaa tgttatatat ttttctatat ttataattct      7080
agtaaaaggc aaattttgct tttaaatgaa aaaaatatat attccacagt ttcacctaat      7140
cttatgcatt tagcagtaca aattcaaaaa tttcccattt ttattcatga atcataccat      7200
tatatattaa ctaaatccaa ggtaaaaaaa aggtatgaaa gctctatgt aagtaaaata      7260
taaattcccc ataaggaaag ggccaagtcc accaggcaag taaaatgagc aagcaccact      7320
ccaccatcac acaatttcac tcatagataa cgataagatt catggaatta tcttccacgt      7380
ggcattattc cagcggttca agccgataag ggtctcaaca cctctcctta ggcctttgtg      7440
gccgttacca agtaaaatta acctcacaca tatccacact caaaatccaa cggtgtagat      7500
cctagtccac ttgaatctca tgtatcctag accctccgat cactccaaag cttgttctca      7560
ttgttgttat cattatatat agatgaccaa agcactagac caaacctcag tcacacaaag      7620
agtaaagaag aacaatggct tcctctatgc tctcttccgc tactatggtt gcctctccgg      7680
ctcaggccac tatggtcgct cctttcaacg gacttaagtc ctccgctgcc ttcccagcca      7740
cccgcaaggc taacaacgac attacttcca tcacaagcaa cggcggaaga gttaactgca      7800
tgcaggtgtg gcctccgatt ggaaagaaga agtttgagac tctctcttac cttcctgacc      7860
ttaccgattc cggtggtcgc gtcaactgca tgcaggccat ggacaacaac ccaaacatca      7920
acgaatgcat tccatacaac tgcttgagta acccagaagt tgaagtactt ggtggagaac      7980
gcattgaaac cggttcacac cccatcgaca tctccttgtc cttgacacag tttctgctca      8040
gcgagttcgt gccaggtgct gggttcgttc tcggactagt tgacatcatc tggggtatct      8100
ttggtccatc tcaatgggat gcattcctgg tgcaaattga gcagttgatc aaccagagga      8160
tcgaagagtt cgccaggaac caggccatct ctaggttgga aggattgagc aatctctacc      8220
aaatctatgc agagagcttc agagagtggg aagccgatct tactaaccca gctctccgcg      8280
aggaaatgcg tattcaattc aacgacatga acagcgcctt gaccacagct atcccattgt      8340
tcgcagtcca gaactaccaa gttcctctct tgtccgtgta cgttcaagca gctaatcttc      8400
acctcagcgt gcttcgagac gttagcgtgt ttgggcaaag gtgggggattc gatgctgcaa      8460
ccatcaaatag ccgttacaac gaccttacta ggctgattgg aaaatacacc gaccacgctg      8520
ttcgttggta caacactggc ttggagcgtg tctggggtcc tgattctaga gattggatta      8580
gatacaacca gttcaggaga gaattgaccc tcacagtttt ggacattgtg tctctcttcc      8640
cgaactatga ctccagaacc tacccatcc gtacagtgtc ccaacttacc agagaaatct      8700
atactaaccc agttcttgag aacttcgacg gtagcttcc tggttctgcc caaggtatcg      8760
aaggctccat caggagccca cacttgatgg acatcttgaa cagcataact atctacaccg      8820
atgctcacag aggagagtat tactggtctg gacaccagat catggcctct ccagttggat      8880
tcagcgggcc cgagtttacc tttcctctct atggaactat gggaaacgcc gctccacaac      8940
aacgtatcgt tgctcaacta ggtcagggtg tctacagaac cttgtcttcc accttgtaca      9000
gaagaccctt caatatcggt atcaacaacc agcaactttc cgttcttgac ggaacagagt      9060
tcgcctatgg aacctcttct aacttgccat ccgctgttta cagaaagagc ggaaccgttg      9120
attccttgga cgaaatccca ccacagaaca acaatgtgcc acccaggcaa ggattctccc      9180
acaggttgag ccacgtgtcc atgttccgtt ccggattgcag caacagttcc gtgagcatca      9240
tcagagctcc tatgttctct tggatacatc gtagtgctga gttcaacaac atcatcgcat      9300
ccgatagtat tactcaaatc cctgcagtga agggaaactt tctcttcaac ggttctgtca      9360
tttcaggacc aggattcact ggtggagacc tcgttagact caacagcagt ggaaataaca      9420
ttcagaatag agggtatatt gaagttccaa ttcacttccc atccacatct accagatata      9480
gagttcgtgt gaggtatgct tctgtgaccc ctattcacct caacgttaat tggggtaatt      9540
catccatctt ctccaataca gttccagcta cagctacctc cttggataat ctccaatcca      9600
gcgatttcgg ttactttgaa agtgccaatg cttttatcac ttcactcggt aacatcgtgg      9660
gtgttagaaa ctttagtggg actgcaggag tgattatcga cagattcgag ttcattccag      9720
ttactgcaac actcgaggct gagtacaacc ttgagagagc ccagaaggct gtgaacgccc      9780
tctttacctc caccaatcag cttggcttga aaactaacgt tactgactat cacattgacc      9840
aagtgtccaa cttggtcacc taccttagcg atgagttctg cctcgacgag aagcgtgaac      9900
tctccgagaa agttaaacac gccaagcgtc tcagcgacga gaggaatctc ttgcaagact      9960
ccaacttcaa agacatcaac aggcagccag aacgtggttg gggtggaagc accgggatca     10020
ccatccaagg aggcgacgat gtgttcaagg agaactacgt caccctctcc ggaactttcg     10080
acgagtgcta ccctacctac ttgtaccaga agatcgatga gtccaaactc aaaagccttca     10140
ccaggtatca acttagaggc tacatcgaag acagccaaga ccttgaaatc tactcgatca     10200
ggtacaatgc caagcacgag accgtgaatg tcccaggtac tggttccctc tggccactgt     10260
ctgcccaatc tcccattggg aagtgtggag agcctaacag atgcgctcca caccttgagt     10320
ggaatcctga cttggactgc tcctgcaggg atggcgagaa gtgtgcccac cattctcatc     10380
acttctcctt ggacatcgat gtgggatgta ctgacctgaa tgaggacctc ggagtctggg     10440
tcatcttcaa gatcaagacc caagacgac acgcaagact tggcaacctt gagtttctcg     10500
aagagaaacc attggtcggt gaagctctcg ctcgtgtgga gagcagag aagaagtgga     10560
gggacaaacg tgagaaactc gaatgggaaa ctaacatcgt ttacaaggag gccaaagagt     10620
ccgtggatgc tttgttcgtg aactcccaat atgatcagtt gcaagccgac accaacatcg     10680
ccatgatcca cgccgcagac aaacgtgtgc acagcattcg tgaggcttac ttgcctgagt     10740
tgtccgtgat ccctcggtgtg aacgctgcca tcttcgagga acttgaggga cgtatcttta     10800
ccgcattctc cttgtacgat gccagaaacg tcatcaagaa cggtgacttc aacaatggcc     10860
tcagctgctg gaatgtgaaa ggtcatgtgg acgtggagga acagaacaat cagcgttccg     10920
tcctggttgt gcctgagtgg gaagctgaag tgtcccaaga ggttagagtc tgtccaggta     10980
gaggctacat tctccgtgtg accgcttaca aggagggata cggtgagggt tgcgtgacca     11040
tccacgagat cgagaacaac accgacgagc ttaagttctc caactgcgtc gaggaagaaa     11100
tctatcccaa caacaccgtt acttgcaacg actacactgt gaatcaggaa gagtacggag     11160
gtgcctacac tagccgtaac agaggttaca acgaagctcc ttccgttcct gctgactatg     11220
cctccgtgta cgaggagaaa tcctacacag atggcagacg tgaaccct tgcgagttca     11280
acagaggtta cagggactaa acaccactcc cagttggcta tgttaccaag gagcttgagt     11340
actttgaa gaccgacaaa gtgtggatcg agatcgtgga aaccggggga accttcatcg     11400
tggacagcgt ggagcttctc ttgatggagg aataatgaga tccgtccctt tgtcttcaat     11460
tttgagggct tttactgaa taagtatgta gtactaaaat gtatgctgta atagctcata     11520
gtgagcgagg aaagtatcgg gctatttaac tatgacttga gctccatcta tgaataaata     11580
aatcagcata tgatgctttt gttttgtgta cttcaactgt ctgcttagct aatttgatat     11640
ggttggcact tggcacgtat aaatatgctg aagtaattta ctctgaagct aaattaacta     11700
```

```
gattagatga gtgtattata tacaaaaggc attaaatcag atacatctta gacaaattgt   11760
cacggtctac cagaaaagaa attgcatttg ttttttgggtc tttcagactg acaagatcga   11820
tctgaagtct aaacaattct aagaggtatc atgtagcaat gtcctgccac aatattgaat   11880
tgacctgcag cccgggcggc cgcatcgatc gtgaagtttc tcatctaagc ccccatttgg   11940
acgtgaatgt agacacgtcg aaataaagat ttccgaatta gaataatttg tttattgctt   12000
tcgcctataa atacgacgga tcgtaatttg tcgttttatc aaaatgtact ttcattttat   12060
aataacgctg cggacatcta cattttgaa ttgaaaaaa attggtaatt actcttttctt    12120
tttctccata ttgaccatca tactcattgc tgatccatgt agatttcccg gacatgaagc   12180
catcaaaaag taggactaat ttaggaaagc aagctaattc aagaaagtga aggcacgctt   12240
agtgtgagac acgtgttgag cgcgattact gccactcact aaccacacaa gtgcactcag   12300
tgcgaaggtt gcttaaaaat taagttgatt cgcacttata aaagaaggat agagatgaag   12360
gaaaaaacac agaaaataca attccttata gaagacaaag gctagaagaa gcaaacgcaa   12420
acattagaag tcattccttc cctcaattcc ctttttcaat ttcccctttt actaaatatt   12480
ctcctcttgc aattataaag cctcctatga caatgacaag ctaaactctc ctttgttggg   12540
aacttatcag tcaactgctc ttaatataat ttctcttcct atctattatg aatattcact   12600
acaagaaata tgcccatttg ccagggattt ttgacaggga cattacccc tggcaaattt    12660
cccagggact aagccaagga aaccctggc aaaatgacat ttgagaaggc tgggaccact    12720
tacatttaca caggggtttg tccctcgcaa aaatacaaaa gccttggcaa aaaaaagagc   12780
gggaaatgaa ttttaaaaca gcatgttgtt ttcacacagc caaacacacg ggtatgccct   12840
cgttttctgt aaagctgacg gaatcttccc ataagtcaac acgacatgac catgcactgc   12900
aaaaagctgt gcggcccaga cgtgacaggg gtgttacccc tcggaaatgg cttgcagccc   12960
ctggcaaaaa ggaatccctg cttccttagc tacaccgttc tgctcatata gctgaagcta   13020
ggaggttagc ctttgactct gttgttttgc gaggggcatt ccgtgagtta ttccctgggt   13080
ttttttacac tatatagcca aaccgcgtgt ttatcctcat gctcagtgtt gtgttttga    13140
aacttagaaa aattttcggt ttccatttcc atcctcacca gttcatttc agtccattat    13200
cattcagttc atacacttgt tctataattt ggtaacactc ttttcactta ttatattttt   13260
ctgttttat ttgttactac ttattaacat aaatattttt tattgtatca gtgtccaaat    13320
ttgcctcctc ctgctgctcc ttgctctctg aattgttct cttaagcttc aacaagttag    13380
taatttttct acttataatt ttagatatat gatgtttata tatgtgatgt tataatttg    13440
catgatctgt caaagaaaat atgatgtttc tactttgcat gatgtgttata atatatgatg   13500
tttatatata tttcgaattt tgttgttaat aaaactgttt aattagaaac tgtataattt    13560
ttttgtttaa taaactgtt taattttgca tgatctgttt aataaaactg tttatataaa    13620
actgtttata tataatatat gatgttaaca ttttaaaac tgtttataaa acagtttagt    13680
tagaaaaaat gttaaaacta gagaaaaaaa tgtataataa aactgtgtca gtacagcagc   13740
gcgtcagaaa agtgtgcaga tgcgtcagtg agaagacagg ggctaagaca gggattttga   13800
cagggaattt tgccagggat tttgccaggg tcagccccct gtttttttgc caggggtgaa   13860
atccctggca aactgatttg cgatgggcgt ttttcccagg gattcagccc ctggcaaaat   13920
ccctggcaaa cgtccatttc ccagggcttt ttgttcttt cccagggaat ccgcccctgg    13980
caaacgagct tgttttcttgt agtgattact tttgcattag ttttttcctg atttaatttt   14040
attgtttatg gcttgattac ccatttgcat tataagtttt aggggtagcg ttgaaaagtg   14100
ttattctcta atagaactgg aaaagagtat ttaaataact tcatcactag ggatacattg   14160
attttattta gcttattata tatctctatt attaatgtaa tttaactatt ttatctctgc   14220
aaagtgattt gggagagaag atagataagt tagactcttt cactcgaggc tgagtacaac   14280
cttgagagag cccagaaggc tgtgaacgcc ctctttacct ccaccaatca gcttggcttg   14340
aaaactaacg ttactgacta tcacattgac caagtgtcca acttggtcac ctaccttagc   14400
gatgagttct gaaggg                                                   14416

SEQ ID NO: 2          moltype = DNA   length = 14409
FEATURE               Location/Qualifiers
source                1..14409
                      mol_type = other DNA
                      organism = synthetic construct
SEQUENCE: 2
gggaaaatcc ctcttccata ttaagaacat aaaaatcaac aggaaaaata agttcaccaa   60
cccgaaccag cacatcctct atgaaacctg cggggtaacg agcacttcta tttttccaaat  120
gaatcaccac atctgtagat tgcaaaggtc caagagataa agaattgaaa atggacagag   180
gggtgacact aactgatgct cctagatcta gcattgtatt atcaaattta ctgttcccaa   240
taatgcaagg tatacagaaa gtacctgggt ccttacattt tcaggaatg taaggaacaa    300
atttacctat caatgctgac acatttctgc ccatgctaat cctttcattg cctttgagct   360
tccttttgtg ggtgcacaac tcctttagaa acttgacaca tcttggaatc tgcttgatgg   420
catctagcag aggtatgttc acctctactt tcctgaaggt ctccaagatc tccttttctg   480
cttcttccat ttttttttgtt tggaattgct caaggttgga atggaagagg ataagaggc   540
tgcggtaagt cagaattact agaagaaggt ccacctgcat gaaaatttt gttaggaagc    600
tttctctttt gtgcaactat ctcatcctct ttttcaggtg tagaatgaag ctgacagtt    660
tcaggtgcgg gtgctgctac tggtggaggt acttgaattt ggttgtcaga cctcaaggtg   720
atgacactca cattttcgg attttgcaca gtttgtgaag caatttgtc agaatttgg     780
gaatgagctt ggttcaactg agtagccatc cgccccatct gatttgtcag actctgaatg   840
aaggctcttg tctcttgctg aaattgcata ttctggatgg tcatttgcct cactaactct   900
tctaaggaag gttaaggagg agtctcagtt gcttgttgtc tttgttgtga ctgtcttgttgt   960
tgttgctgct gtattggagg aggaacatat ggtttgcttg gaccagcaac attctggaaa   1020
ggagggacag actgttgttg ttgtgaagga cttcccatcc tcatatttgg atgatttctc   1080
caacctggat tgtatctgtt gcttggaaga tcataattat tttgctattg ttggttttgc   1140
tgttgagggg gtctattata aatgtttgca gcataagctt caggttgttc attgactcca   1200
gattactgca aagaaggaca aagatctgta tggtgatcg aagaagaaca tataccacag   1260
actcttgtaa caggtgcaaa tttctgattc atggcaagct gagttactag gttgaccaag   1320
gcatcaagtt ttccctcaag ctttttattt tcagtagata aagatgaatc tgtgccacc    1380
tcatcgactc ctcaaggac aatagcatca tttcttgcac tgaattgttg ggagttgaa    1440
gccttcttct caatcaaatt cctagcctca gcaggggtca tatcacgaag agctccacca   1500
ctggcagcat caatcatact cctctccatg ttgctaagtc cctcatagaa atattgaaga   1560
```

```
aggagttgct cagaaatctg gtggtgagga cagcttgcac acaatttctt gaatctttct    1620
cagtactcat acaagctctc tccactaagt tgcctgatgc ctgaaatttc ttttctgatg    1680
gcagtggtcc tagatgcagg gaagaatttc tccaagaaca ccctcttaag gtcatcccag    1740
ctgaaaatgg acctgggagc aaggtagtag agccaatctt ttgtcactac ctccagagaa    1800
tgaggaaaag cctttagaaa gatatgatct tcttggacat caggggggct catggtggaa    1860
caaacaatat ggaactcctt aagatgctta tgaggatctt cacctagaag accatgaaac    1920
ttgggtagca aatgtattag tccagtcttg agaacatatg gaaccccctc atcaggatat    1980
tgaatgcaca agttttcata agtgaaatca ggtgcagcca tctccctaag agtcctctca    2040
cgaggtggag gtttagccat gttctcagta tgaaaattag tagttgaatg ctcaaaatca    2100
gaatattcag aatcaccaga aacaaaatac tcagaatgct caaaatgctc aaaatgcaca    2160
taatgattag gatgcacact atgcctaact aatctatgaa aggttctatc tatttcagga    2220
tcgaagggtt ataaatcacc tagattgccc ctagtcatgc actatatgta gcaaataatg    2280
tgttctcaaa caagcaccaa gggagggtta aaactacaac tatagtcaaa tgatatccaa    2340
atgagttgaa attttgtgag cagcacccta aaatcatgaa aagtagcac aaaaaatttc    2400
aaacgaaaat tcaaagtcta actatgaaaa ctacttaaga aaagtttaga aaaataggac    2460
aataatactt gaaaataaaa aaaaacata gtaaacagct gattttttcga gtttgggaga    2520
ctccaaccgg ctaaaacggg ttgccacaat atgagaaatt ttttttctacc ccaaatgcca    2580
caatatgaga aagtttttgct aaaatctagt tcccaaaatt tttgtctctc tcaaattcaa    2640
ccacaccaag tgctcctagt attttttcaca caaaaaatca gccaaaaata caactctaa    2700
ctatcaaaac aaaaacagct aattaaattg caaatcagt cgctaattcc tagtcactaa    2760
tcactgttca cagcaaaaca ccaactgaat cagtcgctaa acagtcgcta aacaggagac    2820
gcaactgaaa tgcaaaacag aatgctacac aaaacaaaac aactaaacac tattatgaac    2880
ctttggccca ctgctccccg acaacggcgc caaatttgat cgaggtcgta cccgaatcaa    2940
ataaacatta aaaatgcagt atctaggaag tgatcctagg tcatctccca acgagcaatg    3000
gtcaaccaat gttcataata gatagtgata aaacaataac gaattggggg gggggggtat    3060
ttgtttttgt aatttaaaca aacaagcaaat tttaattaga aaataacaga attaaaacat    3120
gttatttccc cttgattcat aagcaagtct cttatcctag gttaggagga tttatcccta    3180
accagttcaa ccacttaatc caaccctaaa ttaaattact aagcgaaaat taacataagg    3240
ttgtcttat atgattaagc aacacataca ccaattaatc atgaacaaaa tcgatcatta    3300
agcatcaaca taattaagc gcaaagataa ttaatcaagc actaagcatg catggattag    3360
tagcaacaaa tacagagtaa ttggtggaga tgaaaaactg atcaatattc aatagtaata    3420
acaaaacctc aaagagagtt gtgcttgatt ctcaagagaa aacaacgctg gagacttagc    3480
cttccattaa tcagtagaaa acgaaattgt agaaaacgaa ttttattcta tgtgaacaat    3540
gtgcatgaac agtaataaaa actggaattg caaaacccta aaattattct tctctctcaaa    3600
aaaactcccct aaactaaaac cctggtgcta ttatataggt cctcagcccc aaagcttaca    3660
aatctatttt cagtccaaac ccataaacga aataaaataa aatctggaca agataagata    3720
agattggatg aaataaaatc tggacgaaat aaaatctgga taagataaga tttgataaaa    3780
taaaattgtc tgctctttc aagtccaagc ccaattccgg attcaagccc aatttttat    3840
aattcttctg aaattaaatt aaaaatacga aattagtcaa gtaggcccaa atgataaaa    3900
tgcataatta atttgacaat taaggctaat cagtaattaa aatagtgaca aaaagggtta    3960
agaaatagga gaataatgac acatcaccca tatggggagc aattctaaaa tgcatttgag    4020
ttctttaacc tgagacacag tgcagtagag tctccaagga ttcattgtgc cttttatttt    4080
atatgatggg gtcactacat tggccttgtc aaagaaactg aatttggggg attaaagaaa    4140
cacaaaataa aaacaaatga aactagttaa tagaaatgtt gcctattgct tcttggaaaa    4200
agtccaacca tttgtgattt ggataaaatt catattaccc acttgtagct tgttcaatca    4260
aacactagat ttgataaaaa tctcactcct agatatacct caagggataa tatgaccaac    4320
attagtcatt tttagaaagt aaagtggaca aatttgagat ttcattcctt aatgacatta    4380
taaacatgta ttttttccat gaccccttttt caatgtaagt acaatttatc ccttagttta    4440
gatactctat atatgcatgt tacgtagttg atgaaaacat acctaagttg ttgtgtatgg    4500
ttaagtttgc gactacctct gatatcaaac tcctcatctc caatctcata caaagatac    4560
ttgtcacttg gtacctgaac cttgtcagtt tgcagtttgta agtttcttct gaagccacac    4620
gcttgtatag taaccagaag ccaggaggga gtcctctaag gctctaactc gtattttccg    4680
tggaagtaca ttttttttct taaagaaaac agagatagtt taccaatgat aatatttctt    4740
tagccaaata ggaccatcat agaaaacaaa actcttcttc taagtattta atgcaactac    4800
atatttaggg tgcgtttgat tcgctaaaaa ataagggtct agacaacaca aaaatatttt    4860
tccaacgttt gatttttaaaa atggctgaga gacaatacaa aataaagaat gatgaactga    4920
acaaaaacct aaaaacttgt aactcactga atctcataca acttttttgtt cagtgtctaa    4980
aaaaagtaaa aatacaatat tattcctatt ttttactttg attatctcac accttctttc    5040
tactcatttg tttcacttca cctctccagt gggcaccttg gtttgtcggc gagagtcgta    5100
tggacttttg ttgtttcctt tttgctcatt atttctttct tttcattgtt aatttattca    5160
aatgttccca tcatcatctt actccttctt gttatgtttt tttctttttgg ccaactccaa    5220
cgaggccgtg ccgcgaccac catcatcacg acctatgc ggcctcacgc cgcaaggccc    5280
tgcacccagt ggcatcaggg gtcatgcctc cttcttaaag gtgtctctct tttgttatgt    5340
cgtcaaagtg ttgctaattc acctagaatt tttcaatgaa tcccttttact tgtgggttag    5400
tctaggtcgc tctgcccggt tccacccta gcccaaaaaa aaatgaaatg ggtaggaaag    5460
gcgggcctag tttgaattaa aataaatcat gctaagatat tgataactgc tatgtatagg    5520
tatatttttgg gattaaatta tataggaatt agtaattttt ctctcttatt tcttcctttt    5580
tgttcaaata attggaattc taacatcatt taagttttta tgtagaaaat attaaaagtt    5640
gatgaattta tgatacttag tgaataatta gagtagaaaa ataagtaaa gcccaaaaaa    5700
gaaaattggt gatatgaaga tacatgctta gcatgcccca ggcacgctta ggtcaaacac    5760
tgatagttta aactgaaggc gggaaacgac atctgatcc ccatcaagct tgatatcgaa    5820
ttcctgcagc ccgggggatc cactagtttct agagcggccg cgttaactgc aggtcgacgg    5880
atcccccggg accgagctcg aattcaaatt tattatgtgt ttttttttccg tggtcgagat    5940
tgtgtattat tctttagtta ttacaagact tttagctaaa attttgaaaga atttacttta    6000
agaaaatctt aacatctgag ataatttcag caatagatta tattttttcat tactctagca    6060
gtattttttgc agatcaatcg caacatatat ggttgttaga aaaaatgcac tatatatata    6120
tatattattt tttcaattaa aagtgcatga tatataaaat atatatatat atatatgtgt    6180
gtgtgtatat ggtcaaagaa attcttatac aaatatacac gaacacatat atttgacaaa    6240
atcaaagtat tacactaaac aatgagttgg tgcatggcca aaacaaatat gtagattaaa    6300
```

```
aattccagcc tccaaaaaaa aatccaagtg ttgtaaagca ttatatatat atagtagatc   6360
ccaaatttt  gtacaattcc acactgatcg aattttaaa  gttgaatatc tgacgtagga   6420
tttttttaat gtcttacctg accatttact aataacattc atacgttttc atttgaaata   6480
tcctctataa ttatattgaa tttggcacat aataagaaac ctaattggtg atttatttta   6540
ctagtaaatt tctggtgatg ggctttctac tagaaagctc tcggaaaatc ttggaccaaa   6600
tccatattcc atgacttcga ttgttaaccc tattagtttt cacaaacata ctatcaatat   6660
cattgcaacg gaaaaggtac aagtaaaaca ttcaatccga tagggaagtg atgtaggagg   6720
ttgggaagac aggcccagaa agagatttat ctgacttgtt ttgtgtatag ttttcaatgt   6780
tcataaagga agatggagac ttgagaagtt ttttttggac tttgttttagc tttgttgggc   6840
gtttttttt  ttgatcaata acttttgttgg gctatgatt tgtaatattt tcgtggactc   6900
tttagtttat ttagacgtgc taactttgtt gggcttatga cttgttgtaa catattgtaa   6960
cagatgactt gatgtgcgac taatctttac acattaaaca tagttctgtt ttttgaaagt   7020
tcttattttc attttttattt gaatgttata tatttttcta tatttataat tctagtaaaa   7080
ggcaaatttt gcttttaaat gaaaaaaata tatattccac agtttcacct aatcttatgc   7140
atttagcagt acaaattcaa aaatttccca ttttttattca tgaatcatac cattatatat   7200
taactaaatc caaggtaaaa aaaggtatg  aaagctctat agtaagtaaa atataaattc   7260
cccataagga aagggccaag tccaccaggc aagtaaaatg agcaagcacc actccaccat   7320
cacacaattt cactcataga taacgataag attcatggaa ttatcttcca cgtggcatta   7380
ttccagcggt tcaagccgat aagggtctca acacctctcc ttaggccttt gtggccgtta   7440
ccaagtaaaa ttaacctcac acatatccac actcaaaatc caacggtgta gatcctagtc   7500
cacttgaatc tcatgtatcc tagaccctcc gatcactcca aagcttgttc tcattgttgt   7560
tatcattata tatagatgac caaagcacta gaccaaacct cagtcacaca aagagtaaag   7620
aagaacaatg gcttcctcta tgctctcttc cgctactatg gttgcctctc cggctcaggc   7680
cactatggtc gctcctttca acggacttaa gtcctccgct gccttcccag ccacccgcaa   7740
ggctaacaac gacattactt ccatcacaag caacggcgga agagttaact gcatgcaggt   7800
gtggcctccg attggaaaga agaagtttga gactctctct taccttcctg accttaccga   7860
ttccggtggt cgcgtcaact gcatgcaggc catggacaac aacccaaaca tcaacgaatg   7920
cattccatac aactgcttga gtaacccaga agttgaagta cttggtggag aacgcattga   7980
aaccggttac actcccatcg acatctcctt gtccttgaca cagtttctgc tcagcgagtt   8040
cgtgccaggt gctgggttcg ttctcggact agttgacatc atctggggta tctttggtcc   8100
atctcaatgg gatgcattcc tggtgcaaat tgagcagttg atcaaccaga ggatcgaaga   8160
gttcgccagg aaccaggcca tctctaggtt ggaaggattg agcaatctct accaaatcta   8220
tgcagagagc ttcagagagt gggaagccga tcctactaac ccagctctcc gcgaggaaat   8280
gcgtattcaa ttcaacgaca tgaacagcgc cttgaccaca gctatcccat tgttcgcagt   8340
ccagaactac caagttcctc tcttgtccgt gtacgttcaa gcagctaatc ttcacctcga   8400
cgtgcttcga gacgttagcg tgtttgggca aagtggggga ttcgatgctg caaccatcaa   8460
tagccgttac aacgaccta  ctaggctgat tggaaactac accgaccacg ctgttcgttg   8520
gtacaacact ggcttggagc gtgtctgggg tcctgattct agagattgga ttagatacaa   8580
ccagttcagg agagaattga ccctcacagt tttggacatt gtgtctctct tcccgaacta   8640
tgactccaga acctaccta  tccgtacagt gtcccaactt accagagaaa tctatactaa   8700
cccagttctt gagaacttcg acggtagctt ccgtggttct gcccaaggta tcgaaggctc   8760
catcaggagc ccacacttga tggacatctt gaacagcata actatctaca ccgatgctca   8820
cagaggagag tattactggt ctggacacca gatcatgacc tctccagttg gattcagcgg   8880
gcccgagttt acctttcctc tctatgaac  tatgggaaac gccgctccac aacaacgtat   8940
cgttgctcaa ctaggtcagg gtgtctacag aaccttgtct tccaccttgt acagaagacc   9000
cttcaatatc ggtatcaaca accagcaact ttccgttctt gacggaacag agttcgccta   9060
tggaacctct tctaacttgc catccgctgt ttacagaaag agcggaaccg ttgattcctt   9120
ggacgaaatc ccaccacaga acaacaatgt gccaccaagg caaggattcc cccacaggtt   9180
gagccacgtg tccatgttcc gttccggatt cagcaacagt tccgtgagca tcatcagagc   9240
tcctatgttc tcttggatac atcgtagtgc tgagttcaac aacatcatcg catccgatag   9300
tattactcaa atccctgcag tgaagggaaa cttctctctc aacggttctg tcatttcagg   9360
accaggattc actggtggag acctcgttag actcaacagc agtggaaata acattcaaga   9420
tagagggtat attgaagttc caattcactt cccatccaca tctaccagat atagagttcg   9480
tgtgaggtat gcttctgtga ccctcattca cctcaacgtt aattgggta  attcatccat   9540
cttctccaat acagttccag ctacagctac ctccttggat aatctccaat ccagcgattt   9600
cggttactt  gaaagtgcca atgcttttac atcttcactc ggtaacatcg tgggtgttag   9660
aaactttagt gggactgcag gagtgattat cgacagattc gagttcattc cagttactgc   9720
aacactcgag gctgagtaca accttgagag agcccagaag gctgtgaacg ccctctttac   9780
ctccaccaat cagcttggct tgaaaactaa cgttactgac tatcacattg accaagtgtc   9840
caacttggtc acctacctta gcgatgagtt ctgcctcgac gagaagcgtg aactcctcga   9900
gaaagtaaaa cacgccaagc gtctcagcga cgagaggaat ctcttgcaag actccaactt   9960
caaagacatc aacaggcagc cagaacgtgg ttggggtgga agcaccggga tcaccatcca  10020
aggaggcgac gatgtgttca aggagaacta cgtcaccctc tccggaactt tcgacgagtg  10080
ctaccctacc tacttgtacc acaaagatcga tgagtccaaa atctactcga tcaggtacaa  10140
tcaacttaga ggctacatcg aagacagcca agaccttgaa atctactcga tcaggtacaa  10200
tgccaagcac gagaccgtga atgtcccagg tactggttcc ctctggccac tttctgccca  10260
atctcccatt gggaagtgtg gagagcctaa cagatgcgct ccacaccttg agtggaatcc  10320
tgacttggac tgctcctgca gggatggcga gaagtgtgcc caccattctc atcacttctc  10380
cttggacatc gatgtgggat gtactgacct gaatgaggac ctcgagtctt gggtcatctt  10440
caagatcaag acccaagacg gacacgcaag acttggcaac cttgagttc  tcgaagagaa  10500
accattggtc ggtgaagctc tcgctcgtgt gaagagagca gagaagaagt ggagggacaa  10560
acgtgagaaa ctcgaatggg aaactaacat cgttacaag  gaggccaaag agtccgtgga  10620
tgctttgttc gtgaactccc aatatgatca gttgcaagcc gacaccaaca tcgccatgat  10680
ccacgccgca gacaaacgtg tgcacagcat tcgtgaggct tacttgcctg agttgtccgt  10740
gatccctggt gtgaacgctg ccatcttcga ggaacttgga ggacgtatct ttaccgcatt  10800
ctccttgtac gatgccagaa acgtcatcaa gaacggtgac ttcaacaatg gcctcagctg  10860
ctggaatgtg aaaggtcatg tggacgtgga ggaacagaac aatcagcgtt ccgtcctggt  10920
tgtgcctgag tgggaagctg aagtgtccca agaggttaga gtctgtccag gtagaggcta  10980
cattctccgt gtgaccgctt acaaggaggg atacggtgag ggttgcgtga ccatccacga  11040
```

```
gatcgagaac aacaccgacg agcttaagtt ctccaactgc gtcgaggaag aaatctatcc   11100
caacaacacc gttacttgca acgactacac tgtgaatcag gaagagtacg gaggtgccta   11160
cactagccgt aacagaggtt acaacgaagc tccttccgtt cctgctgact atgcctccgt   11220
gtacgaggag aaatcctaca cagatggcag acgtgagaac ccttgcgagt caacagagg    11280
ttacagggac tacacaccac ttccagttgg ctatgttacc aaggagcttg agtactttcc   11340
tgagaccgac aaagtgtgga tcgagatcgg tgaaaccgag ggaaccttca tcgtggacag   11400
cgtggagctt ctcttgatgg aggaataatg agatcccgtc ctttgtcttc aattttgagg   11460
gcttttact gaataagtat gtagtactaa aatgtatgct gtaatagctc atagtgagcg   11520
aggaaagtat cgggctattt aactatgact tgagctccat ctatgaataa ataaatcagc   11580
atatgatgct tttgttttgt gtacttcaac tgtctgctta gctaatttga tatggttggc   11640
acttggcacg tataaatatg ctgaagtaat ttactctgaa gctaaattaa ctagattaga   11700
tgagtgtatt atatacaaaa ggcattaaat cagatacatc ttagacaaat tgtcacggtc   11760
taccagaaaa gaaattgcat ttgtttttgg gtctttcaga ctgacaagat cgatctgaag   11820
tctaaacaat tctaagaggt atcatgtagc aatgtcctgc cacaatattg aattgacctg   11880
cagcccgggc ggccgcatcg atcgtgaagt ttctcatcta agcccccatt tggacgtgaa   11940
tgtagacacg tcgaaataaa gatttccgaa ttagaataat ttgttattg ctttcgccta    12000
taaatacgac ggatcgtaat ttgtcgtttt atcaaaatgt actttcattt tataataacg   12060
ctgcggacat ctacattttt gaattgaaaa aaaattggta attactcttt cttttttctcc   12120
atattgacca tcatactcat tgctgatcca tgtagatttc ccggacatga agccatcaaa   12180
aagtaggact aatttaggaa agcaagctaa ttcaagaaag tgaaggcacg cttagtgtga   12240
gacacgtgtt gagcgcgatt actgccactc actaaccaca caagtgcact cagtgcgaag   12300
gttgcttaaa aattaagttg attcgcactt ataaaagaag gatagagtg aaggaaaaaa    12360
cacagaaaat acaattcctt atagaagaca aaggctagaa gaagcaaacg caaacattag   12420
aagtcattcc ttccctcaat tccctttttc aatttcccct tttactaaat attctcctct   12480
tgcaattata aagcctccta tgacaatgac aagctaaact ctcctttgtt gggaacttat   12540
cagtcaactg ctcttaatat aatttctctt cctatctatt atgaatattc actacaagaa   12600
atatgcccat ttgccaggga ttttttgacag ggacattaac ccctggcaaa ttttcccaggga  12660
actaagccaa ggaaacccct ggcaaaatga catttgagaa ggctgggacc acttacattt   12720
acacaggggg ttgtccctcg caaaaataca aaagccttgg caaaaaaaag agcgggaaat   12780
gaattttaaa acagcatgtt gttttcacac agccaaacac acgggtatgc cctcgttttg   12840
tgtaaagctg acggaatctt cccataagtc aacacgacat gaccatgcac tgcaaaaagc   12900
tgtgcggccc agacgtgaca ggggtgttac ccctcggaaa tggcttgcag cccctggcaa   12960
aaaggaatcc ctgcttttcct agctacaccg ttctgctcat atagctgaag ctaggaggtt   13020
agcctttgac tctgttgttt tgcgaggggc attccgtgag ttattccctg ggttttttta   13080
cactatatag ccaaaccgcg tgtttatcct catgctcagt gttgtgtttt tgaaacttag   13140
aaaaattttc ggtttccatt tccatcctca ccagttcatt ttcagtccat tatcattcag   13200
ttcatacact tgttctataa tttggtaaca ctctttttcac ttattatatt tttctgtttt   13260
tatttgttac tacttattaa cataaatatt ttttattgta tcagtgtcca aatttgcctc   13320
ctcctgctgc tccttgctct ctgaatttgt tctcttaagc ttcaacaagt tagtaatttt   13380
tctacttata atttttagata tatgatgttt atatatatga tgttataatt ttgcatgatc   13440
tgtcaaagaa aatatgatgt ttcttacttgc atgatgtgtt ataatatatg atgtttatat   13500
atatttcgaa ttttgttgtt aataaaactg tttaattaga aactgtataa tttttttgtt   13560
taataaaact gtttaatttt gcatgatctg tttaataaaa ctgtttat aaaactgttt    13620
atatataata tatgatgtta acatttttaa aactgtttat aaaacagttt agttagaaaa   13680
aatgttaaaa ctagagaaaa aaatgtataa taaaactgtg tcagtacagc agcgcgtcag   13740
aaaagtgtgc agatgcgtca gtgagaagac aggggctaag acagggattt tgacagggaa   13800
ttttgccagg gattttgcca gggtcagccc ctcgttttt tgccaggggtt gaaatccctg   13860
gcaaactgat ttgcgatggg cgttttttcc agggattcag cccctggcaa aatccctggc   13920
aaacgtccat ttcccaggc ttttttgttct tttcccaggg aatccgcccc tggcaaacga   13980
gcttgttttct tgtagtgatt actttttgcat tagtttttcc tgtatttaat tttattgttt   14040
atggctttgat tacccatttg cattataagt tttagggggta gcgttgaaaa tgtgttattct   14100
ctaatagaac tggaaaagag tatttaaata acttcatcac tagggataca ttgattttat   14160
ttagcttatt atatatctct attattaatg taatttaact attttatctc tgcaaagtga   14220
tttgggagag aagatagata agttagactc tttcactcga ggctgagtac aaccttgaga   14280
gagcccagaa ggctgtgaac gccctcttta cctccaccaa tcagcttggc ttgaaaacta   14340
acgttactga ctatcacatt gaccaagtgt ccaacttggt cacctacctt agcgatgagt   14400
tctgaaggg                                                         14409

SEQ ID NO: 3         moltype = DNA   length = 14436
FEATURE              Location/Qualifiers
source               1..14436
                     mol_type = other DNA
                     organism = synthetic construct
SEQUENCE: 3
gggaaaatcc ctcttccata ttaagaacat aaaaatcaac aggaaaaata agttcaccaa     60
cccgaaccag cacatcctct atgaaacctg cggggtaagc agcacttcta ttttccaaat    120
gaatcaccac atctgtagat tgcaaaggtc aagagataa agaattgaaa atggacagag     180
gggtgacact aactgatgct cctagatcta gcattgtatt atcaaattta ctgttcccaa    240
taatgcaagg tatacagaaa gtacctgggt ccttacattt ctcaggaatg taaggaacaa    300
atttacctat caatgctgac acatttctgc ccatgctaat cctttcattg cctttgagct    360
tccttttgtg ggtgcacaac tccttttagaa acttgacaca tcttggaatc tgcttgatgg    420
catctagcag aggtatgttc acctctactt tcctgaaggt ctccaagatc tccttttctg    480
cttcttccat tttttttgtt tggaattgct caaggttgga atggaagagg gataagaggc    540
tgcggtaagt cagaattact agaagaaggt ccacctgcag gaaaatttt gttaggaagc    600
tttctctttt gtgcaactat ctcatcctct ttttcaggtg tagaatgaag cttgacaggt    660
tcaggtgcgg gtgctgctac tggtggaggt acttgaattt ggttgtcaga cctcaaggtg    720
atgcacactca catttttcgg attttgcaca gtttgtgaag gcaatttgtc agaatttgg    780
gaatgagctt ggttcaactg agtagccatc cgccccatct gatttgtcag actctgaatg    840
aaggctcttg tctcttgctg aaattgcata ttctggatgg tcatttgcct cactaactct    900
```

```
tctaaggaag gttaaggagg agtctcagtt gcttgttgtc tttgttgtga ctgttgttgt   960
tgttgctgct gtattggagg aggaacatat ggtttgcttg gaccagcaac attctggaaa  1020
ggagggacag actgttgttg ttgtgaagga cttgcccatc tcatatttgg atgatttctc  1080
caacctggat tgtatctgtt gcttggaaga tcataattat tttgctattg ttggttttgc  1140
tgttgagggg gtctattata aatgtttgca gcataagctt caggttgttc attgactcca  1200
gattactgca aagaaggaca aagatctgta tggtgatctg cagaagaaca tataccacag  1260
actcttgtaa caggtgcaaa tttctgattc atggcaagct gagttactag ttgaccaag   1320
gcatcaagtt ttccctcaag cttttttattt tcagtagata aagatgaatc tgtggccacc  1380
tcatcgactc ctctaaggac aatagcatca tttcttgcac tgaattgttg ggagttggaa  1440
gccttcttct caatcaaatt cctagcctca gcagggtca tatcacgaag agctccacca   1500
ctggcagcat caatcatact cctctccatg ttgctaagtc cctcatagaa atattgaaga  1560
aggagttgct cagaaatctg gtggtgagga cagcttgcac acaatttctt gaatctttct  1620
cagtactcat acaagctctc tccactaagt tgcctgatgc ctgaaatttc ttttctgatg  1680
gcagtggtcc tagatgcagg gaagaatttc tccaagaaca ccctcttaag gtcatcccag  1740
ctgaaaatgg acctgggagc aaggtagtag agccaatctt ttgtcactac ctccagagaa  1800
tgaggaaaag cctttagaaa gatatgatct tcttggacat caggggggctt catggtggaa  1860
caaacaatat ggaactcctt aagatgctta tgaggatctc cacctagaag accatgaaac  1920
ttgggtagca aatgtattag tccagtcttg agaacatgga gaacaccctc atcaggatat  1980
tgaatgcaca agttttcata agtgaaatca ggtgcagcca tctccctaag agtcctctca  2040
cgaggtggag gtttagccat gttctcagta tgaaaattag tagttgaatg ctcaaaatca  2100
gaatattcag aatcaccaga aacaaatac tcagaatgct caaatgctc aaatgcaca    2160
taatgattag gatgcacact atgcctaact aatcatgaa aggttctatc tatttcagga   2220
tcgaagggtt ataaatcacc tagattgccc ctagtcatga actatatgta gcaaataatg  2280
tgttctcaaa caagcaccaa gggagggtta aaactacaac tatagtcaaa tgatatccaa  2340
atgagttgaa attttgtgag cagcacccta aaatcatgaa aagatagcac aaaaaatttc  2400
aaacgaaaat tcaaagtcta actatgaaaa ctacttaaga aagtttaga aaaataggac   2460
aataatactt gaaaataaaa aaaaacata gtaaacagct gattttcga gtttgggaga    2520
ctccaaccgg ctaaaacggg ttgccacaat atgagaaatt ttttttctac ccaaaatgcca 2580
caatatgaga aagttttgct aaaatctagt tcccaaaatt tttgtctctc tcaaattcaa  2640
ccacaccagg tgctcctagt attttttcaca caaaaaaatca gccaaaaata acaactctaa 2700
ctatcaaaac aaaaacagct aattaaattg caaaatcagt cgctaattcc tagtcactaa  2760
tcactgttca cagcaaaaca ccaactgaat cagtcgctaa acagtcgcta aacaggagac  2820
gcaactgaaa tgcaaaacag aatgctacac aaaacaaaac aactaaacac tattatgaac  2880
ctttggccca ctgctccccg caacggcgc caaatttgat cgaggtcgta cccgaatcaa  2940
ataaacatta aaaatgcagt atctaggaag tgatcctagg tcatctccca acgagcaatg  3000
gtcaaccaat gttcataata gatagtgata aaacaataac gaattggggg ggggggtat    3060
ttgttttttgt aatttaaaca acaagcaaat tttaattaga aaataacaga attaaaacat  3120
gttatttccc cttgattcat aagcaagtct cttatcctag gttaggagga tttatcccta  3180
accagttcaa ccacttaatc caaccctaaa ttaaattact aagcgaaaat taacataagg  3240
ttgtctttat atgattaagc aacacataca ccaattaatc atgaacaaaa tcgatcatta  3300
agcatcaaca taaattaagc gcaaagataa ttaatcaagc actaagcatg catggattag  3360
tagcaacaaa tacagagtaa ttggtggaga tgaaaaactg atcaatattc aatagtaata  3420
acaaaaccct caaagagagtt gtgcttgatt ctcaagagaa acaacgcgtg gagacttagc  3480
cttccattaa tcagtagaaa acgaaattgt agaaaacgaa ttttattcta tgtgaacaat  3540
gtgcatgaac agtaataaaa actggaattg caaaacccta aaattattct tctctcccaaa 3600
aaaactccct aaactaaaac cctggtgcta ttatataggt cctcagcccc aaagcttaca  3660
aatctatttt cagtccaaac ccataaacga aataaaataa aactggaca agataagata   3720
agattggatg aaataaaatc tggacgaaat aaaatctgga taagataaga tttgataaaa  3780
taaaattgtc tgctcttttc aagtccaagc ccaattccgg attcaagccc aattttttat  3840
aattcttctg aaattaaatt aaaaaatacga aattagtcaa gtaggcccaa atgataaaac  3900
tgcataatta atttgacaat taaggctaat cagtaattaa aatagtgaca aaaaggttga  3960
agaaatagga gaataatgac acatcaccca tatgggagc aattctaaaa tgcatttgag   4020
ttcttttaacc tgagacacag tgcagtagag tctccaagga ttcattgtgc cttttatttt  4080
atatgatggg gtcactacat tggccttgtc aaagaaactg aatttggggg attaaagaaa  4140
cacaaaataa aaacaaatga aactagttaa tagaaatgtt gcctattgct tcttggaaaa  4200
agtccaacca tttgtgatttt ggataaaatt catattaccc acttgtagct tgttcaatca  4260
aacactagat ttggataaaa tctcactcct agatatacct caagggataa tatgaccaac  4320
attagtcatt tttagaaagt aaagtggaca aatttgagat ttcattcctt aatgacatta  4380
taaacatgta ttttttccat gaccctttt caatgtaagt acaatttatc ccttagttta   4440
gatactctat atatgcatgt tacgtagttg atgaaaacat acctaagttg ttgtgtatgg  4500
ttaagtttgc gactacctct gatatcaaac tcctcatctc caatctcata caaaagatac  4560
ttgtcacttg gtacctgaac cttgtcagtt tgcagttgtg agtttcttct gaagccacac  4620
gcttgtatag taaccagaag ccaggaggga gtcctctaag gctctaactc gtatttccg   4680
tggaagtaca ttttttttct taaagaaaac agagatagtt taccaatgat aatatttctt  4740
tagccaaata ggaccatcat agaaaacaaa actcttcttc taagtattta atgcaactac  4800
atatttaggg tgcgtttgat tcgctaaaaa ataagggtct agacaacaca aaaatatttt  4860
tccaacgttt gattttaaaa atggctgaga gacaatacaa aataaagaat gatgaactgg  4920
acaaaaacct aaaaacttgt aactcactga atctcataca actttttgtt cagtgtctaa  4980
aaaaagtaaa aatacaatat tattcctatt ttttactttg attatctcac accttctttc  5040
tactcatttg tttcacttca cctctccagt gggcaccttg gtttgtcggc gagagtcgta  5100
tggacttttg ttgttttcctt tttgctcatt atttcttttct tttcattgtt aatttattca  5160
aatgttccca tcatcatctt actccttctt gttatgtttt ttttctttgg ccaactccaa  5220
cgaggccgtg ccgcgaccac catcatcacg acctatggc ggcctcacgc cgcaaggccc   5280
tgcacccagt ggcatcaggg gtcatgcctc cttcttaaag gtgtctctct tttgttatgt  5340
cgtcaaagtg ttgctaattc acctagaatt tttcaatgaa tcccttact tgtgggttag    5400
tctaggtcgc tctgccggt tccaacccta gcccaaaaaa aaatgaaatg ggtaggaaag   5460
gcgggcctag tttgaattaa aataaatcat gctaagatat tgataactgc tatgtatagg   5520
tatattttgg gattaaatta tataggaatt agtaattttt ctctcttatt tcttcctttt  5580
tgttcaaata attggaattc taacatcatt taagttttta tgtagaaaat attaaaagtt  5640
```

```
gatgaattta tgatacttag tgaataatta gagtagaaaa ataaagtaaa gcccaaaaaa   5700
gaaaattggt gatatgaaga tacatgctta gcatgcccca ggcacgctta gtgtgtgtgt   5760
caaacttttcc taaattagtc ctacttttg atgtttaaac tgaaggcggg aaacgacaat   5820
ctgatcccca tcaagcttga tatcgaattc ctgcagcccg ggggatccac tagttctaga   5880
gcggccgcgt taactgcagg tcgacggatc cccgggtacc gagctcgaat tcaaatttat   5940
tatgtgtttt ttttccgtgg tcgagattgt gtattattct ttagttatta caagactttt   6000
agctaaaatt tgaaagaatt tactttaaga aaatcttaac atctgagata atttcagcaa   6060
tagattatat ttttcattac tctagcagta ttttttgcaga tcaatcgcaa catatatggt   6120
tgttagaaaa aatgcactat atatatatat atttattttt caattaaaag tgcatgatat   6180
ataatatata tatatatata tatgtgtgtg tgtatatggt caaagaaatt cttatacaaa   6240
tatacacgaa cacatatatt tgacaaaatc aaagtattac actaaacaat gagttggtgc   6300
atggccaaaa caaatatgta gattaaaaat tccagcctcc aaaaaaaaat ccaagtgttg   6360
taaagcatta tatatatata gtagatccca aattttttgta caattccaca ctgatcgaat   6420
ttttaaagtt gaatatctga cgtaggattt ttttaatgtc ttacctgacc atttactaat   6480
aacattcata cgtttcatt tgaaaatatcc tctataatta tattgaattt ggcacataat   6540
aagaaaccta attggtgatt tattttacta gtaaatttct ggtgatgggc tttctactag   6600
aaagctctcg gaaaatcttg gaccaaatcc atattccatg acttcgattg ttaaccctat   6660
tagttttcac aaacatacta tcaatatcat tgcaacgaaa aagtacaag taaaacattc   6720
aatccgatag ggaagtgatg taggaggttg ggaagacagg cccagaaaga gatttatctg   6780
acttgttttg tgtatagttt tcaatgttca taaaggaaga tggagacttg agaagttttt   6840
tttgactttt gtttagcttt gttgggcgtt ttttttttg atcaataact ttgttgggct   6900
tatgatttgt aatatttttcg tggactcttt agtttattta gacgtgctaa ctttgttggg   6960
cttatgactt gttgtaacat attgtaacag atgacttgat gtgcgactaa tctttacaca   7020
ttaaacatag ttctgttttt tgaaagttct tattttcatt tttatttgaa tgttatatat   7080
ttttctatat ttataattct agtaaaaggc aaattttgct tttaaatgaa aaaatatat   7140
attccacagt ttcacctaat cttatgcatt tagcagtaca aattcaaaaa tttcccattt   7200
ttattcatga atcataccat tatatattaa ctaaatccaa ggtaaaaaaa aggtatgaaa   7260
gctctatagt aagtaaaata taaattcccc ataaggaaag ggccaagtcc accaggcaag   7320
taaaatgagc aagcaccact ccaccatcac acaatttcac tcatagataa cgataagatt   7380
catggaatta tcttccacgt ggcattattc cagcggttca agccgataag ggtctcaaca   7440
cctctcctta ggcctttgtg gccgttacca agtaaaatta acctcacaca tatccacact   7500
caaaatccaa cggtgtagat cctagtccac ttgaatctca tgtatcctag accctccgat   7560
cactccaaag cttgttctca ttgttgttat cattatatat agatgaccaa agcactagac   7620
caaacctcag tcacacaaag agtaaagaag aacaatggct tcctctatgc tctcttccgc   7680
tactatggtt gcctctccgg ctcaggccac tatggtcgct cctttcaacg gacttaagtc   7740
ctccgctgcc ttcccagcca cccgcaaggc taacaacgac attacttcca tcacaagcaa   7800
cggcggaaga gttaactgca tgcaggtgtg gcctccgatt ggaagaaga gtttgagac   7860
tctctcttac cttcctgacc ttaccgattc cggtggtcgc gtcaactgca tgcaggccat   7920
ggacaacaac ccaaacatca acgaatgcat tccatacaac tgcttgagta acccagaagt   7980
tgaagtactt ggtggagaac gcattgaaac cggttacact cccatcgaca tctccttgtc   8040
cttgacacag tttctgctca gcgagttcgt gccaggtgct gggttcgttc tcggactagt   8100
tgacatcatc tgggggtatct ttggtccatc tcaatgggat gcattcctgg tgcaaattga   8160
gcagttgatc aaccagagga tcgaagagtt cgccaggaac caggccatct ctaggttgga   8220
aggattgagc aatctctacc aaatctatgc agagagcttc agagagtggg aagccgatcc   8280
tactaaccca gctctccgcg aggaaatgcg tattcaattc aacgacatga acagcgcctt   8340
gaccacagct atcccattgt tcgcagtcca gaactaccaa gttcctctct tgtccgtgta   8400
cgttcaagca gctaatcttc acctcagcgt gcttcgagac gttagcgtgt ttgggcaaag   8460
gtggggattc gatgctgcaa ccatcaatag ccgttacaac gacctactaa ggctgattgg   8520
aaaactacacc gaccacgctg ttcgttggta caacactggc ttgagcgtg tctgggtcc   8580
tgattctaga gattggatta gatacaacca gttcaggaga gaattgaccc tcacagtttt   8640
ggacattgtg tctctcttcc cgaactatga tcccagaacc tacccctatc gtacagtgtc   8700
ccaacttacc agagaaatct atactaaccc agttcttgag aacttcgacg tagcttccg   8760
tggttctgcc caaggtatcg aaggctccat caggagccca cacttgatgg acatcttgaa   8820
cagcataact atctacaccg atgctcacag aggagagtat tactggtctg acaccagat   8880
catggcctct ccagttggat tcagcgggcc cgagtttacc tttcctctct atggaactat   8940
gggaaacgcc gctccacaac aacgtatcgt tgctcaacta ggtcagggtg tctacagaac   9000
cttgtcttcc accttgtaca gaagacccctt caatatcggt atcaacaacc agcaactttc   9060
cgttcttgac ggaacagagt tcgcctatgg aacctcttct aacttgccat ccgctgttta   9120
cagaaagagc ggaacccgttg attccttgga cgaaatccca ccacagaaca acaatgtgag   9180
acccaggcaa ggattctccc acaggttgag ccacgtgtcc atgttccgtt ccggattcag   9240
caacagttcc gtgagcatca tcagagctcc tatgttctct tggatacatc gtagtgctga   9300
gttcaacaac atcatcgcat ccgatagtat tactcaaatc cctgcagtga agggaaactt   9360
tctcttcaac ggttctgtca tttcaggacc aggattcact ggtggagacc tcgttagact   9420
caacagcagt ggaaataaca ttcagaatag agggtattt gaagttccaa ttcacttccc   9480
atccacatct accagatata gagttcgtgt gaggtatgct tctgtgaccc ctattccct   9540
caacgttaat tggggtaatt catccatctt ctccaataca gttccagcta cagctaccttc   9600
cttggataat ctccaatcca gcgatttcgg ttactttgaa agtgccaatg ctttacatc   9660
ttcactcggt aacatcgtgg tgttagaaa cttagtggg actgcaggag tgattatcga   9720
cagattcgag ttcattccag ttactgcaac actcgagagt gagtacaacc ttgagagagc   9780
ccagaaggct gtgaacgccc tctttacctc caccaatcag cttggcttga aaactaacgt   9840
tactgactat cacattgacc aagtgtccaa cttggtcacc taccttagcg atgagttctg   9900
cctcgacgag aagcgtgaac tctccgagaa agttaaacac gccaagcgtc tcagcgacga   9960
gaggaatctc ttgcaagact ccaacttcaa agacatcaac aggcagccag aacgtggttg  10020
gggtgaaagc accgggatca catccaagg aggcgacgat ggttcaagg agaactaagt  10080
caccctctcc ggaactttcg acgagtgcta ccctacctac ttgtaccaga agatcgatga  10140
gtccaaactc aaagccttca ccaggtatca acttagaggc tacatcgaag acagccaaga  10200
ccttgaaatc tactcgatca ggtacaatgc caagcacgag accgtgaatg tcccaggtac  10260
tggttccctc tggccacttt ctgcccaatc tccccattggg aagtgtggag agcctaacag  10320
atgcgctcca caccttgagt ggaatcctga cttggactgc tcctgcaggg atggcgagaa  10380
```

```
gtgtgcccac cattctcatc acttctcctt ggacatcgat gtgggatgta ctgacctgaa  10440
tgaggacctc ggagtctggg tcatcttcaa gatcaagacc caagacggac acgcaagact  10500
tggcaacctt gagtttctcg aagagaaacc attggtcggt gaagctctcg ctcgtgtgaa  10560
gagagcagag aagaagtgga gggacaaacg tgagaaactc gaatgggaaa ctaacatcgt  10620
ttacaaggag gccaaagagt ccgtggatgc tttgttcgtg aactcccaat atgatcagtt  10680
gcaagccgac accaacatcg ccatgatcca cgccgcagac aaacgtgtgc acagcattcg  10740
tgaggcttac ttgcctgagt tgtccgtgat ccctggtgtg aacgctgcca tcttcgagga  10800
acttgaggga cgtatcttta ccgcattctc cttgtacgat gccagaaacg tcatcaagaa  10860
cggtgacttc aacaatggcc tcagctgctg gaatgtgaaa ggtcatgtgg acgtggagga  10920
acagaacaat cagcgttccg tcctggttgt gcctgagtgg gaagctgaag tgtcccaaga  10980
ggttagagtc tgtccaggta gaggctacat tctccgtgtg accgcttaca aggagggata  11040
cggtgagggt tgcgtgacca tccacgagat cgagaacaac accgacgagc ttaagttctc  11100
caactgcgtc gaggaagaaa tctatcccaa caaccgtt acttgcaacg actacactgt  11160
gaatcaggaa gagtacgaag gtgcctacac tagccgtaac agaggttaca acgaagctcc  11220
ttccgttcct gctgactatg cctccgtgta cgaggagaaa tcctacacag atggcagacg  11280
tgagaaccct tgcgagttca acagaggtta cagggactac acaccacttc cagttggcta  11340
tgttaccaag gagcttgagt actttcctga gaccgacaaa gtgtgggatcg agatcggtga  11400
aaccgaggga accttcatcg tggacagcgt ggagcttctc ttgatggagg aataatgaga  11460
tcccgtcctt tgtcttcaat tttgagggct ttttactgaa taagtatgta gtactaaaat  11520
gtatgctgta atagctcata gtgagcgagg aaagtatcgg gctatttaac tatgacttga  11580
gctccatcta tgaataaata aatcagcata tgatgctttt gttttgtgta cttcaactgt  11640
tgcttagct aatttgatat ggttgcact tggcacgtat aaaatatgctg aagtaattta  11700
ctctgaagct aaattaacta gattagatga gtgtattata tacaaaaggc attaaatcag  11760
atacatctta gacaaattgt cacggtctac cagaaaagaa attgcatttg tttttgggtc  11820
tttcagactg acaagatcga tctgaagtct aaacaattct aagaggtatc atgtagcaat  11880
gtcctgccac aatattgaat tgacctgcag cccgggcggc tgcatcgatc gtgaagtttc  11940
tcatctaagc ccccatttgg acgtgaatgt agacacgtcg aaataaagat ttccgaatta  12000
gaataatttg tttattgctt tcgcctataa atacgacgga tcgtaatttg tcgttttatc  12060
aaaatgtact ttcatttat aataacgctg cggacatcta catttttgaa ttgaaaaaaa  12120
attggtaatt actcttttctt tttctccata ttgaccatca tactcattgc tgatccatgt  12180
agatttcccg gacatgaagc catcaaaaag taggactaat ttaggaaagc aagctaattc  12240
aagaaagtga aggcacgctt agtgtgagac acgtgttgag cgcgattact gccactcact  12300
aaccacacaa gtgcactcag tgcgaaggtt gcttaaaaat taagttgatt cgcacttata  12360
aaagaaggat agagatgaag gaaaaaacac agaaaataca attccttata gaagacaaag  12420
gctagaagaa gcaaacgcaa acattagaag tcattccttc cctcaattcc cttttttcaat  12480
ttccccttttt actaaatatt ctcctcttgc aattataaag cctccatga caatgacaag  12540
ctaaactctc ctttgttggg aacttatcag tcaactgctc ttaatataat ttctcttcct  12600
atctattatg aatattcact acaagaaata tgcccatttg ccaggggattt ttgacaggga  12660
cattaaatcc tggcaaattt cccagggact aagccaagga aaccccctgg caaaatgacat  12720
ttgagaaggc tgggaccact tacatttaca caggggtttg tccctcgcaa aaatacaaaa  12780
gccttggcaa aaaaaagagc gggaaatgaa ttttaaaaca gcatgttgtt ttcacacagc  12840
caaacacacg ggtatgccct cgttttctgt aaagctgacg gaatcttccc ataagtcaac  12900
acgacatgac catgcactgc aaaaagctgt gcggcccaga cgtgacaggg gtgttaccc  12960
tcggaaatgg cttgcagccc ctggcaaaaa ggaatccctg cttttcctagc tacaccgttc  13020
tgctcatata gctgaagcta ggaggttagc ctttgactct gttgtttttgc gaggggcatt  13080
ccgtgagtta ttccctgggt ttttttacac tatatagcca aaccgcgtgt ttatcctcat  13140
gctcagtgtt gtgttttga aacttagaaa aattttcgtt ttccatttcc atcctcacca  13200
gttcatttc agtccattat cattcagttc atacacttgt tctataattt ggtaacactc  13260
ttttcactta ttatatttt ctgttttat tgttactac ttattaacat aaatatttt  13320
tattgtatca gtgtccaaat ttgcctcctc ctgctgctcc ttgctctctg aatttgttct  13380
cttaagcttc aacaagttag taatttttct acttataatt ttagatatat gatgtttata  13440
tatatgatgt tataattttg catgatctgt caaagaaaat atgatgtttc tacttgcatg  13500
atgtgttata atatatgatg tttatatata tttcgaattt tgttgttaat aaaactgttt  13560
aattagaaac tgtataattt ttttgtttaa taaaactgtt taattttgca tgatctgttt  13620
aataaaactg tttatataaa actgtttata tataatat gatgttaaca ttttttaaaac  13680
tgttttaaaa acagtttagt tagaaaaaat gttaaaacta gagaaaaaaa tgtataataa  13740
aactgtgtca gtacagcagc gcgtcagaaa agtgtgcaga tgcgtcagtg agaagacagg  13800
ggctaagaca gggattttga cagggaattt tgccagggat tttgccaggg tcagcccctc  13860
gttttttgc caggggtgaa atccctggca aactgatttg cgatgggcgt ttttcccagg  13920
gattcagccc ctgcaaaat ccctggcaaa cgtccatttc ccagggcttt ttgttcttt  13980
cccagggaat ccgcccctgg caaacgagct tgtttcttgt agtgattact tttgcattag  14040
ttttttcctgt atttaatttt attgtttatg cttgattac ccattgcat tataagtttt  14100
aggggtagcg ttgaaaagtg ttattctcta atagaactgg aaaagagtat ttaaataact  14160
tcatcactag ggatacattg attttattta gcttattata tatctcatt attaatgtaa  14220
tttaactatt ttatctctgc aaagtgattt gggagagaag atagataagt tagactcttt  14280
cactcgaggc tgagtacaac cttgagagag cccagaaggc tgtgaacgcc ctctttacct  14340
ccaccaatca gcttggcttg aaaactaacg ttactgacta tcacattgac caagtgtcca  14400
acttggtcac ctacccttagc gatgagttct gaaggg                          14436

SEQ ID NO: 4       moltype = DNA  length = 27
FEATURE            Location/Qualifiers
source             1..27
                   mol_type = other DNA
                   organism = synthetic construct
SEQUENCE: 4
tttaaactat cagtgtttga cacacac                                       27

SEQ ID NO: 5       moltype = DNA  length = 27
FEATURE            Location/Qualifiers
```

```
source                  1..27
                        mol_type = other DNA
                        organism = synthetic construct
SEQUENCE: 5
tttcccgcct tcagttttaaa ctatcag                                           27

SEQ ID NO: 6            moltype = DNA   length = 27
FEATURE                 Location/Qualifiers
source                  1..27
                        mol_type = other DNA
                        organism = synthetic construct
SEQUENCE: 6
tttcctaaat tagtcctact ttttgat                                            27

SEQ ID NO: 7            moltype = DNA   length = 47
FEATURE                 Location/Qualifiers
source                  1..47
                        mol_type = other DNA
                        organism = synthetic construct
SEQUENCE: 7
gcacgcttag tttcctaaat tagtcctact ttttgatgtc aaacact                      47

SEQ ID NO: 8            moltype = DNA   length = 47
FEATURE                 Location/Qualifiers
source                  1..47
                        mol_type = other DNA
                        organism = synthetic construct
SEQUENCE: 8
tgtgtcaaac tttcctaaat tagtcctact ttttgatgtt taaactg                      47

SEQ ID NO: 9            moltype = DNA   length = 1127
FEATURE                 Location/Qualifiers
source                  1..1127
                        mol_type = other DNA
                        organism = synthetic construct
SEQUENCE: 9
tttctttggc caactccaac gaggccgtgc cgcgaccacc atcatcacga ccttatggcg        60
gcctcacgcc gcaaggccct gcacccagtg gcatcagggg tcatgcctcc ttcttaaagg       120
tgtctctctt ttgttatgtc gtcaaagtgt tgctaattca cctagaattt ttcaatgaat       180
cccctttactt gtgggttagt ctaggtcgct ctgcccggtt ccaaccctag cccaaaaaaa      240
aatgaaatgg gtaggaaagg cgggcctagt ttgaattaaa ataaatcatg ctaagatatt       300
gataactgct atgtataggt atattttggg attaaattat ataggaatta gtaatttttc       360
tctcttattt cttccttttt gttcaaataa ttggaattct aacatcattt aagttttat       420
gtagaaaata ttaaagttg atgaatttat gatacttagt gaataattag agtagaaaaa       480
taaagtaaag cccaaaaaag aaaattggtg atatgaagat acatgcttag catgcccag       540
gcacgcttag tttcctaaat tagtcctact ttttgatgtc aaacactgat agtttaaact       600
gaaggcggga aacgacaatc tgatccccat caagcttgat atcgaattcc tgcagcccgg       660
gggatccact agttctagag cggccgcgtt aactgcaggt cgacggatcc ccgggtaccg       720
agctcgaatt caaatttatt atgtgttttt tttccgtggt cgagattgtg tattattctt       780
tagttattac aagacttta gctaaaattt gaaagaattt actttaagaa aatcttaaca       840
tctgagataa tttcagcaat agattatatt tttcattact ctagcagtat ttttgcagat       900
caatcgcaac atatatggtt gttagaaaaa atgcactata tatatatata ttatttttc       960
aattaaaagt gcatgatata taatatatat atatatatat atgtgtgtgt gtatatggtc      1020
aaagaaattc ttatacaaat atacacgaac acatatattt gacaaaatca agtattaca      1080
ctaaacaatg agttggtgca tggccaaaac aaatatgtag attaaaa                    1127

SEQ ID NO: 10           moltype = DNA   length = 1386
FEATURE                 Location/Qualifiers
source                  1..1386
                        mol_type = other DNA
                        organism = synthetic construct
SEQUENCE: 10
tttgtcggcg agagtcgtat ggactttgt tgtttccttt ttgctcatta tttctttctt        60
tcattgtta atttattcaa atgttcccat catcatctta ctccttcttg ttatgttttt       120
tttctttggc caactccaac gaggccgtgc cgcgaccacc atcatcacga ccttatggcg      180
gcctcacgcc gcaaggccct gcacccagtg gcatcagggg tcatgcctcc ttcttaaagg      240
tgtctctctt ttgttatgtc gtcaaagtgt tgctaattca cctagaattt ttcaatgaat      300
cccttactt gtgggttagt ctaggtcgct ctgcccggtt ccaaccctag cccaaaaaaa       360
aatgaaatgg gtaggaaagg cgggcctagt ttgaattaaa ataaatcatg ctaagatatt      420
gataactgct atgtataggt atattttggg attaaattat ataggaatta gtaatttttc     480
tctcttattt cttccttttt gttcaaataa ttggaattct aacatcattt aagttttat      540
gtagaaaata ttaaagttg atgaatttat gatacttagt gaataattag agtagaaaaa      600
taaagtaaag cccaaaaaag aaaattggtg atatgaagat acatgcttag catgcccag      660
gcacgcttag tgtgtgtc aaacactgat agtttaaact gaaggcggga aacgacaatc       720
tgatccccat caagcttgat atcgaattcc tgcagcccgg gggatccact agttctagag      780
cggccgcgtt aactgcaggt cgacggatcc ccgggtaccg agctcgaatt caaatttatt     840
atgtgttttt tttccgtggt cgagattgtg tattattctt tagttattac aagacttta      900
gctaaaattt gaaagaattt actttaagaa aatcttaaca tctgagataa tttcagcaat     960
agattatatt tttcattact ctagcagtat ttttgcagat caatcgcaac atatatggtt   1020
```

```
gttagaaaaa atgcactata tatatatata ttatttttc aattaaaagt gcatgatata    1080
taatatatat atatatatat atgtgtgtgt gtatatggtc aaagaaattc ttatacaaat    1140
atacacgaac acatatattt gacaaaatca aagtattaca ctaaacaatg agttggtgca    1200
tggccaaaac aaatatgtag attaaaaatt ccagcctcca aaaaaaaatc caagtgttgt    1260
aaagcattat atatatatag tagatcccaa attttttgtac aattccacac tgatcgaatt    1320
tttaaagttg aatatctgac gtaggatttt tttaatgtct tacctgacca tttactaata    1380
acattc                                                               1386

SEQ ID NO: 11              moltype = DNA   length = 23
FEATURE                    Location/Qualifiers
source                     1..23
                           mol_type = other DNA
                           organism = synthetic construct
SEQUENCE: 11
ctaaattagt cctactttt gat                                             23

SEQ ID NO: 12              moltype = DNA   length = 25
FEATURE                    Location/Qualifiers
source                     1..25
                           mol_type = other DNA
                           organism = synthetic construct
SEQUENCE: 12
tttgtcggcg agagtcgtat ggact                                          25

SEQ ID NO: 13              moltype = DNA   length = 25
FEATURE                    Location/Qualifiers
source                     1..25
                           mol_type = other DNA
                           organism = synthetic construct
SEQUENCE: 13
gaatgttatt agtaaatggt caggt                                          25

SEQ ID NO: 14              moltype = DNA   length = 1406
FEATURE                    Location/Qualifiers
source                     1..1406
                           mol_type = other DNA
                           organism = synthetic construct
SEQUENCE: 14
tttgtcggcg agagtcgtat ggactttgt tgtttccttt ttgctcatta tttctttctt     60
ttcattgtta atttattcaa atgttcccat catcatctta ctccttcttg ttatgttttt    120
tttctttggc caactccaac gaggccgtgc cgcgaccacc atcatcacga ccttatggcg    180
gcctcacgcc gcaaggccct gcacccagtg gcatcagggg tcatgcctcc ttcttaaagg    240
tgtctctctt ttgttatgtc gtcaaagtgt tgctaattca cctagaattt ttcaatgaat    300
cccttttactt gtgggttagt ctaggtcgct ctgcccggtt ccaaccctag cccaaaaaaa    360
aatgaaatgg gtaggaaagg cgggcctagt ttgaattaaa ataaatcatg ctaagatatt    420
gataactgct atgtataggt atattttggg attaaattat ataggaatta gtaattttc     480
tctcttatttt cttccttttt gttcaaataa ttggaattct aacatcattt aagttttat    540
gtagaaaata ttaaagttg atgaattat gatacttagt gaataattag agtagaaaaa      600
taaagtaaag cccaaaaaag aaaattggtg atatgaagat acatgcttag catgccccag    660
gcacgcttag tttcctaaat tagtcctact ttttgatgtc aaacactgat agtttaaact    720
gaaggcggga aacgacaatc tgatcccat caagcttgat atcgaattcc tgcagcccgg     780
gggatccact agttctagag cggccgcgtt aactgcaggt cgacggatcc ccgggtaccg    840
agctcgaatt caaattttatt atgtgttttt tttccgtggt cgagattgtg tattattctt    900
tagttattac aagactttta gctaaaattt gaaagaattt actttaagaa aatcttaaca    960
tctgagataa tttcagcaat agattatatt tttcattact ctagcagtat ttttgcagat   1020
caatcgcaac atatatggtt gttagaaaaa atgcactata tatatatata ttatttttc    1080
aattaaaagt gcatgatata taatatatat atatatatat atgtgtgtgt gtatatggtc   1140
aaagaaattc ttatacaaat atacacgaac acatatattt gacaaaatca aagtattaca   1200
ctaaacaatg agttggtgca tggccaaaac aaatatgtag attaaaaatt ccagcctcca   1260
aaaaaaaatc caagtgttgt aaagcattat atatatatag tagatcccaa attttttgtac  1320
aattccacac tgatcgaatt tttaaagttg aatatctgac gtaggatttt tttaatgtct   1380
tacctgacca tttactaata acattc                                        1406

SEQ ID NO: 15              moltype = DNA   length = 14436
FEATURE                    Location/Qualifiers
source                     1..14436
                           mol_type = other DNA
                           organism = synthetic construct
SEQUENCE: 15
gggaaaatcc ctcttccata ttaagaacat aaaaatcaac aggaaaaata agttcaccaa     60
cccgaaccag cacatcctct atgaaacctg cggggtaagc agcacttcta ttttccaaat    120
gaatcaccac atctgtagat tgcaaaggtc caagagataa agaattgaaa atggacagag    180
gggtgacact aactgatgct cctagatcta gcattgtatt atcaaattta ctgttcccaa    240
taatgcaagg tatacagaaa gtacctgggt ccttacattt ctcaggaatg taaggaacaa    300
atttacctat caatgctgac acatttctgc ccatgctaat cctttcattg cctttgagct    360
tcctttttgtg ggtgcacaac tcctttagaa acttgacaca tcttggaatc tgcttgatgg    420
catctagcag aggtatgttc acctctactt tcctgaaggt ctccaagatc tccttttctg    480
cttcttccat tttttttgtt tggaattgct caaggttgga atggaagagg ataagaggc     540
tgcggtaagt cagaattact agaagaaggt ccacctgcat gaaaattttt gttaggaagc    600
```

```
tttctctttt gtgcaactat ctcatcctct ttttcaggtg tagaatgaag cttgacaggt   660
tcaggtgcgg gtgctgctac tggtggaggt acttgaattt ggttgtcaga cctcaaggtg   720
atgacactca cattttttcgg attttgcaca gtttgtgaag gcaatttgtc agaattttgg   780
gaatgagctt ggttcaactg agtagccatc cgccccatct gatttgtcag actctgaatg   840
aaggctcttg tctcttgctg aaattgcata ttctggattc tcatttgcct cactaactct   900
tctaaggaag gttaaggagg agtctcagtt gcttgttgtc tttgttgtga ctgttgttgt   960
tgttgctgct gtattggagg aggaacatat ggttgcttg gaccagcaac attctggaaa   1020
ggagggacag actgttgttg ttgtgaagga cttgcccatc tcatatttgg atgatttctc   1080
caacctggat tgtatctgtt gcttggaaga tcataattat tttgctattg ttggtttttgc  1140
tgttgagggg gtctattata aatgtttgca gcataagctt caggttgttc attgactcca   1200
gattactgca aagaaggaca aagatctgta tggtgatctg cagaagaaca tataccacag   1260
actcttgtaa caggtgcaaa tttctgattc atggcaagct gagttactag gttgaccaag   1320
gcatcaagtt ttccctcaag cttttttattt tcagtagata aagatgaatc tgtggccacc   1380
tcatcgactc ctctaaggac aatagcatca tttcttgcac tgaattgttg ggagttgaa    1440
gccttcttct caatcaaatt cctagcctca gcagggggtca tatcacgaag agctccacca  1500
ctggcagcat caatcatact cctctccatg ttgctaagtc cctcatagaa atattgaaga   1560
aggagttgct cagaaatctg gtggtgagga cagcttgcac acaatttctt gaatctttct   1620
cagtactcat acaagctctc tccactaagt tgcctgatgc ctgaaatttc ttttctgatg   1680
gcagtggtcc tagatgcagg gaagaatttc tccaagaaca ccctcttaag gtcatcccag   1740
ctgaaaatgg aactgggagc aaggtagtag agccaatctt ttgtcactac ctccagagaa   1800
tgaggaaaag cctttagaaa gatatgatct tcttggacat caggggcctt catggtgaa   1860
caaacaatat ggaactcctt aagatgctta tgaggatctt cacctagaag accatgaaac   1920
ttgggtagca aatgtattag tccagtcttg agaacatatg gaacaccctc atcaggatat   1980
tgaatgcaca agtttcata agtgaaatca ggtgcagcca tctccctaag agtcctctca   2040
cgaggtggag gtttagccat gttctcagta tgaaaattag tagttgaatg ctcaaaatca   2100
gaatattcag aatcaccaga aacaaaatac tcagaatgct caaaatgctc aaaatgcaca   2160
taatgattag gatgcacact atgcctaact aatctatgaa aggttctatc tatttcagga   2220
tcgaagggtt ataaatcacc tagattgccc ctagtcatgc actatatgta gcaaataatg   2280
tgttctcaaa caagcaccaa gggagggtta aaactacaac tatagtcaaa tgatatccaa   2340
atgagttgaa attttgtgag cagcacccta aaatcatgaa aagatagcac aaaaaatttc   2400
aaacgaaaat tcaaagtcta actatgaaaa ctacttaaga aaagtttaga aaataggac    2460
aataatactt gaaaataaaa aaaaacata gtaaacagct gattttttcga gtttgggaga   2520
ctccaaccgg ctaaacgggt tgccacaat atgagaaatt ttttttctacc ccaaatgcca   2580
caatatgaga aagttttgct aaaatctagt tcccaaaatt tttgtctctc tcaaattcaa   2640
ccacaccaag tgctcctagt attttttcaca caaaaatca gccaaaaata acaactctaa   2700
ctatcaaaac aaaaacagct aattaaattg caaatcagt cgctaattcc tagtcactaa    2760
tcactgttca cagcaaaaca ccaactgaat cagtcgctaa acagtcgcta acaggagac    2820
gcaactgaaa tgcaaaacag aatgctacac aaaacaaaac aactaaacac tattatgaac   2880
ctttggccca ctgctccccg acaacgcgc caaatttgat cgaggtcgta cccgaatcaa   2940
ataaacatta aaaatgcagt atctaggaag tgatcctagg tcatctccca acgagcaatg   3000
gtcaaccaat gttcataata gatagtgata aacaataac gaattggggg ggggggtat    3060
ttgttttttgt aatttaaaca acaagcaaat tttaattaga aaataacaga attaaaacat   3120
gttattttccc cttgattcat aagcaagtct cttatcctag gttaggagga tttatcccta   3180
accagttcaa cccacttaatc caaccctaaa ttaaattact aagcgaaaat taacataagg   3240
ttgtctttat atgattaagc aacacataca ccaattaatc atgaacaaaa tcgatcatta   3300
agcatcaaca taaattaagc gcaaagataa ttaatcaagc actaagcatg catggattag   3360
tagcaacaaa tacagagtaa ttggtggaga tgaaaaactg atcaatattc aatagtaata   3420
acaaaacctc aaagagagtt gtgcttgatt ctcaagagaa aacaacgctg gagacttagc   3480
cttccattaa tcagtagaaa acgaaattgt agaaaacgaa ttttattcta tgtgaacaat   3540
gtgcatgaac agtaataaaa actggaattg caaaacccta aaattattct tctctccaaa   3600
aaaactccct aaactaaaac cctggtgcta ttatatagt cctcagcccc aaagcttaa    3660
aatctatttt cagtccaaac ccataaacga aataaaata aatctggaca agataagata   3720
agattggatg aaataaaatc tggacgaaat aaaatctgga taagataaga tttgataaaa   3780
taaaattgtc tgctctttc aagtccaagc ccaattccgg attcaagccc aattttttat   3840
aattcttctg aaatttaaatt aaaaatacga attagtcaa gtaggcccaa atgataaaac   3900
tgcataatta atttgacaat taaggctaat cagtaattaa aatagtgaca aaaagggtta   3960
agaaatagga gaataatgac acatcaccca tatggggagc aattctaaaa tgcatttgag   4020
ttctttaacc tgagacacag tgcagtagag tctccaagga ttcattgtgc cttttatttt   4080
atatgatggg gtcactacat tggccttgtc aaagaaactg aatttgggg attaaagaaa   4140
cacaaaataa aaacaaatga aactagttaa tagaaatgtt gcctattgct tcttggaaa    4200
agtccaacca tttgtgatttt ggataaaatt catattaccc acttgtagct tgttcaatca   4260
aacactagat ttgataaaaa tctcactcct agatatacct caaggggataa tatgaccaac   4320
attagtcatt tttagaaagt aaagtggaca aatttgagat ttcattcctt aatgacatta   4380
taaacatgta ttttttccat gacccttttt caatgtaagt acaatttatc ccttagttta   4440
gatactctat atatgcatgt tacgtagttg atgaaaacat acctaagttg ttgtgtatgg   4500
ttaagtttgc gactacctct gatatcaaac tcctcatctc caatctcata caaaagatac   4560
ttgtcacttg gtacctgaac cttgtcagtt tgcagttgtg agtttcttct gaagccacac   4620
gcttgtatag taaccagaag ccaggaggga gtcctcaag gctctaactc gtattttccg   4680
tggaagtaca ttttttttct taaagaaaac agagatagtt taccaatgat aatatttctt   4740
tagccaaata ggaccatcat agaaaacaaa actcttcttc taagtattta atgcaactac   4800
atatttaggg tgcgtttgat tcgctaaaaa ataagggtct agacaacaca aaaatatttt   4860
tccaacgttt gattttaaaa atggctgaga gacaatacaa aataaagaat gatgaactgg   4920
acaaaaacct aaaaacttgt aactcactga atctcataca acttttttgtt cagtgtctaa   4980
aaaaagtaaa aatacaatat tattcctatt ttttacttttg attatctcac accttctttc   5040
tactcatttg tttcacttca cctctccagt gggcaccttg gtttgtcggc gagagtcgta   5100
tggacttttg ttgttccctt tttgctcatt atttcttttct tttcattgtt aatttattca   5160
aatgttccca tcatcatctt actccttctt gttatgtttt ttttcttggg ccaactccaa   5220
cgaggccgtg ccgcgaccac catcatcacg acctatggc ggcctcacgc cgcaaggccc   5280
tgcacccagt ggcatcaggg gtcatgcctc cttcttaaag gtgtctctct tttgttatgt   5340
```

```
cgtcaaagtg ttgctaattc acctagaatt tttcaatgaa tcccttttact tgtgggttag   5400
tctaggtcgc tctgcccggt tccaacccta gcccaaaaaa aaatgaaatg ggtaggaaag   5460
gcgggcctag tttgaattaa aataaatcat gctaagatat tgataactgc tatgtatagg   5520
tatattttgg gattaaatta tataggaatt agtaattttt ctctcttatt tcttcctttt   5580
tgttcaaata attggaattc taacatcatt taagttttta tgtagaaaat attaaaagtt   5640
gatgaattta tgatacttag tgaataatta gagtagaaaa ataaagtaaa gcccaaaaaa   5700
gaaaattggt gatatgaaga tacatgctta gcatgcccca ggcacgctta gtttcctaaa   5760
ttagtcctac ttttttgatgt caaacactga tagtttaaac tgaaggcggg aaacgacaat   5820
ctgatcccca tcaagcttga tatcgaattc ctgcagcccg ggggatccac tagttctaga   5880
gcggccgcgt taactgcagg tcgacggatc cccgggtacc gagctcgaat tcaaatttat   5940
tatgtgtttt ttttccgtgg tcgagattgt gtattattct ttagttatta caagactttt   6000
agctaaaatt tgaaagaatt tactttaaga aatcttaac atctgagata atttcagcaa    6060
tagattatat ttttcattac tctagcagta tttttgcaga tcaatcgcaa catatatggt   6120
tgttagaaaa aatgcactat atatatatat attattttt caattaaaag tgcatgatat    6180
ataatatata tatatatata tatgtgtgtg tgtatatggt caaagaaatt cttatacaaa   6240
tatacacgaa cacatatatt tgacaaaatc aaagtattac actaaacaat gagttggtgc   6300
atggccaaaa caaatatgta gattaaaaat tccagcctcc aaaaaaaaat ccaagtgttg   6360
taaagcatta tatatatata gtagatccca aattttttgta caattccaca ctgatcgaat   6420
ttttaaagtt gaatatctga cgtaggattt ttttaatgtc ttacctgacc atttactaat   6480
aacattcata cgtttttcatt tgaaatatcc tctataatta tattgaattt ggcacataat   6540
aagaaaccta attggtgatt tattttacta gtaaatttc ggtgatgggc tttctactag    6600
aaagctctcg gaaaatcttg gaccaaatcc atattccatg acttcgattg ttaaccctat   6660
tagttttcac aaacatacta tcaatatcat tgcaacggaa aaggtacaag taaaacattc   6720
aatccgatag ggaagtgatg tagggggttg ggaagacagg cccagaaaga gatttatctg   6780
acttgttttg tgtatagttt tcaatgttca taaggaaga tggagacttg agaagttttt    6840
tttggactttt gtttagcttt gttgggcgtt ttttttttttg atcaataact ttgttgggct   6900
tatgatttgt aatattttcg tggactcttt agtttattta gacgtgctaa ctttgttggg   6960
cttatgactt gttgtaacat attgtaacag atgacttgat gtgcgactaa tctttacaca   7020
ttaaacatag ttctgttttt tgaaagttct tattttcatt tttatttgaa tgttatatat   7080
ttttctatat ttataattct agtaaaaggc aaattttgct tttaaatgaa aaaatatat    7140
attccacagt ttcacctaat cttatgcatt tagcagtaca aattcaaaaa tttcccattt   7200
ttattcatga atcataccat tatatattaa ctaaatccaa ggtaaaaaaa aggtatgaaa   7260
gctctatagt aagtaaaata taaattcccc ataaggaaag ggccaagtcc accaggcaag   7320
taaaatgagc aagcaccact ccaccatcac acaatttcac tcatagataa cgataagatt   7380
catggaatta tcttccacgt ggcattattc cagcggttca agccgataag ggtctcaaca   7440
cctctcctta ggcctttgtg gccgttacca agtaaaatta acctcacaca tatccacact   7500
caaaatccaa cggtgtagat cctagtccac ttgaatctca tgtatcctag accctccgat   7560
cactccaaag cttgttctca ttgttgttat cattatatat agatgaccaa agcactagac   7620
caaacctcag tcacacaaag agtaaagaag aacaatgact tcctcctatgc tctcttccgc   7680
tactatggtt gcctctccgg ctcaggccac catggtcgct cctttcaacg gacttaagtc   7740
ctccgctgcc ttcccagcca cccgcaaggc taacaacgac attacttcca tcacaagcaa   7800
cggcggaaga gttaactgca tgcaggtgtg gcctccgatt ggaaagaaga gtttgagac    7860
tctctcttac cttcctgacc ttaccgattc cggtggtcgc tcaactgca tgcaggccat    7920
ggacaacaac ccaaacatca acgaatgcat tccatacaac tgcttgagta acccagaagt   7980
tgaagtactt ggtggagaac gcattgaaac cggttacact cccatcgaca tctccttgtc   8040
cttgacacag tttctgctca gcgagttcgt gccaggtgct gggttcgttc tcggactagt   8100
tgacatcatc tggggtatct ttggtccatc tcaatggcat gcattcctgg tgcaaattga   8160
gcagttgatc aaccagagga tcgaagagtt cgccaggaac caggccatct ctaggttgga   8220
aggattgagc aatctctacc aaatctatgc agagagcttc agagagtggg aagccgatcc   8280
tactaaccca gctctccgcg aggaaatgcg tattcaattc aacgacatga acagcgcctt   8340
gaccacagct atcccattgt tcgcagtcca gaactaccaa gttcctctct tgtccgtgta   8400
cgttcaagca gctaatcttc acctcagcgt gcttcgagac gttagcgtgt ttgggcaaag   8460
gtggggattc gatgctgcaa ccatcaatag ccgttacaac gaccttacta ggctgattgg   8520
aaactacacc gaccacgctg ttcgttggta caacactggc ttggagcgtg tctgggtcc    8580
tgattctaga gattggatta gatacaacca gttcaggaga gaattgaccc tcacagtttt   8640
ggacattgtg tctctcttcc cgaactatga ctccagaacc tacccctatcc gtacagtgtc   8700
ccaacttacc agagaaatct atactaaccc agttcttgag aacttcgacg gtagcttccg   8760
tggttctgcc caaggtatcg aaggctccat caggagccca cacttgatgg acatcttgaa   8820
cagcataact atctacaccg atgctcacag aggagagtat tactggtctg gacaccagat   8880
catggcctct ccagtggat tcagcgggcc cgagtttacc tttcctctct atggaactat    8940
gggaaacgcc gctccacaac aacgtatcgt tgctcaacta ggtcagggtg tctacagaac   9000
cttgtcttcc accttgtaca gaagaccctt caatatcggt atcaacaacc agcaactttc   9060
cgttcttgac ggaacagagt tcgcctatgg aacctcttct aacttgccat ccgctgttta   9120
cagaaagagc ggaaccgttg attccttgga cgaaatccca ccacagaaca acaatgtgcc   9180
acccaggcaa ggattctccc acaggttgag ccacgtgtcc atgttccgtt ccggattcag   9240
caacagttcc gtgagcatca tcagagctcc tatgttctct tggatacatc gtagtgctga   9300
gttcaacaac atcatcgcat ccgatagtat tactcaaatc cctgcagtga agggaaactt   9360
tctcttcaac ggttctgtca tttcaggacc aggattcact ggtggagaca tcgttagact   9420
caacagcagt ggaaataaca ttcagaatag agggtatatt gaagttccaa ttcacttcca   9480
atccacatct accagatata gagttcgtgt gaggtatgct tctgtgaccc ctattccct    9540
caacgttaat tgggggtaatt catccatctt ctccaataca gttccagcta cagctaccte   9600
cttgataaat ctccaatcca gcgatttcgg ttactttgaa agtgccaatg cttttacatc   9660
ttcactcggt aacatcgtgg gtgttagaaa ctttagtggg actgcaggag tgattatcga   9720
cagattcgag ttcattccag ttactgcaac actcgaggct gagtacaacc ttgagagagc   9780
ccagaaggct gtgaacgccc tctttacctc caccaatcag cttggcttga aaactaacgt   9840
tactgactat cacattgacc aagtgtccaa cttggtcacc taccttagcg atgagttctg   9900
cctcgacgag aagcgtgaac tctccgagaa agttaaacac gccaagcgtc tcagcgacga   9960
gaggaatctc ttgcaagact ccaacttcaa agacatcaac aggcagccag aacgtggttg  10020
gggtggaagc accgggatca ccatccaagg aggcgacgat gtgttcaagg agaactacgt  10080
```

```
caccctctcc ggaactttcg acgagtgcta ccctacctac ttgtaccaga agatcgatga    10140
gtccaaactc aaagccttca ccaggtatca acttagaggc tacatcgaag acagccaaga    10200
ccttgaaatc tactcgatca ggtacaatgc caagcacgag accgtgaatg tcccaggtac    10260
tggttccctc tggccacttt ctgcccaatc tcccattggg aagtgtggag agcctaacag    10320
atgcgctcca caccttgagt ggaatcctga cttggactgg tcctgcaggg atggcgagaa    10380
gtgtgcccac cattctcatc acttctcctt ggacatcgat gtgggatgta ctgacctgaa    10440
tgaggacctc ggagtctggg tcatcttcaa gatcaagacc caagacggac acgcaagact    10500
tggcaacctt gagtttctcg aagagaaacc attggtcggt gaagctctcg ctcgtgtgaa    10560
gagagcagag aagaagtgga gggacaaacg tgagaaactc taagtgggaaa ctaacatcgt    10620
ttacaaggag gccaaagagt ccgtggatgc tttgttcgtg aactcccaat atgatcagtt    10680
gcaagccgac accaacatcg ccatgatcca cgccgcagac aaacgtgtgc acagcattcg    10740
tgaggcttac ttgcctgagt tgtccgtgat ccctggtgtg aacgctgcca tcttcgagga    10800
acttgaggga cgtatcttta ccgcattctc cttgtacgat gccagaaacg tcatcaagaa    10860
cggtgacttc aacaatggcc tcagctgctg gaatgtgaaa ggtcatgtgg acgtgggaga    10920
acagaacaat cagcgttccg tcctggttgt gcctgagtgg gaagctgaag tgtcccaaga    10980
ggttagagtc tgtccaggta gaggctacat tctccgtgtg accgcttaca aggagggata    11040
cggtgagggt tgcgtgacca tccacgagat cgagaacaac accgacgagc ttaagttctc    11100
caactgcgtc gaggaagaaa tctatcccaa caacaccgtt acttgcaacg actacactgt    11160
gaatcaggaa gagtacggag gtgcctacac tagccgtaac agaggttaca acgaagctcc    11220
ttccgttcct gctgactatg cctccgtgta cgaggagaaa tcctacacag atggcagacg    11280
tgagaaccct tgcgagttca acagaggtta cagggactac acaccactcc cagttggcta    11340
tgttaccaag gagcttgagt acttttcctga gaccgacaaa ggtgtggatcg agatcggtga    11400
aaccgaggga accttcatcg tggacagcgt ggagcttctc ttgatggagg aataatgaga    11460
tcccgtcctt tgtcttcaat tttgagggct ttttactgaa taagtatgta gtactaaaat    11520
gtatgctgta atagctcata gtgagcgagg aaagtatcgg gctatttaac tatgacttga    11580
gctccatcta tgaataaata aatcgaatca tgatgctttt gttttgtgta cttcaactgt    11640
ctgcttagct aatttgatat ggttggcact tggcacgtat aaatatgctg aagtaattta    11700
ctctgaagct aaattaacta gattagatga gtgtattata tacaaaaggc attaaatcag    11760
atacatctta gacaaattgt cacggtctac cagaaaagaa attgcatttg tttttgggtc    11820
tttcagactg acaagatcga tctgaagtct aaacaattcc aagaggtatc atgtagcaat    11880
gtcctgccac aatattgaat tgacctgcag cccgggcggc cgcatcgatc gtgaagtttc    11940
tcatctcaagc ccccatttgg acgtgaatgt agacacgtcg aaataaagat ttccgaatta    12000
gaataatttg tttattgctt tcgcctataa atacgacgga tcgtaatttg tcgttttatc    12060
aaaatgtact ttcatttat aataacgctg cggacatcta catttttgaa ttgaaaaaaa    12120
attggtaatt actctcttctt tttctccata ttgaccatca tactcattgc tgatccatgt    12180
agatttcccg gacatgaagc catcaaaaag taggactaat ttaggaaagc aagctaattc    12240
aagaaagtga aggcacgctt agtgtgagac acgtgttgag cgcgattact gccactcact    12300
aaccacacaa gtgcactcag tgcgaaggtt gcttaaaaat taagttgatt cgcacttata    12360
aaagaaggat agagatgaag gaaaaaaaac agaaaataca attccttata gaagacaaag    12420
gctagaagaa gcaaacgcaa acattagaag tcattccttc cctcaattcc cttttttcaat    12480
ttccccttt actaaatatt ctcctcttgc aattataaag cctcctatga caatgacaag    12540
ctaaactctc ctttgttggg aacttatcag tcaactgctc ttaatataat ttctcttcct    12600
atctattatg aatattcact acaagaaata tgcccattcc tcagggattt ttgacaggga    12660
cattaacccc tggcaaattt cccagggact aagccaagga aacccctggc aaaatgacat    12720
ttgagaaggc tgggaccact tacatttaca caggggtttg tccctcgcaa aaatacaaaa    12780
gccttggcaa aaaaaagagc gggaaatgaa ttttaaaaca gcatgttgtt ttcacacagc    12840
caaacacacg ggtatgccct cgttttctgt aaagctgacg gaatcttccc ataagtcaac    12900
acgacatgac catgcactgc aaaaagctgt gcggcccaga cgtgacaggg gtgttacccc    12960
tcggaaatgg cttgcagccc ctggcaaaaa ggaatccctg ctttcctagc tacaccgttc    13020
tgctcatata gctgaagcta ggaggttagc ctttgactct gttgttttgc gaggggcatt    13080
ccgtgagtta ttccctgggt tttttttacac tatatagcca aaccgcgtgt ttatcctcat    13140
gctcagtgtt gtgtttttga aacttagaaa aattttcggt ttccattttcc atcctcacca    13200
gttcattttc agtccattat cattcagttc atacacttgt tctataattt ggtaacactc    13260
ttttcactta ttatatttt ctgttttat ttgttactac ttattaacat aaatattttt    13320
tattgtatca gtgtccaaat ttgcctcctc ctgctgctcc ttgctctctg aatttgttct    13380
cttaagcttc aacaagttag taatttttct acttataatt ttagatatat gatgtttata    13440
tatatgatgt tataatttg catgatctgt caaagaaaat atgatgtttc tacttgcatg    13500
atgtgttata atatatgatg tttatatata tttcgaattt tgttgttaat aaaactgttt    13560
aattagaaac tgtataattt ttttgtttaa taaaactgtt taattttgca tgatctgttt    13620
aataaaactg tttatataaa actgtttata tataatatat gatgttaaca ttttttaaaac    13680
tgtttataaa acagtttagt tagaaaaaat gttaaaacta gagaaaaaaa tgtataataa    13740
aactgtgtca gtacagcagc gcgtcagaaa agtgtgcaga tgcgtcagtg agaagacagg    13800
ggctaagaca gggattttga cagggaattt tgccaggat tttgccaggg tcagcccctg    13860
gttttttgc cagggtgaa atccctggca aactgatttg cgatgggtt ttttccagg    13920
gattcagccc ctggcaaaat ccctggcaaa cgtccatttc ccagggcttt tgttctcttt    13980
cccagggaat ccgccctgg caaacgagct tgtttcttgt agtgattact tttgcattag    14040
ttttttcctgt atttaattt attgtttatg gcttgattac ccatttgcat tataagtttt    14100
aggggtagcg ttgaaaagtg ttattctcta atagaactgg aaaagagtat ttaaataact    14160
tcatcactag ggatacattg atttattta gcttattata tatctctatt attaatgtaa    14220
tttaactatt ttatctctgc aaagtgattt gggagagaag atagataagt tagactcttt    14280
cactcgaggc tgagtacaac cttgagagag cccagaaggc tgtgaacgcc ctctttacct    14340
ccaccaatca gcttggcttg aaaactaacg ttactgacta tcacattgac caagtgtcca    14400
acttggtcac ctaccttagc gatgagttct gaaggg                              14436
```

SEQ ID NO: 16      moltype = AA  length = 1307
FEATURE              Location/Qualifiers
source               1..1307
                     mol_type = protein
                     organism = unidentified

```
SEQUENCE: 16
MTQFEGFTNL  YQVSKTLRFE  LIPQGKTLKH  IQEQGFIEED  KARNDHYKEL  KPIIDRIYKT   60
YADQCLQLVQ  LDWENLSAAI  DSYRKEKTEE  TRNALIEEQA  TYRNAIHDYF  IGRTDNLTDA  120
INKRHAEIYK  GLFKAELFNG  KVLKQLGTVT  TTEHENALLR  SFDKFTTYFS  GFYENRKNVF  180
SAEDISTAIP  HRIVQDNFPK  FKENCHIFTR  LITAVPSLRE  HPENVKKAIG  IFVSTSIEEV  240
FSFPFYNQLL  TQTQIDLYNQ  LLGGISREAG  TEKIKGLNEV  LNLAIQKNDE  TAHIIASLPH  300
RFIPLFKQIL  SDRNTLSFIL  EEFKSDEEVI  QSFCKYKTLL  RNENVLETAE  ALFNELNSID  360
LTHIFISHKK  LETISSALCD  HWDTLRNALY  ERRISELTGK  ITKSAKEKVQ  RSLKHEDINL  420
QEIISAAGKE  LSEAFKQKTS  EILSHAHAAL  DQPLPTTLKK  QEEKEILKSQ  LDSLLGLYHL  480
LDWFAVDESN  EVDPEFSARL  TGIKLEMEPS  LSFYNKARNY  ATKKPYSVEK  FKLNFQMPTL  540
ASGWDVNKEK  NNGAILFVKN  GLYYLGIMPK  QKGRYKALSF  EPTEKTSEGF  DKMYYDYFPD  600
AAKMIPKCST  QLKAVTAHFQ  THTTPILLSN  NFIEPLEITK  EIYDLNNPEK  EPKKFQTAYA  660
KKTGDQKGYR  EALCKWIDFT  RDFLSKYTKT  TSIDLSSLRP  SSQYKDLGEY  YAELNPLLYH  720
ISFQRIAEKE  IMDAVETGKL  YLFQIYNKDF  AKGHHGKPNL  HTLYWTGLFS  PENLAKTSIK  780
LNGQAELFYR  PKSRMKRMAH  RLGEKMLNKK  LKDQKTPIPD  TLYQELYDYV  NHRLSHDLSD  840
EARALLPNVI  TKEVSHEIIK  DRRFTSDKFF  FHVPITLNYQ  AANSPSKFNQ  RVNAYLKEHP  900
ETPIIGIDRG  ERNLIYITVI  DSTGKILEQR  SLNTIQQFDY  QKKLDNREKE  RVAARQAWSV  960
VGTIKDLKQG  YLSQVIHEIV  DLMIHYQAVV  VLENLNFGFK  SKRTGIAEKA  VYQQFEKMLI 1020
DKLNCLVLKD  YPAEKVGGVL  NPYQLTDQFT  SFAKMGTQSG  FLFYVPAPYT  SKIDPLTGFV 1080
DPFVWKTIKN  HESRKHFLEG  FDFLHYDVKT  GDFILHFKMN  RNLSFQRGLP  GFMPAWDIVF 1140
EKNETQFDAK  GTPFIAGKRI  VPVIENHRFT  GRYRDLYPAN  ELIALLEEKG  IVFRDGSNIL 1200
PKLLENDDSH  AIDTMVALIR  SVLQMRNSNA  ATGEDYINSP  VRDLNGVCFD  SRFQNPEWPM 1260
DADANGAYHI  ALKGQLLLNH  LKESKDLKLQ  NGISNQDWLA  YIQELRN               1307

SEQ ID NO: 17           moltype = DNA  length = 40
FEATURE                 Location/Qualifiers
source                  1..40
                        mol_type = other DNA
                        organism = synthetic construct
SEQUENCE: 17
ccaggcacgc ttagtgtgtg tgtcaaacac tgatagttta                                40

SEQ ID NO: 18           moltype = DNA  length = 5757
FEATURE                 Location/Qualifiers
source                  1..5757
                        mol_type = other DNA
                        organism = synthetic construct
SEQUENCE: 18
gggaaaatcc ctcttccata ttaagaacat aaaaatcaac aggaaaaata agttcaccaa    60
cccgaaccag cacatcctct atgaaacctg cggggtaagc agcacttcta ttttccaaat   120
gaatcaccac atctgtagat tgcaaaggtc caagagataa agaattgaaa atggacagag   180
gggtgacact aactgatgct cctagatcta gcattgtatt atcaaattta ctgttcccaa   240
taatgcaagg tatacagaaa gtacctgggt ccttacattc ctcagaatg taaggaacaa   300
atttacctat caatgctgac acatttctgc ccatgctaat cctttcattg cctttgagct   360
tccttttgtg ggtgcacaac tcctttagaa acttgacaca tcttggaatc tgcttgatgg   420
catctagcag aggtatgttc acctctactt tcctgaaggt ctccaagatc tccttttctg   480
cttcttccat ttttttttgtt tggaattgct caaggttgga atggaagagg gataagaggc   540
tgcggtaagt cagaattact agaagaaggt ccacctgcat gaaaatttt gttaggaagc   600
tttctctttt gtgcaactat ctcatcctct ttttcaggtg tagaatgaag cttgacaggt   660
tcaggtgcgg gtgctgctac tggtggaggt acttgaattt ggttgtcaga cctcaaggtg   720
atgacactca cattttttcgg attttgcaca gtttgtgaag gcaatttgtc agaattttgg   780
gaatgagctt ggttcaactg agtagccatc cgccccatct gattgtcag actctgaatg   840
aaggctcttg tctcttgctg aaattgcata ttctggatgg tcatttgcct cactaactct   900
tctaaggaag gttaaggagg agtctcagtt gcttgttgtc tttgttgtga ctgttgttgt   960
tgttgctgct gtattggagg aggaaacatat ggtttgcttg gaccagcaac attctggaaa  1020
ggagggacag actgttgttg ttgtgaagga cttgcccatc tcatatttgg atgatttctc  1080
caacctggat tgtatctgtt gcttggaaga tcataattat tttgctattg ttggttttgc  1140
tgttgagggg gtctattata aatgtttgca gcataagctt caggttgttc attgactcca  1200
gattactgca aagaaggaca aagatctgta tggtgatctg cagaagaaca tataccacag  1260
actcttgtaa caggtgcaaa tttctgattc atggcaagct gagttactag gttgaccaag  1320
gcatcaagtt ttccctcaag cttttttattt tcagtagata aagatgaatc tgtggccacc  1380
tcatcgactc ctctaaggac aatagcatca tttcttgcac tgaattgttg ggagttggaa  1440
gccttcttct caatcaaatt cctagcctca gcagggtgtca tatcacgaag agctccacca  1500
ctggcagcat caatcatact cctctccatg ttgctaagtc cctcatagaa atattgaaga  1560
aggagttgct cagaaatctg gtggtgagga cagcttgcac acaatttctt gaatcttct  1620
cagtactcat acaagctctc tccactaagt tgcctgatgc ctgaaattc ttttctgatg  1680
gcagtggtcc tagatgcagg gaagaatttc tccaagaaca cccctcttaag gtcatcccag  1740
ctgaaaatgg acctgggagc aaggtagtag agccaatct ttgtcactac ctccagagaa  1800
tgaggaaaag cctttagaaa gatatgatct tcttggacat caggggcgtt catggtggta  1860
caaacaatat ggaactcctt aagatgctta tgaggatctt cacctagaag accatgaaac  1920
ttgggtagca aatgtattag tccagtcttg agaacatatg gaacccctc atcaggatat  1980
tgaatgcaca agttttcata agtgaaatca ggtgcagcca tctccctaag agtcctctca  2040
cgaggtggag gtttagccat gttctcagta tgaaattag tagttaatg ctcaaaatca  2100
gaattccag aatcaccaga aacaaaatac tcagaatgct caaaatgctc aaaatgaaag  2160
taatgattag gatgcacact atgcctaact aatctatgaa aggttctatc tatttcagga  2220
tcgaaggggtt ataaatcacc tagattgccc ctagtcatgc actatatgta gcaaataatg  2280
tgttctcaaa caagcaccaa gggagggtta aaactacaac tatagtcaaa tgatatccaa  2340
atgagttgaa attttgtgag cagcacccta aaatcatgaa agatagcac aaaaaatttc  2400
aaacgaaaat tcaaagtcta actatgaaaa ctacttaaga aagtttaga aaaataggac  2460
```

-continued

```
aataatactt gaaaaataaa aaaaaacata gtaaacagct gattttttcga gtttgggaga    2520
ctccaaccgg ctaaaacggg ttgccacaat atgagaaatt ttttttctacc ccaaatgcca    2580
caatatgaga aagttttgct aaaatctagt tcccaaaatt tttgtctctc tcaaattcaa    2640
ccacaccaag tgctcctagt atttttcaca caaaaaatca gccaaaaata caactctaaa    2700
ctatcaaaac aaaaacagct aattaaattg caaaatcagt cgctaattcc tagtcactaa    2760
tcactgttca cagcaaaaca ccaactgaat cagtcgctaa acagtcgcta aacaggagac    2820
gcaactgaaa tgcaaaacag aatgctacac aaaacaaaac aactaaacac tattatgaac    2880
ctttggccca ctgctccccg caacggcgc caaatttgat cgaggtcgta cccgaatcaa    2940
ataaacatta aaaatgcagt atctaggaag tgatcctagg tcatctccca acgagcaatg    3000
gtcaaccaat gttcataata gatagtgata aaacaataac gaattggggg ggggggtat    3060
ttgttttttgt aatttaaaca acaagcaaat tttaattaga aaataacaga attaaaacat    3120
gttatttccc cttgattcat aagcaagtct cttatcctag gttaggagga tttatccctta    3180
accagttcaa ccacttaatc caaccctaaa ttaaattact aagcgaaaat taacataagg    3240
ttgtctttat atgattaagc aacacataca ccaattaatc atgaacaaaa tcgatcatta    3300
agcatcaaca taaattaagc gcaaagataa ttaatcaagc actaagcatg catggattag    3360
tagcaacaaa tacagagtaa ttggtggaga tgaaaaactg atcaatattc aatagtaata    3420
acaaaacctc aaagagagtt gtgcttgatt ctcaagagaa aacaacgctg gagacttagc    3480
cttccattaa tcagtagaaa acgaaattgt agaaaacgaa ttttattcta tgtgaacaat    3540
gtgcatgaac agtaataaaa actgaattgc aaaaccccta aaattattct tctctctcaaa    3600
aaaactccct aaactaaaac cctggtgcta ttatataggt ccctcagcccc aaagcttaca    3660
aatctatttt cagtccaaac ccataaacga aataaaataa aatctggaca agataagata    3720
agattggatg aaataaaatc tggacgaaat aaaatctgga taagataaga tttgataaaa    3780
taaaattgtc tgctcttttttc aagtccaagc ccaattccgg attcaagccc aattttttat    3840
aattcttctg aaatttaaatt aaaaatacga aattagtcaa gtaggccaa atgataaaac    3900
tgcataatta atttgacaat taaggctaat cagtaattaa aatagtgaca aaaagggtta    3960
agaaatagga gaataatgac acatcaccca tatgggaagc aattctaaaa tgcatttgag    4020
ttctttaacc tgagacacag tgcagtagag tctccaagga ttcattgtgc cttttatttt    4080
atatgatggg gtcactacat tggccttgtc aaagaaactg aatttggggg attaaagaaa    4140
cacaaaataa aaacaaatga aactagttaa tagaaatgtt gcctattgct tcttggaaaa    4200
agtccaacca tttgtgattt ggataaaatt catattcaatcca acttgtagct tgttcaatca    4260
aacactagat ttggataaaa tctcactcct agatatacct caaggggataa tatgaccaac    4320
attagtcatt tttagaaagt aaagtggaca aatttgagat ttcattcctt aatgacatta    4380
taaacatgta tttttttccat gacccttttt caatgtaagt acaatttatc ccttagttta    4440
gatactctat atatgcatgt tacgtagttg atgaaaacat acctaagttg ttgtgtatgg    4500
ttaagtttgc gactacctct gatatcaaac tcctcatctc caatctcata caaaagatac    4560
ttgtcacttg gtacctgaac cttgtcagtt tgcagttgtg agtttcttct gaagccacac    4620
gcttgtatag taaccagaag ccaggaggga gtccctaag gctctaactc gtattttccg    4680
tggaagtaca tttttttttct taaagaaaac agagatagtt taccaatgat aatatttctt    4740
tagccaaata ggaccatcat agaaaacaaa actcttcttc taagtattta atgcaactac    4800
atatttaggg tgcgtttgat tcgctaaaaa ataggggtct agacaacaca aaaatatttt    4860
tccaacgttt gatttttaaaa atggctgaga gacaatacaa aataaagaat gatgaactgg    4920
acaaaaacct aaaacttgt aactcactga atctcataca actttttgtt cagtgtctaa    4980
aaaaagtaaa atacaatat tattcctatt tttttacttttg attatctcac acccttcttttc    5040
tactcatttg tttcacttca cctctccagt gggcaccttg gtttgtcggc gagagtcgta    5100
tggacttttg ttgtttcctt tttgctcatt atttctttct tttcattgtt aatttattca    5160
aatgttccca tcatcatctt actccttctt gttatgtttt ttttctttgg ccaactccaa    5220
cgaggccgtg ccgcgaccac catcatcacg accttatggc ggcctcacgc cgcaaggccc    5280
tgcacccagt ggcatcaggg gtcatgcctc cttcttaaag gtgtctctct tttgttatgt    5340
cgtcaaagtg ttgctaattc acctagaatt ttttcaatgaa tcccttttact tgtgggttag    5400
tctaggtcgc tctgccggt tccaacccta gcccaaaaaa aaatgaaatg ggtaggaaag    5460
gcgggcctag tttgaattaa aataaatcat gctaagatat tgataactgc tatgtatagg    5520
tatatttttgg gattaaatta tataggaatt agtaattttt ctctcttatt tcttcctttt    5580
tgttcaaata attggaattc taacatcatt taagtttttta tgtagaaaat attaaaagtt    5640
gatgaattta tgatacttag tgaataatta gagtagaaaa ataaagtaaa gcccaaaaaa    5700
gaaaattggt gatatgaaga tacatgctta gcatgccccca ggcacgctta gtgtgtg      5757

SEQ ID NO: 19          moltype = DNA  length = 40
FEATURE                Location/Qualifiers
source                 1..40
                       mol_type = other DNA
                       organism = synthetic construct
SEQUENCE: 19
tttcccggac atgaagccat caaaaagtag gactaattta                            40

SEQ ID NO: 20          moltype = DNA  length = 2233
FEATURE                Location/Qualifiers
source                 1..2233
                       mol_type = other DNA
                       organism = synthetic construct
SEQUENCE: 20
caaaaagtag gactaattta ggaaagcaag ctaattcaag aaagtgaagg cacgcttagt     60
gtgagacacg tgttgagcgc gattactgcc actcactaac cacacaagtg cactcagtgc    120
gaaggttgct taaaattaa gttgattcgc acttataaaa gaaggataga gatgaaggaa    180
aaaacagaaaagcaatt cctttataga gacaaaggct agaagaagca aacgcaaaca       240
ttagaagtca ttccttccct caattccctt tttcaatttc cccttttact aaatattctc    300
ctcttgcaat tataaagcct cctatgacaa tgacaagcta aactctcctt tgttgggaac    360
ttatcagtca actgctctta atataatttc tcttcctatc tattatgaat attcactaca    420
agaaatatgc ccatttgcca gggatttttg acagggacat taaccctgg caaatttccc    480
agggactaag ccaaggaaac ccctggcaaa atgacatttg agaaggctgg gaccacttac    540
```

```
atttacacag gggtttgtcc ctcgcaaaaa tacaaaagcc ttggcaaaaa aaagagcggg    600
aaatgaattt taaaacagca tgttgttttc acacagccaa acacacgggt atgccctcgt    660
tttctgtaaa gctgacggaa tcttcccata agtcaacacg acatgaccat gcactgcaaa    720
aagctgtgcg gcccagacgt gacaggggtg ttaccactcg gaaatggctt gcagccctg    780
gcaaaaagga atccctgctt tcctagctac accgttctgc tcatatagct gaagctagga    840
ggttagcctt tgactctgtt gttttgcgag gggcattccg tgagttattc cctgggtttt    900
tttacactat atagccaaac cgcgtgttta tcctcatgct cagtgttgtg tttttgaaac    960
ttagaaaaat tttcggtttc catttccatc ctcaccagtt catttcagt ccattatcat   1020
tcagttcata cacttgttct ataatttggt aacactcttt tcacttatta tatttttctg   1080
tttttatttg ttactactta ttaacataaa tatttttat tgtatcagtg tccaaatttg   1140
cctcctcctg ctgctccttg ctctctgaat ttgttctctt aagcttcaac aagttagtaa   1200
tttttctact tataatttta gatatatgat gtttatatat atgatgttat aattttgcat   1260
gatctgtcaa agaaaatatg atgtttctac ttgcatgatg tgttataata tatgatgttt   1320
atatatattt cgaattttgt tgttaataaa actgtttaat tagaaactgt ataatttttt   1380
tgtttaataa aactgtttaa ttttgcatga tctgtttaat aaaactgttt atataaaact   1440
gtttatatat aatatatgat gttaacattt ttaaaactgt ttataaaaca gtttagttag   1500
aaaaaatgtt aaaactagag aaaaaaatgt ataataaaac tgtgtcagta cagcagcgcg   1560
tcagaaaagt gtgcagatgc gtcagtgaga agacaggggc taagacaggg attttgacag   1620
ggaattttgc cagggatttt gccagggtca gcccctcgtt tttttgccag gggtgaaatc   1680
cctggcaaac tgatttgcga tgggcgtttt tcccagggat tcagccctg gcaaaatccc   1740
tggcaaacgt ccatttccca gggcttttg ttcttttccc agggaatccg ccctggcaa   1800
acgagcttgt ttcttgtagt gattactttt gcattagttt ttcctgtatt taatttattt   1860
gtttatggct tgattaccca tttgcattat aagttttagg ggtagcgttg aaaagtgtta   1920
ttctctaata gaactggaaa agagtattta aataactcca tcactaggga tacattgatt   1980
ttatttagct tattatatat ctctattatt aatgtaattt aactatttta tctctgcaaa   2040
gtgattttggg agagaagata gataagttag actctttcac tcgaggctga gtacaacctt   2100
gagagagccc agaaggctgt gaacgccctc tttacctcca ccaatcagct tggcttgaaa   2160
actaacgtta ctgactatca cattgaccaa gtgtccaact tggtcaccta ccttagcgat   2220
gagttctgaa ggg                                                      2233

SEQ ID NO: 21           moltype = DNA   length = 1127
FEATURE                 Location/Qualifiers
source                  1..1127
                        mol_type = other DNA
                        organism = synthetic construct
SEQUENCE: 21
tttctttggc caactccaac gaggccgtgc cgcgaccacc atcatcacga ccttatggcg     60
gcctcacgcc gcaaggccct gcacccagtg gcatcagggg tcatgcctcc ttcttaaagg    120
tgtctctctt ttgttatgtc gtcaaagtgt tgctaattca cctagaattt ttcaatgaat    180
ccctttactt gtgggttagt ctaggtcgct ctgcccggtt ccaaccctag cccaaaaaaa    240
aatgaaatgg gtaggaaagg cgggcctagt ttgaattaaa ataaatcatg ctaagatatt    300
gataactgct atgtataggt atattttggg attaaattat ataggaatta gtaatttttc    360
tctcttattt cttccttttt gttcaaataa ttggaattct aacatcattt aagtttttat    420
gtagaaaata ttaaaagttg atgaatttat gatacttagt gaataattag agtagaaaaa    480
taaagtaaag cccaaaaaag aaaattggtg atatgaagat acatgcttag catgccccag    540
gcacgcttag tgtgtgtgtc aaactttcct aaattagtcc tacttttttga tgtttaaact    600
gaaggcggga aacgacaatc tgatccccat caagcttgat atcgaattcc tgcagcccgg    660
gggatccact agttctagag cggccgcgtt aactgcaggt cgacggatcc ccgggtaccg    720
agctcgaatt caaatttatt atgtgttttt tttccgtggt cgagattgtg tattattctt    780
tagttattac aagactttta gctaaaattt gaaagaattt actttaagaa aatcttaaca    840
tctgagataa tttcagcaat agattatatt tttcattact ctagcagtat tttttgcaat    900
caatcgcaac atatatggtt gttagaaaaa atgcactata tatatatata ttattttttc    960
aattaaaagt gcatgatata taatatatat atatatatat atgtgtgtgt gtatatggtc   1020
aaagaaattc ttatacaaat atacacgaac acatatattt gacaaaatca aagtattaca   1080
ctaaacaatg agttggtgca tggccaaaac aaatatgtag attaaaa                 1127
```

MODIFIED EXCISABLE MON87701 SOYBEAN TRANSGENIC INSECT RESISTANCE LOCUS

CROSS-REFERENCE TO RELATED APPLICATIONS

This is a continuation application of International Application No. PCT/US2021/043,933, filed on Jul. 30, 2021, which claims the benefit of priority to U.S. Provisional Patent Application No. 63/203,137, filed on Jul. 9, 2021, U.S. Provisional Patent Application No. 63/202,569, filed on Jun. 16, 2021, U.S. Provisional Patent Application Nos. 63/201,030 and 63/201,029, filed on Apr. 9, 2021, U.S. Provisional Patent Application Nos. 63/199,951 and 63/199,949, filed on Feb. 4, 2021, U.S. Provisional Patent Application No. 63/199,930, filed on Feb. 3, 2021, and U.S. Provisional Patent Application Nos. 63/059,813, 63/059,860, 63/059,916, and 63/059,963, filed on Jul. 31, 2020, which are each incorporated herein by reference in their entireties.

REFERENCE TO SEQUENCE LISTING SUBMITTED ELECTRONICALLY

The instant application contains a Sequence Listing which has been submitted electronically in XML formatted and is herein incorporated by reference in its entirety. Said XML copy, created on Nov. 18, 2022, is named "P13649US00_SequenceListing.xml" and is 91,553 bytes in size.

BACKGROUND

Transgenes which are placed into different positions in the plant genome through non-site specific integration can exhibit different levels of expression (Weising et al., 1988, Ann. Rev. Genet. 22:421-477). Such transgene insertion sites can also contain various undesirable rearrangements of the foreign DNA elements that include deletions and/or duplications. Furthermore, many transgene insertion sites can also comprise selectable or scoreable marker genes which in some instances are no longer required once a transgenic plant event containing the linked transgenes which confer desirable traits are selected.

Commercial transgenic plants typically comprise one or more independent insertions of transgenes at specific locations in the host plant genome that have been selected for features that include expression of the transgene(s) of interest and the transgene-conferred trait(s), absence or minimization of rearrangements, and normal Mendelian transmission of the trait(s) to progeny. An example of a selected transgenic soybean event which confers resistance to lepidopteran insects is the MON87701 transgenic soybean event disclosed in U.S. Pat. No. 8,049,071. MON87701 transgenic soybean plants express a Cry1Ac protein which confers resistance to lepidopteran insects which include Velvetbean caterpillar (*Anticarsia gemmatalis*), Soybean looper (*Pseudoplusia includens*), Soybean axil borer (*Epinotia aporema*), Yellow Bear Moth (*Spilosoma virginica*), Corn earworm (*Helicoverpa zea*), Fall armyworm (*Spodoptera frugiperda*), and Sunflower looper (*Rachiplusia nu*).

Methods for removing selectable marker genes and/or duplicated transgenes in transgene insertion sites in plant genomes involving use of site-specific recombinase systems (e.g., cre-lox) as well as for insertion of new genes into transgene insertion sites have been disclosed (Srivastava and Ow; Methods Mol Biol, 2015, 1287:95-103; Dale and Ow, 1991, *Proc. Natl Acad. Sci. USA* 88, 10558-10562; Srivastava and Thomson, Plant Biotechnol J, 2016; 14(2):471-82). Such methods typically require incorporation of the recombination site sequences recognized by the recombinase at particular locations within the transgene.

SUMMARY

Transgenic soybean plant cells comprising an INIR20 transgenic locus comprising an originator guide RNA recognition site (OgRRS) in a first DNA junction polynucleotide of a MON87701 transgenic locus and a cognate guide RNA recognition site (CgRRS) in a second DNA junction polynucleotide of the MON87701 transgenic locus are provided. Transgenic soybean plant cells comprising an INIR20 transgenic locus comprising an insertion and/or substitution in a DNA junction polynucleotide of a MON87701 transgenic locus of DNA comprising a cognate guide RNA recognition site (CgRRS) are provided. In certain embodiments, the MON87701 transgenic locus is set forth in SEQ ID NO:1, is present in seed deposited at the ATCC under accession No. PTA-8194 is present in progeny thereof, is present in allelic variants thereof, or is present in other variants thereof. INIR20 transgenic soybean plant cells, transgenic soybean plant seeds, and transgenic soybean plants all comprising a transgenic locus set forth in SEQ ID NO: 2, 3, or 15 are provided. Transgenic soybean plant parts including seeds and transgenic soybean plants comprising the soybean plant cells are also provided.

Methods for obtaining a bulked population of inbred seed comprising selfing the aforementioned transgenic soybean plants and harvesting seed comprising the INIR20 transgenic locus from the selfed soybean plant are also provided.

Methods of obtaining hybrid soybean seed comprising crossing the aforementioned transgenic soybean plants to a second soybean plant which is genetically distinct from the first soybean plant and harvesting seed comprising the INIR20 transgenic locus from the cross are provided. Methods for obtaining a bulked population of seed comprising selfing a transgenic soybean plant of comprising SEQ ID NO: 2, 3, or 15 and harvesting transgenic seed comprising the transgenic locus set forth in SEQ ID NO: 2, 3, or 15 are provided.

A DNA molecule comprising SEQ ID NO: 2, 3, 7, 8, 9, 14, 15, or 21 is provided. Processed transgenic soybean plant products and biological samples comprising the DNA molecules are provided. Nucleic acid molecules adapted for detection of genomic DNA comprising the DNA molecules, wherein said nucleic acid molecule optionally comprises a detectable label are provided. Methods of detecting a soybean plant cell comprising any forementioned INIR20 transgenic locus, comprising the step of detecting a DNA molecule comprising SEQ ID NO: 2, 3, 7, 8, 9, 14, 15, or 21 are provided.

Methods of excising the INIR20 transgenic locus from the genome of the aforementioned soybean plant cells comprising the steps of (a) contacting the edited transgenic plant genome of the plant cell with: (i) an RNA dependent DNA endonuclease (RdDe); and (ii) a guide RNA (gRNA) capable of hybridizing to the guide RNA hybridization site of the OgRRS and the CgRRS; wherein the RdDe recognizes a OgRRS/gRNA and a CgRRS/gRNA hybridization complex; and, (b) selecting a transgenic plant cell, transgenic plant part, or transgenic plant wherein the INIR20 transgenic locus flanked by the OgRRS and the CgRRS has been excised.

BRIEF DESCRIPTION OF THE DRAWINGS/FIGURES

FIG. 1 shows a schematic diagram of the MON87701 transgenic locus.

FIG. 2 shows a schematic diagram which compares current breeding strategies for introgression of transgenic events (i.e., transgenic loci) to alternative breeding strategies for introgression of transgenic events where the transgenic events (i.e., transgenic loci) can be removed following introgression to provide different combinations of transgenic traits. In FIG. 2, "GE" refers to genome editing (e.g., including introduction of targeted genetic changes with genome editing molecules) and "Event Removal" refers to excision of a transgenic locus (i.e., an "Event") with genome editing molecules.

FIG. 3A, B, C. FIG. 3A shows a schematic diagram of a non-limiting example of: (i) an untransformed plant chromosome containing non-transgenic DNA which includes the originator guide RNA recognition site (OgRRS) (top); (ii) the original transgenic locus with the OgRRS in the non-transgenic DNA of the $1^{st}$ junction polynucleotide (middle); and (iii) the modified transgenic locus with a cognate guide RNA inserted into the non-transgenic DNA of the $2^{nd}$ junction polynucleotide (bottom). FIG. 3B shows a schematic diagram of a non-limiting example of a process where a modified transgenic locus with a cognate guide RNA inserted into the non-transgenic DNA of the $2^{nd}$ junction polynucleotide (top) is subjected to cleavage at the OgRRS and CgRRS with one guide RNA (gRNA) that hybridizes to gRNA hybridization site in both the OgRRS and the CgRRS and an RNA dependent DNA endonuclease (RdDe) that recognizes and cleaves the gRNA/OgRRS and the gRNA/CgRRS complex followed by non-homologous end joining processes to provide a plant chromosome where the transgenic locus is excised. FIG. 3C shows a schematic diagram of a non-limiting example of a process where a modified transgenic locus with a cognate guide RNA inserted into the non-transgenic DNA of the $2^{nd}$ junction polynucleotide (top) is subjected to cleavage at the OgRRS and CgRRS with one guide RNA (gRNA) that hybridizes to the gRNA hybridization site in both the OgRRS and the CgRRS and an RNA dependent DNA endonuclease (RdDe) that recognizes and cleaves the gRNA/OgRRS and the gRNA/CgRRS complex in the presence of a donor DNA template. In FIG. 3C, cleavage of the modified transgenic locus in the presence of the donor DNA template which has homology to non-transgenic DNA but lacks the OgRRS in the $1^{st}$ and $2^{nd}$ junction polynucleotides followed by homology-directed repair processes to provide a plant chromosome where the transgenic locus is excised and non-transgenic DNA present in the untransformed plant chromosome is at least partially restored.

DETAILED DESCRIPTION

Figure 1:
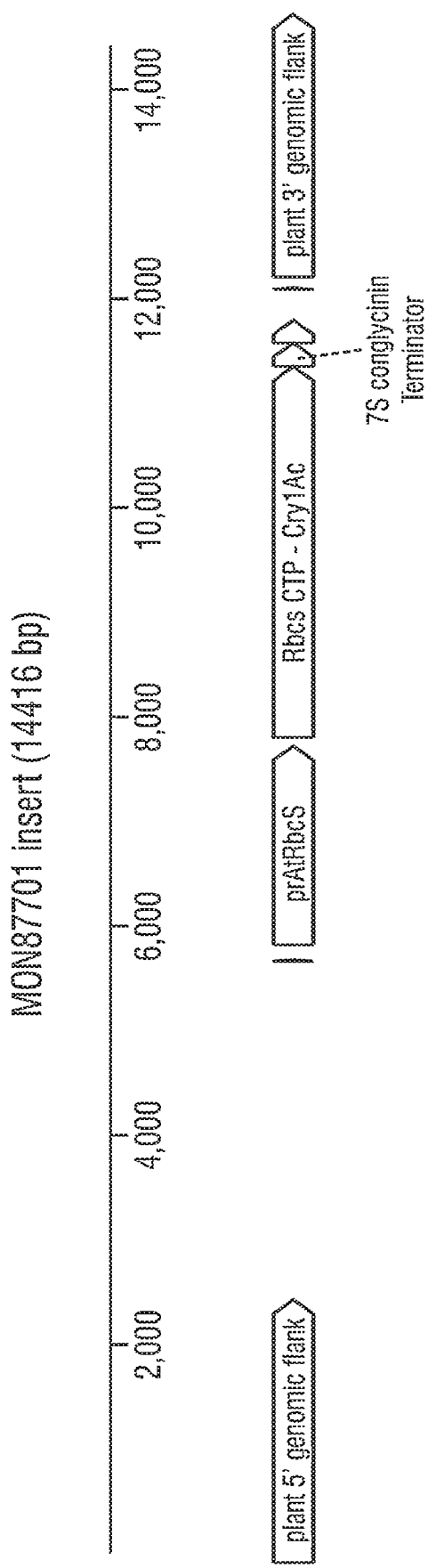

Unless otherwise stated, nucleic acid sequences in the text of this specification are given, when read from left to right, in the 5' to 3' direction. Nucleic acid sequences may be provided as DNA or as RNA, as specified; disclosure of one necessarily defines the other, as well as necessarily defines the exact complements, as is known to one of ordinary skill in the art.

Where a term is provided in the singular, the inventors also contemplate embodiments described by the plural of that term.

The term "about" as used herein means a value or range of values which would be understood as an equivalent of a stated value and can be greater or lesser than the value or range of values stated by 10 percent. Each value or range of values preceded by the term "about" is also intended to encompass the embodiment of the stated absolute value or range of values.

The phrase "allelic variant" as used herein refers to a polynucleotide or polypeptide sequence variant that occurs in a different strain, variety, or isolate of a given organism.

The term "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

As used herein, the phrase "approved transgenic locus" is a genetically modified plant event which has been authorized, approved, and/or de-regulated for any one of field testing, cultivation, human consumption, animal consumption, and/or import by a governmental body. Illustrative and non-limiting examples of governmental bodies which provide such approvals include the Ministry of Agriculture of Argentina, Food Standards Australia New Zealand, National Biosafety Technical Committee (CTNBio) of Brazil, Canadian Food Inspection Agency, China Ministry of Agriculture Biosafety Network, European Food Safety Authority, US Department of Agriculture, US Department of Environmental Protection, and US Food and Drug Administration.

The term "backcross", as used herein, refers to crossing an F1 plant or plants with one of the original parents. A backcross is used to maintain or establish the identity of one parent (species) and to incorporate a particular trait from a second parent (species). The term "backcross generation", as used herein, refers to the offspring of a backcross.

As used herein, the phrase "biological sample" refers to either intact or non-intact (e.g., milled seed or plant tissue, chopped plant tissue, lyophilized tissue) plant tissue. It may also be an extract comprising intact or non-intact seed or plant tissue. The biological sample can comprise flour, meal, syrup, oil, starch, and cereals manufactured in whole or in part to contain crop plant by-products. In certain embodiments, the biological sample is "non-regenerable" (i.e., incapable of being regenerated into a plant or plant part). In certain embodiments, the biological sample refers to a homogenate, an extract, or any fraction thereof containing genomic DNA of the organism from which the biological sample was obtained, wherein the biological sample does not comprise living cells.

As used herein, the terms "correspond," "corresponding," and the like, when used in the context of an nucleotide position, mutation, and/or substitution in any given polynucleotide (e.g., an allelic variant of SEQ ID NO: 1) with respect to the reference polynucleotide sequence (e.g., SEQ ID NO: 1) all refer to the position of the polynucleotide residue in the given sequence that has identity to the residue in the reference nucleotide sequence when the given polynucleotide is aligned to the reference polynucleotide sequence using a pairwise alignment algorithm (e.g., CLUSTAL O 1.2.4 with default parameters).

As used herein, the terms "Cpf1" and "Cas12a" are used interchangeably to refer to the same RNA dependent DNA endonuclease (RdDe). A Cas12a protein provided herein includes the protein of SEQ ID NO: 16.

The term "crossing" as used herein refers to the fertilization of female plants (or gametes) by male plants (or gametes). The term "gamete" refers to the haploid reproductive cell (egg or pollen) produced in plants by meiosis from a gametophyte and involved in sexual reproduction, during which two gametes of opposite sex fuse to form a diploid zygote. The term generally includes reference to a pollen (including the sperm cell) and an ovule (including the ovum). When referring to crossing in the context of achieving the introgression of a genomic region or segment, the skilled person will understand that in order to achieve the introgression of only a part of a chromosome of one plant into the chromosome of another plant, random portions of the genomes of both parental lines recombine during the cross due to the occurrence of crossing-over events in the production of the gametes in the parent lines. Therefore, the genomes of both parents must be combined in a single cell by a cross, where after the production of gametes from the cell and their fusion in fertilization will result in an introgression event.

As used herein, the phrases "DNA junction polynucleotide" and "junction polynucleotide" refers to a polynucleotide of about 18 to about 500 base pairs in length comprised of both endogenous chromosomal DNA of the plant genome and heterologous transgenic DNA which is inserted in the plant genome. A junction polynucleotide can thus comprise about 8, 10, 20, 50, 100, 200, 250, 500, or 1000 base pairs of endogenous chromosomal DNA of the plant genome and about 8, 10, 20, 50, 100, 200, 250, 500, or 1000 base pairs of heterologous transgenic DNA which span the one end of the transgene insertion site in the plant chromosomal DNA. Transgene insertion sites in chromosomes will typically contain both a 5' junction polynucleotide and a 3' junction polynucleotide. In embodiments set forth herein in SEQ ID NO: 1, the 5' junction polynucleotide is located at the 5' end of the sequence and the 3' junction polynucleotide is located at the 3' end of the sequence. In a non-limiting and illustrative example, a 5' junction polynucleotide of a transgenic locus is telomere proximal in a chromosome arm and the 3' junction polynucleotide of the transgenic locus is centromere proximal in the same chromosome arm. In another non-limiting and illustrative example, a 5' junction polynucleotide of a transgenic locus is centromere proximal in a chromosome arm and the 3' junction polynucleotide of the transgenic locus is telomere proximal in the same chromosome arm. The junction polynucleotide which is telomere proximal and the junction polynucleotide which is centromere proximal can be determined by comparing non-transgenic genomic sequence of a sequenced non-transgenic plant genome to the non-transgenic DNA in the junction polynucleotides.

The term "donor," as used herein in the context of a plant, refers to the plant or plant line from which the trait, transgenic event, or genomic segment originates, wherein the donor can have the trait, introgression, or genomic segment in either a heterozygous or homozygous state.

As used herein, the term "MON87701" is used to refer to any of a transgenic soybean locus, transgenic soybean plants and parts thereof including seed set forth in U.S. Pat. No. 8,049,071, which is incorporated herein by reference in its entirety. Representative MON87701 transgenic soybean seed have been deposited with American Type Culture Collection (ATCC, Manassas, Va. 20110-2209 USA) under Accession No. PTA-8194. MON87701 transgenic loci include loci having the sequence of SEQ ID NO:1, the sequence of the MON87701 locus in the deposited seed of Accession No. PTA-8194 and any progeny thereof, as well as allelic variants and other variants of SEQ ID NO:1.

As used herein, the terms "excise" and "delete," when used in the context of a DNA molecule, are used interchangeably to refer to the removal of a given DNA segment or element (e.g., transgene element or transgenic locus or portion thereof) of the DNA molecule.

As used herein, the phrase "elite crop plant" refers to a plant which has undergone breeding to provide one or more trait improvements. Elite crop plant lines include plants which are an essentially homozygous, e.g., inbred or doubled haploid. Elite crop plants can include inbred lines used as is or used as pollen donors or pollen recipients in hybrid seed production (e.g., used to produce F1 plants). Elite crop plants can include inbred lines which are selfed to produce non-hybrid cultivars or varieties or to produce (e.g., bulk up) pollen donor or recipient lines for hybrid seed production. Elite crop plants can include hybrid F1 progeny of a cross between two distinct elite inbred or doubled haploid plant lines.

As used herein, an "event," "a transgenic event," "a transgenic locus" and related phrases refer to an insertion of one or more transgenes at a unique site in the genome of a plant as well as to DNA fragments, plant cells, plants, and plant parts (e.g., seeds) comprising genomic DNA containing the transgene insertion. Such events typically comprise both a 5' and a 3' junction polynucleotide and confer one or more useful traits including herbicide tolerance, insect resistance, male sterility, and the like.

As used herein, the phrases "endogenous sequence," "endogenous gene," "endogenous DNA," "endogenous polynucleotide," and the like refer to the native form of a polynucleotide, gene or polypeptide in its natural location in the organism or in the genome of an organism.

The terms "exogenous" and "heterologous" as are used synonymously herein to refer to any polynucleotide (e.g., DNA molecule) that has been inserted into a new location in the genome of a plant. Non-limiting examples of an exogenous or heterologous DNA molecule include a synthetic DNA molecule, a non-naturally occurring DNA molecule, a DNA molecule found in another species, a DNA molecule found in a different location in the same species, and/or a DNA molecule found in the same strain or isolate of a species, where the DNA molecule has been inserted into a new location in the genome of a plant.

As used herein, the term "F1" refers to any offspring of a cross between two genetically unlike individuals.

The term "gene," as used herein, refers to a hereditary unit consisting of a sequence of DNA that occupies a specific location on a chromosome and that contains the genetic instruction for a particular characteristics or trait in an organism. The term "gene" thus includes a nucleic acid (for example, DNA or RNA) sequence that comprises coding sequences necessary for the production of an RNA, or a polypeptide or its precursor. A functional polypeptide can be encoded by a full length coding sequence or by any portion of the coding sequence as long as the desired activity or functional properties (e.g., enzymatic activity, pesticidal activity, ligand binding, and/or signal transduction) of the RNA or polypeptide are retained.

The term "identifying," as used herein with respect to a plant, refers to a process of establishing the identity or distinguishing character of a plant, including exhibiting a certain trait, containing one or more transgenes, and/or containing one or more molecular markers.

As used herein, the term "INIR20" is used to refer either individually collectively to items that include any or all of the MON87701 transgenic soybean loci which have been modified as disclosed herein, modified MON87701 transgenic soybean plants and parts thereof including seed, and DNA obtained therefrom.

The term "isolated" as used herein means having been removed from its natural environment.

As used herein, the terms "include," "includes," and "including" are to be construed as at least having the features to which they refer while not excluding any additional unspecified features.

As used herein, the phrase "introduced transgene" is a transgene not present in the original transgenic locus in the genome of an initial transgenic event or in the genome of a progeny line obtained from the initial transgenic event. Examples of introduced transgenes include exogenous transgenes which are inserted in a resident original transgenic locus.

As used herein, the terms "introgression", "introgressed" and "introgressing" refer to both a natural and artificial process, and the resulting plants, whereby traits, genes or DNA sequences of one species, variety or cultivar are moved into the genome of another species, variety or cultivar, by crossing those species. The process may optionally be completed by backcrossing to the recurrent parent. Examples of introgression include entry or introduction of a gene, a transgene, a regulatory element, a marker, a trait, a trait locus, or a chromosomal segment from the genome of one plant into the genome of another plant.

The phrase "marker-assisted selection", as used herein, refers to the diagnostic process of identifying, optionally followed by selecting a plant from a group of plants using the presence of a molecular marker as the diagnostic characteristic or selection criterion. The process usually involves detecting the presence of a certain nucleic acid sequence or polymorphism in the genome of a plant.

The phrase "molecular marker", as used herein, refers to an indicator that is used in methods for visualizing differences in characteristics of nucleic acid sequences. Examples of such indicators are restriction fragment length polymorphism (RFLP) markers, amplified fragment length polymorphism (AFLP) markers, single nucleotide polymorphisms (SNPs), microsatellite markers (e.g. SSRs), sequence-characterized amplified region (SCAR) markers, Next Generation Sequencing (NGS) of a molecular marker, cleaved amplified polymorphic sequence (CAPS) markers or isozyme markers or combinations of the markers described herein which defines a specific genetic and chromosomal location.

As used herein the terms "native" or "natural" define a condition found in nature. A "native DNA sequence" is a DNA sequence present in nature that was produced by natural means or traditional breeding techniques but not generated by genetic engineering (e.g., using molecular biology/transformation techniques).

The term "offspring", as used herein, refers to any progeny generation resulting from crossing, selfing, or other propagation technique.

The phrase "operably linked" refers to a juxtaposition wherein the components so described are in a relationship permitting them to function in their intended manner. For instance, a promoter is operably linked to a coding sequence if the promoter affects its transcription or expression. When the phrase "operably linked" is used in the context of a PAM site and a guide RNA hybridization site, it refers to a PAM site which permits cleavage of at least one strand of DNA in a polynucleotide with an RNA dependent DNA endonuclease or RNA dependent DNA nickase which recognize the PAM site when a guide RNA complementary to guide RNA hybridization site sequences adjacent to the PAM site is present. A OgRRS and its CgRRS are operably linked to junction polynucleotides when they can be recognized by a gRNA and an RdDe to provide for excision of the transgenic locus or portion thereof flanked by the junction polynucleotides.

As used herein, the term "plant" includes a whole plant and any descendant, cell, tissue, or part of a plant. The term "plant parts" include any part(s) of a plant, including, for example and without limitation: seed (including mature seed and immature seed); a plant cutting; a plant cell; a plant cell culture; or a plant organ (e.g., pollen, embryos, flowers, fruits, shoots, leaves, roots, stems, and explants). A plant tissue or plant organ may be a seed, protoplast, callus, or any other group of plant cells that is organized into a structural or functional unit. A plant cell or tissue culture may be capable of regenerating a plant having the physiological and morphological characteristics of the plant from which the cell or tissue was obtained, and of regenerating a plant having substantially the same genotype as the plant. Regenerable cells in a plant cell or tissue culture may be embryos, protoplasts, meristematic cells, callus, pollen, leaves, anthers, roots, root tips, silk, flowers, kernels, ears, cobs, husks, or stalks. In contrast, some plant cells are not capable of being regenerated to produce plants and are referred to herein as "non-regenerable" plant cells.

The term "purified," as used herein defines an isolation of a molecule or compound in a form that is substantially free of contaminants normally associated with the molecule or compound in a native or natural environment and means having been increased in purity as a result of being separated from other components of the original composition. The term "purified nucleic acid" is used herein to describe a nucleic acid sequence which has been separated from other compounds including, but not limited to polypeptides, lipids and carbohydrates.

The term "recipient", as used herein, refers to the plant or plant line receiving the trait, transgenic event or genomic segment from a donor, and which recipient may or may not have the have trait, transgenic event or genomic segment itself either in a heterozygous or homozygous state.

As used herein the term "recurrent parent" or "recurrent plant" describes an elite line that is the recipient plant line in a cross and which will be used as the parent line for successive backcrosses to produce the final desired line.

As used herein the term "recurrent parent percentage" relates to the percentage that a backcross progeny plant is identical to the recurrent parent plant used in the backcross. The percent identity to the recurrent parent can be determined experimentally by measuring genetic markers such as SNPs and/or RFLPs or can be calculated theoretically based on a mathematical formula.

The terms "selfed," "selfing," and "self," as used herein, refer to any process used to obtain progeny from the same plant or plant line as well as to plants resulting from the process. As used herein, the terms thus include any fertilization process wherein both the ovule and pollen are from the same plant or plant line and plants resulting therefrom. Typically, the terms refer to self-pollination processes and progeny plants resulting from self-pollination.

The term "selecting", as used herein, refers to a process of picking out a certain individual plant from a group of individuals, usually based on a certain identity, trait, characteristic, and/or molecular marker of that individual.

As used herein, the phrase "originator guide RNA recognition site" or the acronym "OgRRS" refers to an endogenous DNA polynucleotide comprising a protospacer adjacent motif (PAM) site operably linked to a guide RNA hybridization site (i.e., protospacer sequence). In certain embodiments, an OgRRS can be located in an untransformed plant chromosome or in non-transgenic DNA of a DNA junction polynucleotide of both an original transgenic locus and a modified transgenic locus. In certain embodiments, an OgRRS can be located in transgenic DNA of a DNA junction polynucleotide of both an original transgenic locus and a modified transgenic locus. In certain embodiments, an OgRRS can be located in both transgenic DNA and non-transgenic DNA of a DNA junction polynucleotide of both an original transgenic locus and a modified transgenic locus (i.e., can span transgenic and non-transgenic DNA in a DNA junction polynucleotide).

As used herein the phrase "cognate guide RNA recognition site" or the acronym "CgRRS" refer to a DNA polynucleotide comprising a PAM site operably linked to a guide RNA hybridization site (i.e., protospacer sequence), where the CgRRS is absent from transgenic plant genomes comprising a first original transgenic locus that is unmodified and where the CgRRS and its corresponding OgRRS can hybridize to a single gRNA. A CgRRS can be located in transgenic DNA of a DNA junction polynucleotide of a modified transgenic locus, in transgenic DNA of a DNA junction polynucleotide of a modified transgenic locus, or in both transgenic and non-transgenic DNA of a modified transgenic locus (i.e., can span transgenic and non-transgenic DNA in a DNA junction polynucleotide).

As used herein, the phrase "a transgenic locus excision site" refers to the DNA which remains in the genome of a plant or in a DNA molecule (e.g., an isolated or purified DNA molecule) wherein a segment comprising, consisting essentially of, or consisting of a transgenic locus has been deleted. In a non-limiting and illustrative example, a transgenic locus excision site can thus comprise a contiguous segment of DNA comprising at least 10 base pairs of DNA that is telomere proximal to the deleted transgenic locus or to the deleted segment of the transgenic locus and at least 10 base pairs of DNA that is centromere proximal to the deleted transgenic locus or to the deleted segment of the transgenic locus.

As used herein, the phrase "transgene element" refers to a segment of DNA comprising, consisting essentially of, or consisting of a promoter, a 5' UTR, an intron, a coding region, a 3'UTR, or a polyadenylation signal. Polyadenylation signals include transgene elements referred to as "terminators" (e.g., NOS, pinII, rbcs, Hsp17, TubA).

To the extent to which any of the preceding definitions is inconsistent with definitions provided in any patent or non-patent reference incorporated herein by reference, any patent or non-patent reference cited herein, or in any patent or non-patent reference found elsewhere, it is understood that the preceding definition will be used herein.

Various sequences set forth in the sequence listing are described in the following table.

TABLE 1

Description of sequences.

| SEQ ID NO | Description |
| --- | --- |
| 1 | MON87701 transgenic locus. The MON87701 5' flank region comprises nucleotides 1-5757 of SEQ ID NO: 1. The MON87701 transgenic insert extends from nucleotides 5758-12183 of SEQ ID NO: 1. The MON87701 3' flanking DNA comprises nucleotides 12184-14416 of SEQ ID NO: 1. |
| 2 | INIR20-1 (G1 Cut) |
| 3 | INIR20-2 (Insertion of 27 bp CgRRS of SEQ ID NO: 8 in 5' junction polynucleotide of MON87701 with donor DNA template of SEQ ID NO: 21)) |
| 4 | gRNA-1 targeting 5' junction polynucleotide of MON87701 |
| 5 | gRNA-2 targeting 5' junction polynucleotide of MON87701 |
| 6 | OgRRS (located in 3' junction polynucleotide of SEQ ID NO: 1) |
| 7 | CgRRS = Flanking DNA (located in 5' junction polynucleotide of INIR20-3 transgenic locus of SEQ ID NO: 15) |
| 8 | CgRRS = Flanking DNA (located in 5' junction polynucleotide of INIR20-2 transgenic locus of SEQ ID NO: 3) |
| 9 | MON87701 donor template sequence #1 containing SEQ ID NO: 7 CgRRS to yield INIR20-3 transgenic locus of SEQ ID NO: 15 |
| 10 | MON87701 5' target insertion site |
| 11 | MON87701-gRNA coding sequence for gRNAs targeting CgRRS and OgRRS of INIR20-2 (SEQ ID NO: 3) and INIR20-3 (SEQ ID NO: 15) |
| 12 | MON87701 5' primer |
| 13 | MON87701 3' primer |
| 14 | MON87701 CgRRS and flank |
| 15 | INIR20-3 resultant sequence (Insertion of CgRRS of SEQ ID NO: 7 in MON87701 5' junction polynucleotide with donor DNA template of SEQ ID NO: 9) |

TABLE 1-continued

Description of sequences.

| SEQ ID NO | Description |
|---|---|
| 16 | (Cas 12a Nuclease ) (>sp|U2UMQ6|CS12A_ACISB CRISPR-associated endonuclease Cas12a OS = *Acidaminococcus* sp. (strain BV3L6) OX = 1111120 GN = cas12aPE = 1 SV = 1) |
| 17 | MON87701 5' Junction Polynucleotide |
| 18 | MON87701 5' plant genomic flanking |
| 19 | MON87701 3' Junction Polynucleotide |
| 20 | MON87701 3' plant genomic flanking |
| 21 | MON87701 donor template sequence #2 for SEQ ID NO: 8 CgRRS to yield INIR20-2 transgenic locus of SEQ ID NO: 3 |

Genome editing molecules can permit introduction of targeted genetic change conferring desirable traits in a variety of crop plants (Zhang et al. Genome Biol. 2018; 19: 210; Schindele et al. FEBS Lett. 2018; 592(12):1954). Desirable traits introduced into crop plants such as soybean and soybean include herbicide tolerance, improved food and/or feed characteristics, male-sterility, and drought stress tolerance. Nonetheless, full realization of the potential of genome editing methods for crop improvement will entail efficient incorporation of the targeted genetic changes in germplasm of different elite crop plants adapted for distinct growing conditions. Such elite crop plants will also desirably comprise useful transgenic loci which confer various traits including herbicide tolerance, pest resistance (e.g.; insect, nematode, fungal disease, and bacterial disease resistance), conditional male sterility systems for hybrid seed production, abiotic stress tolerance (e.g., drought tolerance), improved food and/or feed quality, and improved industrial use (e.g., biofuel). Provided herein are methods whereby targeted genetic changes are efficiently combined with desired subsets of transgenic loci in elite progeny plant lines (e.g., elite inbreds used for hybrid seed production or for inbred varietal production). Also provided are plant genomes containing modified transgenic loci which can be selectively excised with a single gRNA molecule. Such modified transgenic loci comprise an originator guide RNA recognition site (OgRRS) which is identified in non-transgenic DNA of a first junction polynucleotide of the transgenic locus and cognate guide RNA recognition site (CgRRS) which is introduced (e.g., by genome editing methods) into a second junction polynucleotide of the transgenic locus and which can hybridize to the same gRNA as the OgRRS, thereby permitting excision of the modified transgenic locus with a single guide RNA. An originator guide RNA recognition site (OgRRS) comprises endogenous DNA found in untransformed plants and in endogenous non-transgenic DNA of junction polynucleotides of transgenic plants containing a modified or unmodified transgenic locus. The OgRRS located in non-transgenic DNA of a first DNA junction polynucleotide is used to design a related cognate guide RNA recognition site (CgRRS) which is introduced (e.g., by genome editing methods) into the second junction polynucleotide of the transgenic locus. A CgRRS is thus present in junction polynucleotides of modified transgenic loci provided herein and is absent from endogenous DNA found in untransformed plants and absent from endogenous non-transgenic DNA found in junction sequences of transgenic plants containing an unmodified transgenic locus. Also provided are unique transgenic locus excision sites created by excision of such modified transgenic loci, DNA molecules comprising the modified transgenic loci, unique transgenic locus excision sites and/or plants comprising the same, biological samples containing the DNA, nucleic acid markers adapted for detecting the DNA molecules, and related methods of identifying the elite crop plants comprising unique transgenic locus excision sites.

Figure 2:
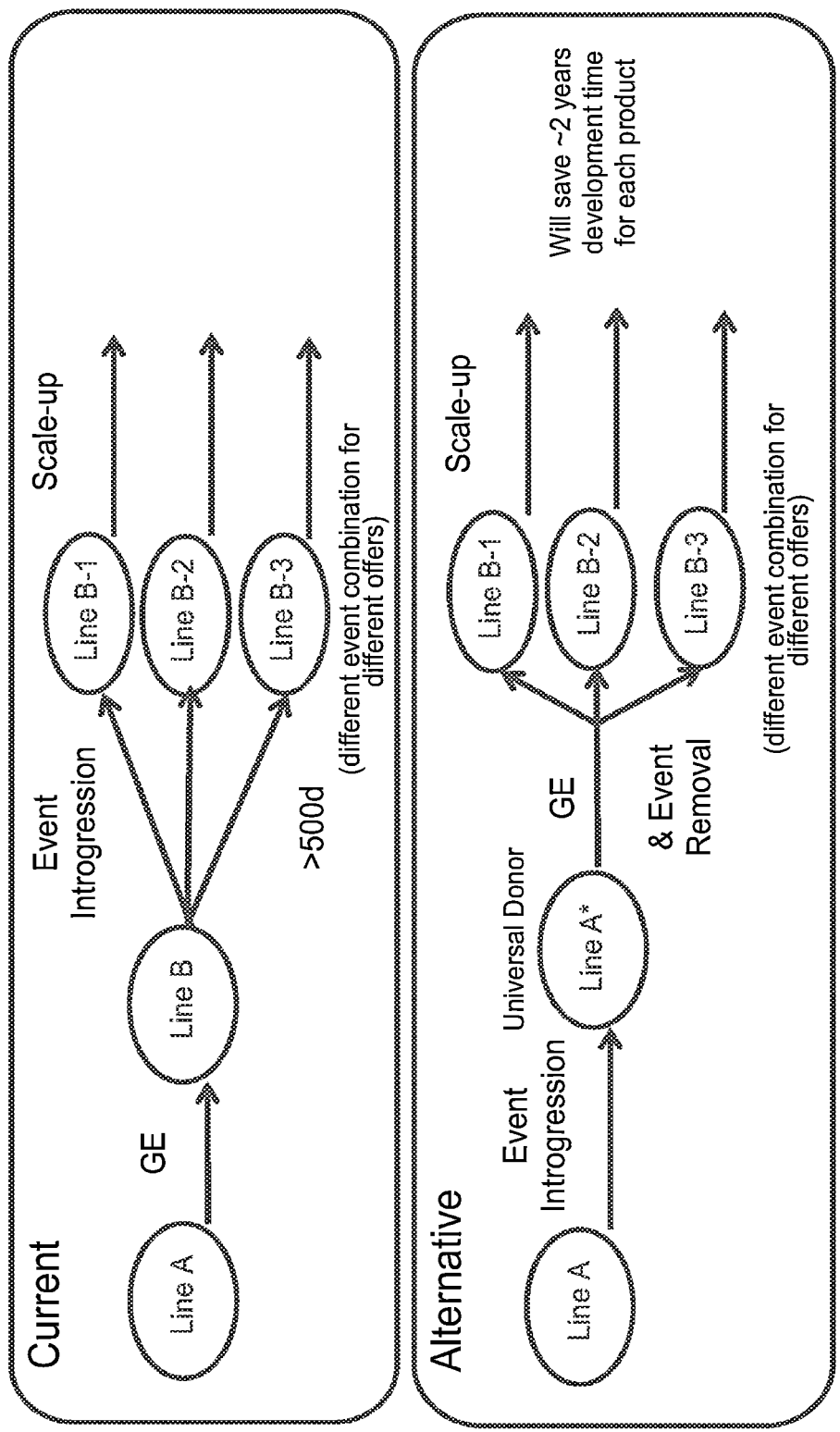
Figure 3A:
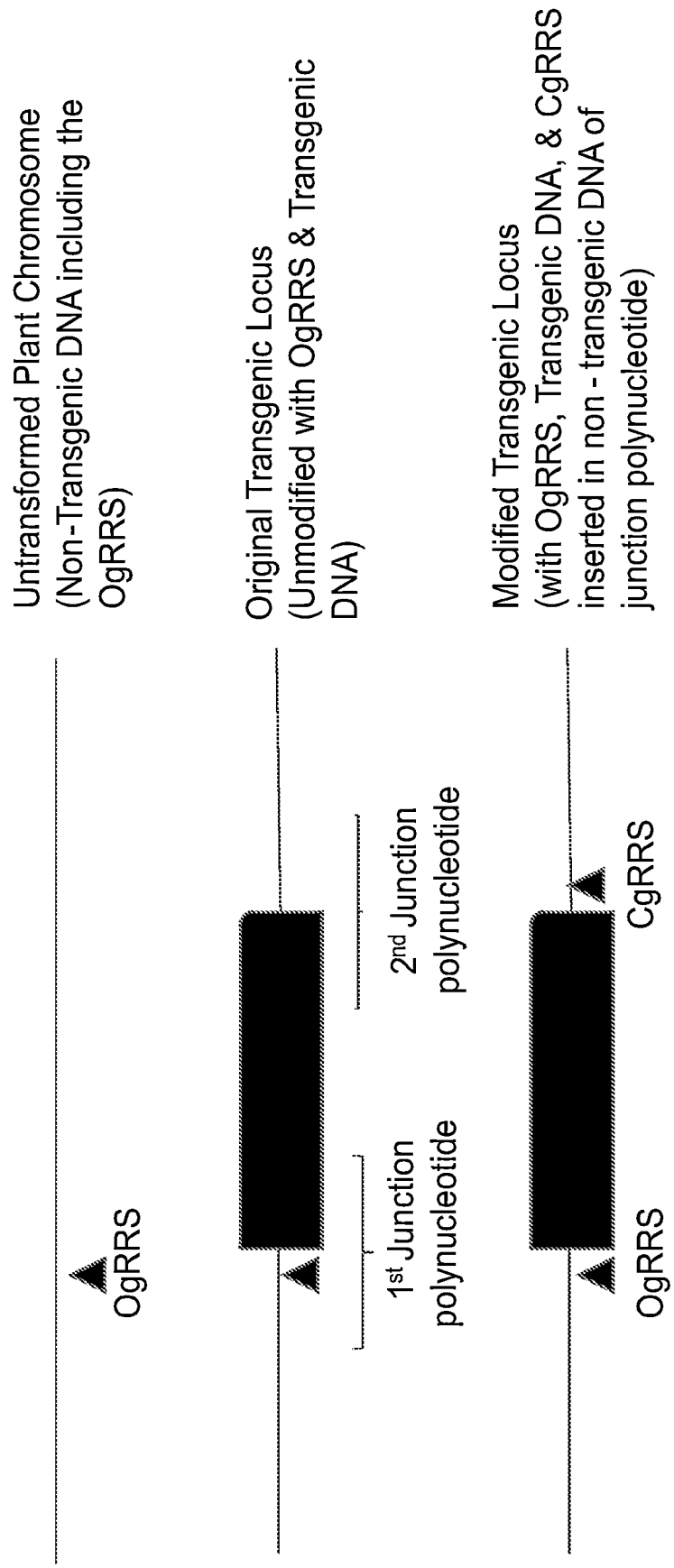

Also provided herein are methods whereby targeted genetic changes are efficiently combined with desired subsets of transgenic loci in elite progeny plant lines (e.g., elite inbreds used for hybrid seed production or for inbred varietal production). Examples of such methods include those illustrated in FIG. 2. In certain embodiments, INIR20 transgenic loci provided here are characterized by polynucleotide sequences that can facilitate as necessary the removal of the INIR20 transgenic loci from the genome. Useful applications of such INIR20 transgenic loci and related methods of making include targeted excision of a INIR20 transgenic locus or portion thereof in certain breeding lines to facilitate recovery of germplasm with subsets of transgenic traits tailored for specific geographic locations and/or grower preferences. Other useful applications of such INIR20 transgenic loci and related methods of making include removal of transgenic traits from certain breeding lines when it is desirable to replace the trait in the breeding line without disrupting other transgenic loci and/or non-transgenic loci. In certain embodiments, soybean genomes containing INIR20 transgenic loci or portions thereof which can be selectively excised with one or more gRNA molecules and RdDe (RNA dependent DNA endonucleases) which form gRNA/target DNA complexes. Such selectively excisable INIR20 transgenic loci can comprise an originator guide RNA recognition site (OgRRS) which is identified in non-transgenic DNA, transgenic DNA, or a combination thereof in of a first junction polynucleotide of the transgenic locus and cognate guide RNA recognition site (CgRRS) which is introduced (e.g., by genome editing methods) into a second junction polynucleotide of the transgenic locus and which can hybridize to the same gRNA as the OgRRS, thereby permitting excision of the modified transgenic locus or portions thereof with a single guide RNA (e.g., as shown in FIGS. 3A and B). In certain embodiments, an originator guide RNA recognition site (OgRRS) comprises endogenous DNA found in untransformed plants and in endogenous non-transgenic DNA of junction polynucleotides of transgenic plants containing a modified or unmodified transgenic locus. In certain embodiments, an originator guide RNA recognition site (OgRRS) comprises exogenous transgenic DNA of junction polynucleotides of transgenic plants containing a modified or unmodified transgenic locus. The OgRRS located in non-transgenic DNA transgenic DNA, or a combination thereof in of a first DNA junction polynucleotide is used to design a related cognate guide RNA recognition site (CgRRS) which is introduced (e.g., by genome editing methods) into the second junction polynucleotide of the transgenic locus. A CgRRS is thus present in junction polynucleotides of modified transgenic loci provided herein and is absent from endogenous DNA found in untransformed plants and absent from junction sequences of transgenic plants containing an unmodified transgenic locus. A CgRRS is also absent from a combination of non-transgenic and transgenic DNA found in junction sequences of transgenic plants containing an unmodified transgenic locus. An example of OgRRS polynucleotide sequences in or near a 3' junction polynucleotide in an MON87701 transgenic locus include SEQ ID NO: 6. OgRRS polynucleotide sequences located in a first junction polynucleotide can be introduced into the second junction polynucleotide using donor DNA templates as elsewhere described herein. Donor DNA templates for introducing the SEQ ID NO: 6 OgRRS into the 5' junction polynucleotide of an MON87701 locus includes the donor DNA templates comprising SEQ ID NO: 9 and 21. Double stranded breaks in a 5' junction polynucleotide of SEQ ID NO: 1 can be introduced with the Guide-1 or Guide-2 gRNAs, which are respectively encoded by SEQ ID NO: 4 and 5, and a Cas12a nuclease. In certain embodiments, double stranded breaks in a 5' junction polynucleotide of SEQ ID NO: 1 can be introduced with the Guide-1 or 2 gRNAs and a Cas12a nuclease (e.g., a Cas12a nuclease of SEQ ID NO: 16). Integration of the SEQ ID NO: 9 or 21 donor DNA template comprising the CgRRS into the 5' junction polynucleotide of an MON87701 locus at the double stranded breaks introduced by the gRNAs encoded by SEQ ID NO: 4 or 5 and a Cas12a nuclease can provide an INIR20 locus comprising the CgRRS sequence set forth in SEQ ID NO: 3 or 15. Subsequences comprising the CgRRS which is located in the 5" junction polynucleotide of the INIR20 transgenic locus are set forth in SEQ ID NO: 7, 8, and 14. Double stranded breaks in a 5' junction polynucleotide of SEQ ID NO: 1 can be introduced with gRNAs encoded by SEQ ID NO: 4 or 5 and a Cas12a nuclease. A donor DNA template of SEQ ID NO: 9 or the equivalent thereof having longer or shorter homology arms can be used to obtain the CgRRS insertion in the 5' junction polynucleotide that is set forth in SEQ ID NO: 7. An INIR20 transgenic locus containing the CgRRS insertion of SEQ ID NO: 7 is set forth in SEQ ID NO: 15. A donor DNA template of SEQ ID NO: 21 or the equivalent thereof having longer or shorter homology arms can be used to obtain the CgRRS insertion in the 5' junction polynucleotide of MON87701 that is set forth in SEQ ID NO: 8. An INIR20 transgenic locus containing the CgRRS insertion of SEQ ID NO: 8 is set forth in SEQ ID NO: 3.

Also provided herein are allelic variants of any of the INIR20 transgenic loci or DNA molecules provided herein. In certain embodiments, such allelic variants of INIR20 transgenic loci include sequences having at least 85%, 90%, 95%, 98%, or 99% sequence identity across the entire length or at least 20, 40, 100, 500, 1,000, 2,000, 4,000, 6,000, 8,000, 9,000, 10,000, 11,000, 12,000, 13,000, 14,000, or 14,416 nucleotides of SEQ ID NO: 2, 3, or 15. In certain embodiments, such allelic variants of INIR20 DNA molecules include sequences having at least 85%, 90%, 95%, 98%, or 99% sequence identity across the entire length of SEQ ID NO: 2, 3, 7, 8, 9, 14, 15, or 21.

Also provided are unique transgenic locus excision sites created by excision of INIR20 transgenic loci or selectively excisable INIR20 transgenic loci, DNA molecules comprising the INIR20 transgenic loci or unique fragments thereof (i.e., fragments of an INIR20 locus which are not found in an MON87701 transgenic locus), INIR20 plants comprising the same, biological samples containing the DNA, nucleic acid markers adapted for detecting the DNA molecules, and related methods of identifying soybean plants comprising unique INIR20 transgenic locus excision sites and unique fragments of a INIR20 transgenic locus. An example of such an excision site would include an excision site created by excising the INIR20 transgenic locus with a guide RNA encoded by SEQ ID NO: 4 or S and a suitable Cas RdDe (e.g., a Cas12a nuclease of SEQ ID NO: 16). DNA molecules comprising unique fragments of an INIR20 transgenic locus are diagnostic for the presence of an INIR20 transgenic locus or fragments thereof in a soybean plant, soybean cell, soybean seed, products obtained therefrom (e.g., seed meal or stover), and biological samples. DNA molecules comprising unique fragments of an INIR20 transgenic locus include DNA molecules comprising the CgRRS include SEQ ID NO: 7, 8, and 14.

Methods provided herein can be used to excise any transgenic locus where the first and second junction sequences comprising the endogenous non-transgenic genomic DNA and the heterologous transgenic DNA which are joined at the site of transgene insertion in the plant genome are known or have been determined. In certain embodiments provided herein, transgenic loci can be removed from crop plant lines to obtain crop plant lines with tailored combinations of transgenic loci and optionally targeted genetic changes. Such first and second junction sequences are readily identified in new transgenic events by inverse PCR techniques using primers which are complementary the inserted transgenic sequences. In certain embodiments, the first and second junction sequences of transgenic loci are published. An example of a transgenic locus which can be improved and used in the methods provided herein is the soybean MON87701 transgenic locus. The soybean MON87701 transgenic locus is depicted in FIG. 1. Soybean plants comprising the MON87701 transgenic locus and seed thereof have been cultivated, been placed in commerce, and have been described in a variety of publications by various governmental bodies. Databases which have compiled descriptions of the MON87701 transgenic locus include the International Service for the Acquisition of Agri-biotech Applications (ISAAA) database (available on the world wide web internet site "isaaa.org/gmapprovaldatabase/event"), the GenBit LLC database (available on the world wide web internet site "genbitgroup.com/en/gmo/gmodatabase"), and the Biosafety Clearing-House (BCH) database (available on the http internet site "bch.cbd.int/database/organisms").

Sequences of the junction polynucleotides as well as the transgenic insert(s) of the MON87701 transgenic locus which can be improved by the methods provided herein are set forth or otherwise provided in SEQ ID NO: 1, U.S. Pat. No. 8,049,071, the sequence of the MON87701 locus in the deposited seed of ATCC accession No. PTA-8194, and elsewhere in this disclosure. In certain embodiments provided herein, the MON87701 transgenic locus set forth in SEQ ID NO: 1 or present in the deposited seed of ATCC accession No. PTA-8194 is referred to as an "original MON87701 transgenic locus." Allelic or other variants of the sequence set forth SEQ ID NO: 1, the patent references set forth therein and incorporated herein by reference in their entireties, and elsewhere in this disclosure which may be present in certain variant MON87701 transgenic plant loci (e.g., progeny of deposited seed of accession No. PTA-8194 which contain allelic variants of SEQ ID NO:1 or progeny originating from transgenic plant cells comprising the original MON87701 transgenic locus set forth in U.S. Pat. No.

8,049,071) can also be improved by identifying sequences in the variants that correspond to the SEQ ID NO: 1 by performing a pairwise alignment (e.g., using CLUSTAL O 1.2.4 with default parameters) and making corresponding changes in the allelic or other variant sequences. Such allelic or other variant sequences include sequences having at least 85%, 90%, 95%, 98%, or 99% sequence identity across the entire length or at least 20, 40, 100, 500, 1,000, 2,000, 4,000, 8,000, 10,000, 11,000, 12,000, 13,000 or 13659 nucleotides of SEQ ID NO: 1. Also provided are plants, plant parts including seeds, genomic DNA, and/or DNA obtained from INIR20 plants which comprise one or more modifications (e.g., via insertion of a CgRRS in a junction polynucleotide sequence) which provide for selective excision of the INIR20 transgenic locus or a portion thereof. Also provided herein are methods of detecting plants, genomic DNA, and/or DNA obtained from plants comprising a INIR20 transgenic locus which contains one or more of a CgRRS, deletions of selectable marker genes, deletions of non-essential DNA, and/or a transgenic locus excision site. A first junction polynucleotide of a MON87701 transgenic locus can comprise either one of the junction polynucleotides found at the 5' end or the 3' end of any one of the sequences set forth in SEQ ID NO: 1, allelic variants thereof, or other variants thereof. An OgRRS can be found within non-transgenic DNA, transgenic DNA, or a combination thereof in either one of the junction polynucleotides of any one of SEQ ID NO: 1, allelic variants thereof, or other variants thereof. A second junction polynucleotide of a transgenic locus can comprise either one of the junction polynucleotides found at the 5' or 3' end of any one of the sequences set forth in SEQ ID NO: 1, allelic variants thereof, or other variants thereof. A CgRRS can be introduced within transgenic, non-transgenic DNA, or a combination thereof of either one of the junction polynucleotides of any one of SEQ ID NO: 1, allelic variants thereof, or other variants thereof to obtain an INIR20 transgenic locus. In certain embodiments, the OgRRS is found in non-transgenic DNA or transgenic DNA of the 5' junction polynucleotide of a transgenic locus of any one of SEQ ID NO: 1, allelic variants thereof, or other variants thereof and the corresponding CgRRS is introduced into the transgenic DNA, non-transgenic DNA, or a combination thereof in the 3' junction polynucleotide of the MON87701 transgenic locus of SEQ ID NO: 1, allelic variants thereof, or other variants thereof to obtain an INIR20 transgenic locus. In other embodiments, the OgRRS is found in non-transgenic DNA or transgenic DNA of the 3' junction polynucleotide of the MON87701 transgenic locus of any one of SEQ ID NO: 1, allelic variants thereof, or other variants thereof and the corresponding CgRRS is introduced into the transgenic DNA, non-transgenic DNA, or a combination thereof in the 5' junction polynucleotide of the transgenic locus of SEQ ID NO: 1, allelic variants thereof, or other variants thereof to obtain an INIR20 transgenic locus.

In certain embodiments, the CgRRS is comprised in whole or in part of an exogenous DNA molecule that is introduced into a DNA junction polynucleotide by genome editing. In certain embodiments, the guide RNA hybridization site of the CgRRS is operably linked to a pre-existing PAM site in the transgenic DNA or non-transgenic DNA of the transgenic plant genome. In other embodiments, the guide RNA hybridization site of the CgRRS is operably linked to a new PAM site that is introduced in the DNA junction polynucleotide by genome editing. A CgRRS can be located in non-transgenic plant genomic DNA of a DNA junction polynucleotide of an INIR20 transgenic locus, in transgenic DNA of a DNA junction polynucleotide of an INIR20 transgenic locus or can span the junction of the transgenic and non-transgenic DNA of a DNA junction polynucleotide of an INIR20 transgenic locus. An OgRRS can likewise be located in non-transgenic plant genomic DNA of a DNA junction polynucleotide of an INIR20 transgenic locus, in transgenic DNA of a DNA junction polynucleotide of an INIR20 transgenic locus, or can span the junction of the transgenic and non-transgenic DNA of a DNA junction polynucleotide of an INIR20 transgenic locus Methods provided herein can be used in a variety of breeding schemes to obtain elite crop plants comprising subsets of desired modified transgenic loci comprising an OgRRS and a CgRRS operably linked to junction polynucleotide sequences and transgenic loci excision sites where undesired transgenic loci or portions thereof have been removed (e.g., by use of the OgRRS and a CgRRS). Such methods are useful at least insofar as they allow for production of distinct useful donor plant lines each having unique sets of modified transgenic loci and, in some instances, targeted genetic changes that are tailored for distinct geographies and/or product offerings. In an illustrative and non-limiting example, a different product lines comprising transgenic loci conferring only two of three types of herbicide tolerance (e.g., glyphosate, glufosinate, and dicamba) can be obtained from a single donor line comprising three distinct transgenic loci conferring resistance to all three herbicides. In certain aspects, plants comprising the subsets of undesired transgenic loci and transgenic loci excision sites can further comprise targeted genetic changes. Such elite crop plants can be inbred plant lines or can be hybrid plant lines. In certain embodiments, at least two transgenic loci (e.g., transgenic loci including an INIR20 and another modified transgenic locus wherein an OgRRS and a CgRRS site is operably linked to a first and a second junction sequence and optionally a selectable marker gene and/or non-essential DNA are deleted) are introgressed into a desired donor line comprising elite crop plant germplasm and then subjected to genome editing molecules to recover plants comprising one of the two introgressed transgenic loci as well as a transgenic loci excision site introduced by excision of the other transgenic locus or portion thereof by the genome editing molecules. In certain embodiments, the genome editing molecules can be used to remove a transgenic locus and introduce targeted genetic changes in the crop plant genome. Introgression can be achieved by backcrossing plants comprising the transgenic loci to a recurrent parent comprising the desired elite germplasm and selecting progeny with the transgenic loci and recurrent parent germplasm. Such backcrosses can be repeated and/or supplemented by molecular assisted breeding techniques using SNP or other nucleic acid markers to select for recurrent parent germplasm until a desired recurrent parent percentage is obtained (e.g., at least about 95%, 96%, 97%, 98%, or 99% recurrent parent percentage). A non-limiting, illustrative depiction of a scheme for obtaining plants with both subsets of transgenic loci and the targeted genetic changes is shown in the FIG. 2 (bottom "Alternative" panel), where two or more of the transgenic loci ("Event" in FIG. 2) are provided in Line A and then moved into elite crop plant germplasm by introgression. In the non-limiting FIG. 2 illustration, introgression can be achieved by crossing a "Line A" comprising two or more of the modified transgenic loci to the elite germplasm and then backcrossing progeny of the cross comprising the transgenic loci to the elite germplasm as the recurrent parent) to obtain a "Universal Donor" (e.g., Line A+ in FIG. 2) comprising two or more of the modified transgenic loci. This elite germplasm containing the modified transgenic loci (e.g., "Universal Donor" of FIG. 2) can then be subjected to genome editing molecules which can excise at least one of the transgenic loci ("Event Removal" in FIG. 2) and introduce other targeted genetic changes ("GE" in FIG. 2) in the genomes of the elite crop plants containing one of the transgenic loci and a transgenic locus excision site corresponding to the removal site of one of the transgenic loci. Such selective excision of transgenic loci or portion thereof can be effected by contacting the genome of the plant comprising two transgenic loci with gene editing molecules (e.g., RdDe and gRNAs, TALENS, and/or ZFN) which recognize one transgenic loci but not another transgenic loci. Genome editing molecules that provide for selective excision of a first modified transgenic locus comprising an OgRRS and a CgRRS include a gRNA that hybridizes to the OgRRS and CgRRS of the first modified transgenic locus and an RdDe that recognizes the gRNA/OgRRS and gRNA/CgRRS complexes. Distinct plant lines with different subsets of transgenic loci and desired targeted genetic changes are thus recovered (e.g., "Line B-1," "Line B-2," and "Line B-3" in FIG. 2). In certain embodiments, it is also desirable to bulk up populations of inbred elite crop plants or their seed comprising the subset of transgenic loci and a transgenic locus excision site by selfing. In certain embodiments, inbred progeny of the selfed soybean plants comprising the INIR20 transgenic loci can be used as a pollen donor or recipient for hybrid seed production. Such hybrid seed and the progeny grown therefrom can comprise a subset of desired transgenic loci and a transgenic loci excision site.

Hybrid plant lines comprising elite crop plant germplasm, at least one transgenic locus and at least one transgenic locus excision site, and in certain aspects, additional targeted genetic changes are also provided herein. Methods for production of such hybrid seed can comprise crossing elite crop plant lines where at least one of the pollen donor or recipient comprises at least the transgenic locus and a transgenic locus excision site and/or additional targeted genetic changes. In certain embodiments, the pollen donor and recipient will comprise germplasm of distinct heterotic groups and provide hybrid seed and plants exhibiting heterosis. In certain embodiments, the pollen donor and recipient can each comprise a distinct transgenic locus which confers either a distinct trait (e.g., herbicide tolerance or insect resistance), a different type of trait (e.g., tolerance to distinct herbicides or to distinct insects such as coleopteran insects), or a different mode-of-action for the same trait (e.g., resistance to lepidopteran insects by two distinct modes-of-action or resistance to lepidopteran insects by two distinct modes-of-action). In certain embodiments, the pollen recipient will be rendered male sterile or conditionally male sterile. Methods for inducing male sterility or conditional male sterility include emasculation (e.g., detasseling), cytoplasmic male sterility, chemical hybridizing agents or systems, a transgenes or transgene systems, and/or mutation(s) in one or more endogenous plant genes. Descriptions of various male sterility systems that can be adapted for use with the elite crop plants provided herein are described in Wan et al. Molecular Plant; 12, 3, (2019):321-342 as well as in U.S. Pat. No. 8,618,358; US 20130031674; and US 2003188347.

In certain embodiments, edited transgenic plant genomes, transgenic plant cells, parts, or plants containing those genomes, and DNA molecules obtained therefrom, can comprise a desired subset of transgenic loci and/or comprise at least one transgenic locus excision site. In certain embodiments, a segment comprising an INIR20 transgenic locus comprising an OgRRS in non-transgenic DNA of a $1^{st}$ junction polynucleotide sequence and a CgRRS in a $2^{nd}$ junction polynucleotide sequence is deleted with a gRNA and RdDe that recognize the OgRRS and the CgRRS to produce an INIR20 transgenic locus excision site. For example, an INIR20 transgenic locus set forth in SEQ ID NO: 3 or 15 can be deleted with a Cas12a RdDe (e.g. the Cas12a of SEQ ID NO:16) and a gRNA comprising an RNA encoded by SEQ ID NO: 11. In certain embodiments, the transgenic locus excision site can comprise a contiguous segment of DNA comprising at least 10 base pairs of DNA that is telomere proximal to the deleted segment of the transgenic locus and at least 10 base pairs of DNA that is centromere proximal to the deleted segment of the transgenic locus wherein the transgenic DNA (i.e., the heterologous DNA) that has been inserted into the crop plant genome has been deleted. In certain embodiments where a segment comprising a transgenic locus has been deleted, the transgenic locus excision site can comprise a contiguous segment of DNA comprising at least 10 base pairs DNA that is telomere proximal to the deleted segment of the transgenic locus and at least 10 base pairs of DNA that is centromere proximal DNA to the deleted segment of the transgenic locus wherein the heterologous transgenic DNA and at least 1, 2, 5, 10, 20, 50, or more base pairs of endogenous DNA located in a 5' junction sequence and/or in a 3' junction sequence of the original transgenic locus that has been deleted. In such embodiments where DNA comprising the transgenic locus is deleted, a transgenic locus excision site can comprise at least 10 base pairs of DNA that is telomere proximal to the deleted segment of the transgenic locus and at least 10 base pairs of DNA that is centromere proximal to the deleted segment of the transgenic locus wherein all of the transgenic DNA is absent and either all or less than all of the endogenous DNA flanking the transgenic DNA sequences are present. In certain embodiments where a segment consisting essentially of an original transgenic locus has been deleted, the transgenic locus excision site can be a contiguous segment of at least 10 base pairs of DNA that is telomere proximal to the deleted segment of the transgenic locus and at least 10 base pairs of DNA that is centromere proximal to the deleted segment of the transgenic locus wherein less than all of the heterologous transgenic DNA that has been inserted into the crop plant genome is excised. In certain aforementioned embodiments where a segment consisting essentially of an original transgenic locus has been deleted, the transgenic locus excision site can thus contain at least 1 base pair of DNA or 1 to about 2 or 5, 8, 10, 20, or 50 base pairs of DNA comprising the telomere proximal and/or centromere proximal heterologous transgenic DNA that has been inserted into the crop plant genome. In certain embodiments where a segment consisting of an original transgenic locus has been deleted, the transgenic locus excision site can contain a contiguous segment of DNA comprising at least 10 base pairs of DNA that is telomere proximal to the deleted segment of the transgenic locus and at least 10 base pairs of DNA that is centromere proximal to the deleted segment of the transgenic locus wherein the heterologous transgenic DNA that has been inserted into the crop plant genome is deleted. In certain embodiments where DNA consisting of the transgenic locus is deleted, a transgenic locus excision site can comprise at least 10 base pairs of DNA that is telomere proximal to the deleted segment of the transgenic locus and at least 10 base pairs of DNA that is centromere proximal to the deleted segment of the transgenic locus wherein all of the heterologous transgenic DNA that has been inserted into the crop plant genome is deleted and all of the endogenous DNA flanking the heterologous sequences of the transgenic locus is present. In any of the aforementioned embodiments or in other embodiments, the continuous segment of DNA comprising the transgenic locus excision site can further comprise an insertion of 1 to about 2, 5, 10, 20, or more nucleotides between the DNA that is telomere proximal to the deleted segment of the transgenic locus and the DNA that is centromere proximal to the deleted segment of the transgenic locus. Such insertions can result either from endogenous DNA repair and/or recombination activities at the double stranded breaks introduced at the excision site and/or from deliberate insertion of an oligonucleotide. Plants, edited plant genomes, biological samples, and DNA molecules (e.g., including isolated or purified DNA molecules) comprising the INIR20 transgenic loci excision sites are provided herein.

Figure 3C:
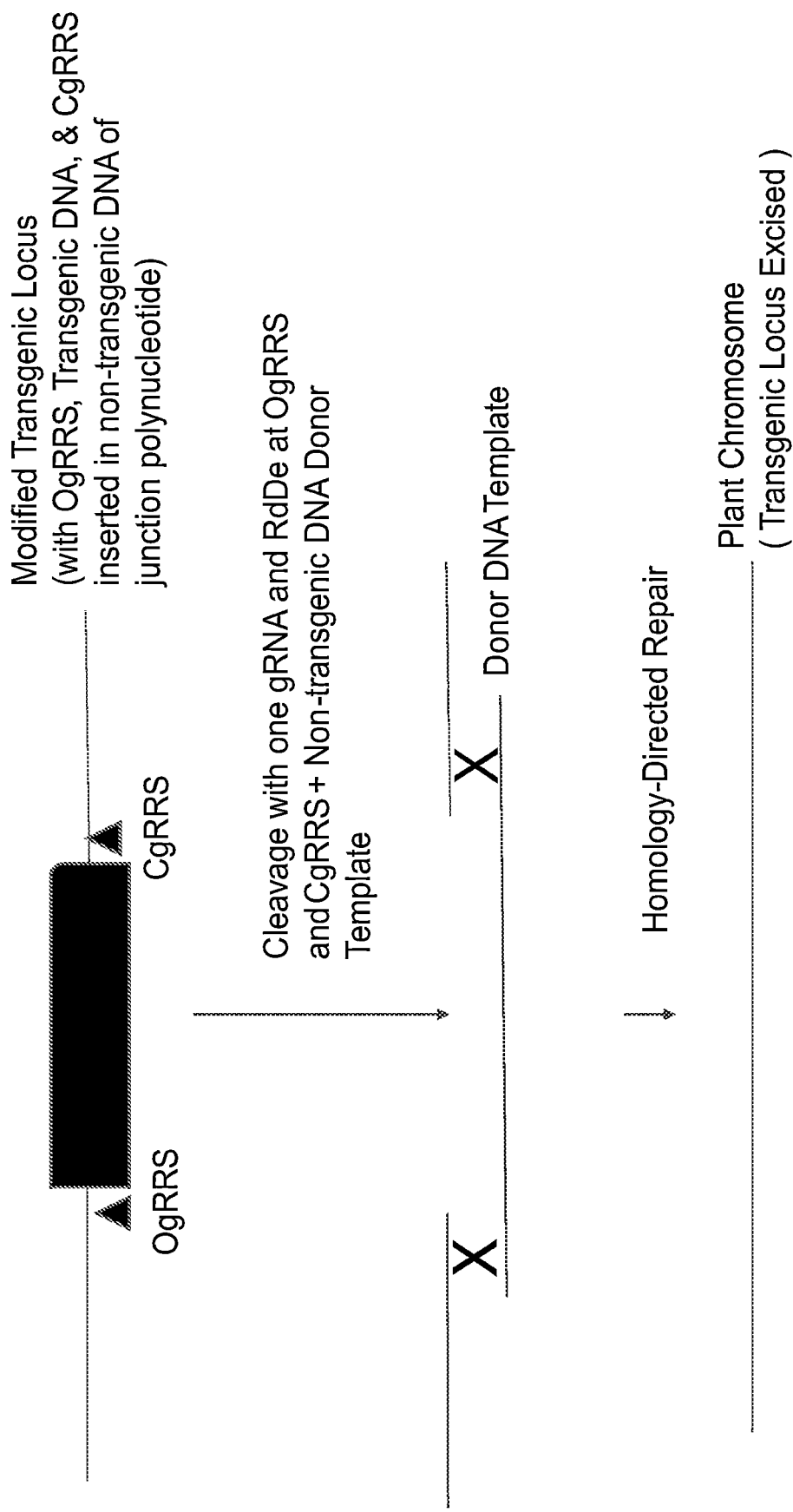

In other embodiments, a segment comprising a INIR20 transgenic locus (e.g., a transgenic locus comprising an OgRRS in non-transgenic DNA of a $1^{st}$ junction sequence and a CgRRS in a $2^{nd}$ junction sequence) can be deleted with a gRNA and RdDe that recognize the OgRRS and the CgRRS (e.g., the Cas12a RdDe of SEQ ID NO: 16 and a gRNA comprising an RNA encoded by SEQ ID NO: 11) and replaced with DNA comprising the endogenous non-transgenic plant genomic DNA present in the genome prior to transgene insertion. A non-limiting example of such replacements can be visualized in FIG. 3C, where the donor DNA template can comprise the endogenous non-transgenic plant genomic DNA present in the genome prior to transgene insertion along with sufficient homology to non-transgenic DNA on each side of the excision site to permit homology-directed repair. In certain embodiments, the endogenous non-transgenic plant genomic DNA present in the genome prior to transgene insertion can be at least partially restored. In certain embodiments, the endogenous non-transgenic plant genomic DNA present in the genome prior to transgene insertion can be essentially restored such that no more than about 5, 10, or 20 to about 50, 80, or 100 nucleotides are changed relative to the endogenous DNA at the essentially restored excision site.

In certain embodiments, edited transgenic plant genomes and transgenic plant cells, plant parts, or plants containing those edited genomes, comprising a modification of an original transgenic locus, where the modification comprises an OgRRS and a CgRRS which are operably linked to a $1^{st}$ and a $2^{nd}$ junction sequence, respectively or irrespectively, and optionally further comprise a deletion of a segment of the original transgenic locus. In certain embodiments, the modification comprises two or more separate deletions and/or there is a modification in two or more original transgenic plant loci. In certain embodiments, the deleted segment comprises, consists essentially of, or consists of a segment of non-essential DNA in the transgenic locus. Illustrative examples of non-essential DNA include but are not limited to synthetic cloning site sequences, duplications of transgene sequences; fragments of transgene sequences, and *Agrobacterium* right and/or left border sequences. In certain embodiments, the non-essential DNA is a duplication and/or fragment of a promoter sequence and/or is not the promoter sequence operably linked in the cassette to drive expression of a transgene. In certain embodiments, excision of the non-essential DNA improves a characteristic, functionality, and/or expression of a transgene of the transgenic locus or otherwise confers a recognized improvement in a transgenic plant comprising the edited transgenic plant genome. In certain embodiments, the non-essential DNA does not comprise DNA encoding a selectable marker gene. In certain embodiments of an edited transgenic plant genome, the modification comprises a deletion of the non-essential DNA and a deletion of a selectable marker gene. The modification producing the edited transgenic plant genome could occur by excising both the non-essential DNA and the selectable marker gene at the same time, e.g., in the same modification step, or the modification could occur step-wise. For example, an edited transgenic plant genome in which a selectable marker gene has previously been removed from the transgenic locus can comprise an original transgenic locus from which a non-essential DNA is further excised and vice versa. In certain embodiments, the modification comprising deletion of the non-essential DNA and deletion of the selectable marker gene comprises excising a single segment of the original transgenic locus that comprises both the non-essential DNA and the selectable marker gene. Such modification would result in one excision site in the edited transgenic genome corresponding to the deletion of both the non-essential DNA and the selectable marker gene. In certain embodiments, the modification comprising deletion of the non-essential DNA and deletion of the selectable marker gene comprises excising two or more segments of the original transgenic locus to achieve deletion of both the non-essential DNA and the selectable marker gene. Such modification would result in at least two excision sites in the edited transgenic genome corresponding to the deletion of both the non-essential DNA and the selectable marker gene. In certain embodiments of an edited transgenic plant genome, prior to excision, the segment to be deleted is flanked by operably linked protospacer adjacent motif (PAM) sites in the original or unmodified transgenic locus and/or the segment to be deleted encompasses an operably linked PAM site in the original or unmodified transgenic locus. In certain embodiments, following excision of the segment, the resulting edited transgenic plant genome comprises PAM sites flanking the deletion site in the modified transgenic locus. In certain embodiments of an edited transgenic plant genome, the modification comprises a modification of a MON87701 transgenic locus.

In certain embodiments, improvements in a transgenic plant locus are obtained by introducing a new cognate guide RNA recognition site (CgRRS) which is operably linked to a DNA junction polynucleotide of the transgenic locus in the transgenic plant genome. Such CgRRS sites can be recognized by RdDe, and a single suitable guide RNA directed to the CgRRS and the originator gRNA Recognition Site (OgRRS) to provide for cleavage within the junction polynucleotides which flank an INIR20 transgenic locus. In certain embodiments, the CgRRS/gRNA and OgRRS/gRNA hybridization complexes are recognized by the same class of RdDe (e.g., Class 2 type II or Class 2 type V) or by the same RdDe (e.g., both the CgRRS/gRNA and OgRRS/gRNA hybridization complexes recognized by the same Cas9 or Cas 12 RdDe). Such CgRRS and OgRRS can be recognized by RdDe and suitable guide RNAs containing crRNA sufficiently complementary to the guide RNA hybridization site DNA sequences adjacent to the PAM site of the CgRRS and the OgRRS to provide for cleavage within or near the two junction polynucleotides. Suitable guide RNAs can be in the form of a single gRNA comprising a crRNA or in the form of a crRNA/tracrRNA complex. In the case of the OgRRS site, the PAM and guide RNA hybridization site are endogenous DNA polynucleotide molecules found in the plant genome. In certain embodiments where the CgRRS is introduced into the plant genome by genome editing, gRNA hybridization site polynucleotides introduced at the CgRRS are at least 17 or 18 nucleotides in length and are complementary to the crRNA of a guide RNA. In certain embodiments, the gRNA hybridization site sequence of the OgRRS and/or the CgRRS is about 17 or 18 to about 24 nucleotides in length. The gRNA hybridization site sequence of the OgRRS and the gRNA hybridization site of the CgRRS can be of different lengths or comprise different sequences so long as there is sufficient complementarity to permit hybridization by a single gRNA and recognition by a RdDe that recognizes and cleaves DNA at the gRNA/OgRRS and gRNA/CgRRS complex. In certain embodiments, the guide RNA hybridization site of the CgRRS comprise about a 17 or 18 to about 24 nucleotide sequence which is identical to the guide RNA hybridization site of the OgRRS. In other embodiments, the guide RNA hybridization site of the CgRRS comprise about a 17 or 18 to about 24 nucleotide sequence which has one, two, three, four, or five nucleotide insertions, deletions or substitutions when compared to the guide RNA hybridization site of the OgRRS. Certain CgRRS comprising a gRNA hybridization site containing has one, two, three, four, or five nucleotide insertions, deletions or substitutions when compared to the guide RNA hybridization site of the OgRRS can undergo hybridization with a gRNA which is complementary to the OgRRS gRNA hybridization site and be cleaved by certain RdDe. Examples of mismatches between gRNAs and guide RNA hybridization sites which allow for RdDe recognition and cleavage include mismatches resulting from both nucleotide insertions and deletions in the DNA which is hybridized to the gRNA (e.g., Lin et al., doi: 10.1093/nar/gku402). In certain embodiments, an operably linked PAM site is co-introduced with the gRNA hybridization site polynucleotide at the CgRRS. In certain embodiments, the gRNA hybridization site polynucleotides are introduced at a position adjacent to a resident endogenous PAM sequence in the junction polynucleotide sequence to form a CgRRS where the gRNA hybridization site polynucleotides are operably linked to the endogenous PAM site. In certain embodiments, non-limiting features of the OgRRS, CgRRS, and/or the gRNA hybridization site polynucleotides thereof include: (i) absence of significant homology or sequence identity (e.g., less than 50% sequence identity across the entire length of the OgRRS, CgRRS, and/or the gRNA hybridization site sequence) to any other endogenous or transgenic sequences present in the transgenic plant genome or in other transgenic genomes of the soybean plant being transformed and edited; (ii) absence of significant homology or sequence identity (e.g., less than 50% sequence identity across the entire length of the sequence) of a sequence of a first OgRRS and a first CgRRS to a second OgRRS and a second CgRRS which are operably linked to junction polynucleotides of a distinct transgenic locus; (iii) the presence of some sequence identity (e.g., about 25%, 40%, or 50% to about 60%, 70%, or 80%) between the OgRRS sequence and endogenous sequences present at the site where the CgRRS sequence is introduced; and/or (iv) optimization of the gRNA hybridization site polynucleotides for recognition by the RdDe and guide RNA when used in conjunction with a particular PAM sequence. In certain embodiments, the first and second OgRRS as well as the first and second CgRRS are recognized by the same class of RdDe (e.g., Class 2 type II or Class 2 type V) or by the same RdDe (e.g., Cas9 or Cas 12 RdDe). In certain embodiments, the first OgRRS site in a first junction polynucleotide and the CgRRS introduced in the second junction polynucleotide to permit excision of a first transgenic locus by a first single guide RNA and a single RdDe. Such nucleotide insertions or genome edits used to introduce CgRRS in a transgenic plant genome can be effected in the plant genome by using gene editing molecules (e.g., RdDe and guide RNAs, RNA dependent nickases, and guide RNAs, Zinc Finger nucleases or nickases, or TALE nucleases or nickases) which introduce blunt double stranded breaks or staggered double stranded breaks in the DNA junction polynucleotides. In the case of DNA insertions, the genome editing molecules can also in certain embodiments further comprise a donor DNA template or other DNA template which comprises the heterologous nucleotides for insertion to form the CgRRS. Guide RNAs can be directed to the junction polynucleotides by using a pre-existing PAM site located within or adjacent to a junction polynucleotide of the transgenic locus. Non-limiting examples of such pre-existing PAM sites present in junction polynucleotides, which can be used either in conjunction with an inserted heterologous sequence to form a CgRRS or which can be used to create a double stranded break to insert or create a CgRRS, include PAM sites recognized by a Cas12a enzyme. Non-limiting examples where a CgRRS is created in a DNA sequence are illustrated in Example 2.

Transgenic loci comprising OgRRS and CgRRS in a first and a second junction polynucleotides can be excised from the genomes of transgenic plants by contacting the transgenic loci with RdDe or RNA directed nickases, and a suitable guide RNA directed to the OgRRS and CgRRS (e.g., the Cas12a RdDe of SEQ ID NO: 16 and a gRNA comprising an RNA encoded by SEQ ID NO: 11). A non-limiting example where a modified transgenic locus is excised from a plant genome by use of a gRNA and an RdDe that recognizes an OgRRS/gRNA and a CgRRS/gRNA complex and introduces dsDNA breaks in both junction polynucleotides and repaired by NHEJ is depicted in FIG. 3B. In the depicted example set forth in FIG. 3B, the OgRRS site and the CgRRS site are absent from the plant chromosome comprising the transgene excision site that results from the process. In other embodiments provided herein where a modified transgenic locus is excised from a plant genome by use of a gRNA and an RdDe that recognizes an OgRRS/gRNA and a CgRRS/gRNA complex and repaired by NHEJ or microhomology-mediated end joining (MMEJ), the OgRRS and/or other non-transgenic sequences that were originally present prior to transgene insertion are partially or essentially restored.

In certain embodiments, edited transgenic plant genomes provided herein can comprise additional new introduced transgenes (e.g., expression cassettes) inserted into the transgenic locus of a given event. Introduced transgenes inserted at the transgenic locus of an event subsequent to the event's original isolation can be obtained by inducing a double stranded break at a site within an original transgenic locus (e.g., with genome editing molecules including an RdDe and suitable guide RNA(s); a suitable engineered zinc-finger nuclease; a TALEN protein and the like) and providing an exogenous transgene in a donor DNA template which can be integrated at the site of the double stranded break (e.g. by homology-directed repair (HDR) or by non-homologous end-joining (NHEJ)). In certain embodiments, an OgRRS and a CgRRS located in a $1^{st}$ junction polynucleotide and a $2^{nd}$ junction polynucleotide, respectively, can be used to delete the transgenic locus and replace it with one or more new expression cassettes. In certain embodiments, such deletions and replacements are effected by introducing dsDNA breaks in both junction polynucleotides and providing the new expression cassettes on a donor DNA template (e.g., in FIG. 3C, the donor DNA template can comprise an expression cassette flanked by DNA homologous to non-transgenic DNA located telomere proximal and centromere proximal to the excision site). Suitable expression cassettes for insertion include DNA molecules comprising promoters which are operably linked to DNA encoding proteins and/or RNA molecules which confer useful traits which are in turn operably linked to polyadenylation sites or terminator elements. In certain embodiments, such expression cassettes can also comprise 5' UTRs, 3' UTRs, and/or introns. Useful traits include biotic stress tolerance (e.g., insect resistance, nematode resistance, or disease resistance), abiotic stress tolerance (e.g., heat, cold, drought, and/or salt tolerance), herbicide tolerance, and quality traits (e.g., improved fatty acid compositions, protein content, starch content, and the like). Suitable expression cassettes for insertion include expression cassettes which confer insect resistance, herbicide tolerance, biofuel use, or male sterility traits contained in any of the transgenic events set forth in US Patent Application Public. Nos. 20090038026, 20130031674, 20150361446, 20170088904, 20150267221, 201662346688, and 20200190533 as well as in U.S. Pat. Nos. 6,342,660, 7,323,556, 6,040,497, 8,759,618, 7,157,281, 6,852,915, 7,705,216, 10,316,330, 8,618,358, 8,450,561, 8,212,113, 9,428,765, 9,540,655, 7,897,748, 8,273,959, 8,093,453, 8,901,378, 9,994,863, 7,928,296, and 8,466,346, each of which are incorporated herein by reference in their entireties.

In certain embodiments, INIR20 plants provided herein, including plants with one or more transgenic loci, modified transgenic loci, and/or comprising transgenic loci excision sites can further comprise one or more targeted genetic changes introduced by one or more of gene editing molecules or systems. Also provided are methods where the targeted genetic changes are introduced and one or more transgenic loci are removed from plants either in series or in parallel (e.g., as set forth in the non-limiting illustration in FIG. 2, bottom "Alternative" panel, where "GE" can represent targeted genetic changes induced by gene editing molecules and "Event Removal" represents excision of one or more transgenic loci with gene editing molecules). Such targeted genetic changes include those conferring traits such as improved yield, improved food and/or feed characteristics (e.g., improved oil, starch, protein, or amino acid quality or quantity), improved nitrogen use efficiency, improved biofuel use characteristics (e.g., improved ethanol production), male sterility/conditional male sterility systems (e.g., by targeting endogenous MS26, MS45 and MSCA1 genes), herbicide tolerance (e.g., by targeting endogenous ALS, EPSPS, HPPD, or other herbicide target genes), delayed flowering, non-flowering, increased biotic stress resistance (e.g., resistance to insect, nematode, bacterial, or fungal damage), increased abiotic stress resistance (e.g., resistance to drought, cold, heat, metal, or salt), enhanced lodging resistance, enhanced growth rate, enhanced biomass, enhanced tillering, enhanced branching, delayed flowering time, delayed senescence, increased flower number, improved architecture for high density planting, improved photosynthesis, increased root mass, increased cell number, improved seedling vigor, improved seedling size, increased rate of cell division, improved metabolic efficiency, and increased meristem size in comparison to a control plant lacking the targeted genetic change. Types of targeted genetic changes that can be introduced include insertions, deletions, and substitutions of one or more nucleotides in the crop plant genome. Sites in endogenous plant genes for the targeted genetic changes include promoter, coding, and non-coding regions (e.g., 5' UTRs, introns, splice donor and acceptor sites and 3' UTRs). In certain embodiments, the targeted genetic change comprises an insertion of a regulatory or other DNA sequence in an endogenous plant gene. Non-limiting examples of regulatory sequences which can be inserted into endogenous plant genes with gene editing molecules to effect targeted genetic changes which confer useful phenotypes include those set forth in US Patent Application Publication 20190352655, which is incorporated herein by reference in its entirety, such as: (a) auxin response element (AuxRE) sequence; (b) at least one D1-4 sequence (Ulmasov et al. (1997) Plant Cell, 9:1963-1971), (c) at least one DR5 sequence (Ulmasov et al. (1997) Plant Cell, 9:1963-1971); (d) at least one m5-DR5 sequence (Ulmasov et al. (1997) Plant Cell, 9:1963-1971); (e) at least one P3 sequence; (f) a small RNA recognition site sequence bound by a corresponding small RNA (e.g., an siRNA, a microRNA (miRNA), a trans-acting siRNA as described in U.S. Pat. No. 8,030,473, or a phased sRNA as described in U.S. Pat. No. 8,404,928; both of these cited patents are incorporated by reference herein); (g) a microRNA (miRNA) recognition site sequence; (h) the sequence recognizable by a specific binding agent includes a microRNA (miRNA) recognition sequence for an engineered miRNA wherein the specific binding agent is the corresponding engineered mature miRNA; (i) a transposon recognition sequence; (j) a sequence recognized by an ethylene-responsive element binding-factor-associated amphiphilic repression (EAR) motif; (k) a splice site sequence (e.g., a donor site, a branching site, or an acceptor site; see, for example, the splice sites and splicing signals set forth in the internet site lemur[dot]amu[dot]edu[dot]pl/share/ERISdb/home.html); (1) a recombinase recognition site sequence that is recognized by a site-specific recombinase; (m) a sequence encoding an RNA or amino acid aptamer or an RNA riboswitch, the specific binding agent is the corresponding ligand, and the change in expression is upregulation or downregulation; (n) a hormone responsive element recognized by a nuclear receptor or a hormone-binding domain thereof; (o) a transcription factor binding sequence; and (p) a polycomb response element (see Xiao et al. (2017) Nature Genetics, 49:1546-1552, doi: 10.1038/ng.3937). Non limiting examples of target soybean genes that can be subjected to targeted gene edits to confer useful traits include: (a) ZmIPK1 (herbicide tolerant and phytate reduced soybean; Shukla et al., Nature. 2009; 459:437-41); (b) ZmGL2 (reduced epicuticular wax in leaves; Char et al. Plant Biotechnol J. 2015; 13:1002); (c) ZmMTL (induction of haploid plants; Kelliher et al. Nature. 2017; 542:105); (d) Wx1 (high amylopectin content; US 20190032070; incorporated herein by reference in its entirety); (e) TMS5 (thermosensitive male sterile; Li et al. J Genet Genomics. 2017; 44:465-8); (0 ALS (herbicide tolerance; Svitashev et al.; Plant Physiol. 2015; 169:931-45); and (g) ARGOS8 (drought stress tolerance; Shi et al., Plant Biotechnol J. 2017; 15:207-16). Non-limiting examples of target genes in crop plants including soybean which can be subjected to targeted genetic changes which confer useful phenotypes include those set forth in US Patent Application Nos. 20190352655, 20200199609, 20200157554, and 20200231982, which are each incorporated herein in their entireties; and Zhang et al. (Genome Biol. 2018; 19: 210).

In certain embodiments, it will be desirable to use genome editing molecules to make modified transgenic loci by introducing a CgRRS into the transgenic loci, to excise modified transgenic loci comprising an OgRRS and a CgRRS, and/or to make targeted genetic changes in elite crop plant or other germplasm. In certain embodiments, the genome edits can be effected in regenerable plant parts (e.g., plant embryos) of elite crop plants by transient provision of gene editing molecules or polynucleotides encoding the same and do not necessarily require incorporating a selectable marker gene into the plant genome (e.g., US 20160208271 and US 20180273960, both incorporated herein by reference in their entireties; Svitashev et al. Nat Commun. 2016; 7:13274).

Gene editing molecules of use in methods provided herein include molecules capable of introducing a double-strand break ("DSB") or single-strand break ("SSB") in double-stranded DNA, such as in genomic DNA or in a target gene located within the genomic DNA as well as accompanying guide RNA or donor DNA template polynucleotides. Examples of such gene editing molecules include: (a) a nuclease comprising an RNA-guided nuclease, an RNA-guided DNA endonuclease or RNA directed DNA endonuclease (RdDe), a class 1 CRISPR type nuclease system, a type II Cas nuclease, a Cas9, a nCas9 nickase, a type V Cas nuclease, a Cas12a nuclease, a nCas12a nickase, a Cas12d (CasY), a Cas12e (CasX), a Cas12b (C2c1), a Cas12c (C2c3), a Cas12i, a Cas12j, a Cas14, an engineered nuclease, a codon-optimized nuclease, a zinc-finger nuclease (ZFN) or nickase, a transcription activator-like effector nuclease (TAL-effector nuclease or TALEN) or nickase (TALE-nickase), an Argonaute, and a meganuclease or engineered meganuclease; (b) a polynucleotide encoding one or more nucleases capable of effectuating site-specific alteration (including introduction of a DSB or SSB) of a target nucleotide sequence; (c) a guide RNA (gRNA) for an RNA-guided nuclease, or a DNA encoding a gRNA for an RNA-guided nuclease; (d) donor DNA template polynucleotides; and (e) other DNA templates (dsDNA, ssDNA, or combinations thereof) suitable for insertion at a break in genomic DNA (e.g., by non-homologous end joining (NHEJ) or microhomology-mediated end joining (MMEJ).

CRISPR-type genome editing can be adapted for use in the plant cells and methods provided herein in several ways. CRISPR elements, e.g., gene editing molecules comprising CRISPR endonucleases and CRISPR guide RNAs including single guide RNAs or guide RNAs in combination with tracrRNAs or scoutRNA, or polynucleotides encoding the same, are useful in effectuating genome editing without remnants of the CRISPR elements or selective genetic markers occurring in progeny. In certain embodiments, the CRISPR elements are provided directly to the eukaryotic cell (e.g., plant cells), systems, methods, and compositions as isolated molecules, as isolated or semi-purified products of a cell free synthetic process (e.g., in vitro translation), or as isolated or semi-purified products of in a cell-based synthetic process (e.g., such as in a bacterial or other cell lysate). In certain embodiments, genome-inserted CRISPR elements are useful in plant lines adapted for use in the methods provide herein. In certain embodiments, plants or plant cells used in the systems, methods, and compositions provided herein can comprise a transgene that expresses a CRISPR endonuclease (e.g., a Cas9, a Cpf1-type or other CRISPR endonuclease). In certain embodiments, one or more CRISPR endonucleases with unique PAM recognition sites can be used. Guide RNAs (sgRNAs or crRNAs and a tracrRNA) used to form an RNA-guided endonuclease/ guide RNA complex can specifically bind via hybridization to gRNA hybridization site sequences (i.e., protospacer sequences) in the gDNA target site that are adjacent to a protospacer adjacent motif (PAM) sequence. The type of RNA-guided endonuclease typically informs the location of suitable PAM sites and design of crRNAs or sgRNAs. G-rich PAM sites, e.g., 5'-NGG are typically targeted for design of crRNAs or sgRNAs used with Cas9 proteins. Examples of PAM sequences include 5'-NGG (*Streptococcus pyogenes*), 5'-NNAGAA (*Streptococcus thermophilus* CRISPR1), 5'-NGGNG (*Streptococcus thermophilus* CRISPR3), 5'-NNGRRT or 5'-NNGRR (*Staphylococcus aureus* Cas9, SaCas9), and 5'-NNNGATT (*Neisseria meningitidis*). T-rich PAM sites (e.g., 5'-TTN or 5'-TTTV, where "V" is A, C, or G) are typically targeted for design of crRNAs or sgRNAs used with Cas12a proteins (e.g., the Cas12a protein of SEQ ID NO: 16). In some instances, Cas12a can also recognize a 5'-CTA PAM motif. Other examples of potential Cas12a PAM sequences include TTN, CTN, TCN, CCN, TTTN, TCTN, TTCN, CTTN, ATTN, TCCN, TTGN, GTTN, CCCN, CCTN, TTAN, TCGN, CTCN, ACTN, GCTN, TCAN, GCCN, and CCGN (wherein N is defined as any nucleotide). Cpf1 (i.e., Cas12a) endonuclease and corresponding guide RNAs and PAM sites are disclosed in US Patent Application Publication 2016/0208243 A1, which is incorporated herein by reference for its disclosure of DNA encoding Cpf1 endonucleases and guide RNAs and PAM sites. Introduction of one or more of a wide variety of CRISPR guide RNAs that interact with CRISPR endonucleases integrated into a plant genome or otherwise provided to a plant is useful for genetic editing for providing desired phenotypes or traits, for trait screening, or for gene editing mediated trait introgression (e.g., for introducing a trait into a new genotype without backcrossing to a recurrent parent or with limited backcrossing to a recurrent parent). Multiple endonucleases can be provided in expression cassettes with the appropriate promoters to allow multiple genome site editing.

CRISPR technology for editing the genes of eukaryotes is disclosed in US Patent Application Publications 2016/0138008A1 and US2015/0344912A1, and in U.S. Pat. Nos. 8,697,359, 8,771,945, 8,945,839, 8,999,641, 8,993,233, 8,895,308, 8,865,406, 8,889,418, 8,871,445, 8,889,356, 8,932,814, 8,795,965, and 8,906,616. Cpf1 endonuclease and corresponding guide RNAs and PAM sites are disclosed in US Patent Application Publication 2016/0208243 A1. Other CRISPR nucleases useful for editing genomes include Cas12b and Cas12c (see Shmakov et al. (2015) Mol. Cell, 60:385-397; Harrington et al. (2020) Molecular Cell doi: 10.1016/j.molcel.2020.06.022) and CasX and CasY (see Burstein et al. (2016) Nature, doi:10.1038/nature21059; Harrington et al. (2020) Molecular Cell doi:10.1016/j.molcel.2020.06.022), or Cas12j (Pausch et al, (2020) Science 10.1126/science.abb1400). Plant RNA promoters for expressing CRISPR guide RNA and plant codon-optimized CRISPR Cas9 endonuclease are disclosed in International Patent Application PCT/US2015/018104 (published as WO 2015/131101 and claiming priority to U.S. Provisional Patent Application 61/945,700). Methods of using CRISPR technology for genome editing in plants are disclosed in US Patent Application Publications US 2015/0082478A1 and US 2015/0059010A1 and in International Patent Application PCT/US2015/038767 A1 (published as WO 2016/007347 and claiming priority to U.S. Provisional Patent Application 62/023,246). All of the patent publications referenced in this paragraph are incorporated herein by reference in their entirety. In certain embodiments, an RNA-guided endonuclease that leaves a blunt end following cleavage of the target site is used. Blunt-end cutting RNA-guided endonucleases include Cas9, Cas12c, and Cas 12h (Yan et al., 2019). In certain embodiments, an RNA-guided endonuclease that leaves a staggered single stranded DNA overhanging end following cleavage of the target site following cleavage of the target site is used. Staggered-end cutting RNA-guided endonucleases include Cas12a, Cas12b, and Cas12e.

The methods can also use sequence-specific endonucleases or sequence-specific endonucleases and guide RNAs that cleave a single DNA strand in a dsDNA target site. Such cleavage of a single DNA strand in a dsDNA target site is also referred to herein and elsewhere as "nicking" and can be effected by various "nickases" or systems that provide for nicking. Nickases that can be used include nCas9 (Cas9 comprising a D10A amino acid substitution), nCas12a (e.g., Cas12a comprising an R1226A amino acid substitution; Yamano et al., 2016), Cas12i (Yan et al. 2019), a zinc finger nickase e.g., as disclosed in Kim et al., 2012), a TALE nickase (e.g., as disclosed in Wu et al., 2014), or a combination thereof. In certain embodiments, systems that provide for nicking can comprise a Cas nuclease (e.g., Cas9 and/or Cas12a) and guide RNA molecules that have at least one base mismatch to DNA sequences in the target editing site (Fu et al., 2019). In certain embodiments, genome modifications can be introduced into the target editing site by creating single stranded breaks (i.e., "nicks") in genomic locations separated by no more than about 10, 20, 30, 40, 50, 60, 80, 100, 150, or 200 base pairs of DNA. In certain illustrative and non-limiting embodiments, two nickases (i.e., a CAS nuclease which introduces a single stranded DNA break including nCas9, nCas12a, Cas12i, zinc finger nickases, TALE nickases, combinations thereof, and the like) or nickase systems can directed to make cuts to nearby sites separated by no more than about 10, 20, 30, 40, 50, 60, 80 or 100 base pairs of DNA. In instances where an RNA guided nickase and an RNA guide are used, the RNA guides are adjacent to PAM sequences that are sufficiently close (i.e., separated by no more than about 10, 20, 30, 40, 50, 60, 80, 100, 150, or 200 base pairs of DNA). For the purposes of gene editing, CRISPR arrays can be designed to contain one or multiple guide RNA sequences corresponding to a desired target DNA sequence; see, for example, Cong et al. (2013) Science, 339:819-823; Ran et al. (2013) Nature Protocols, 8:2281-2308. At least 16 or 17 nucleotides of gRNA sequence are required by Cas9 for DNA cleavage to occur; for Cpf1 at least 16 nucleotides of gRNA sequence are needed to achieve detectable DNA cleavage and at least 18 nucleotides of gRNA sequence were reported necessary for efficient DNA cleavage in vitro; see Zetsche et al. (2015) Cell, 163:759-771. In practice, guide RNA sequences are generally designed to have a length of 17-24 nucleotides (frequently 19, 20, or 21 nucleotides) and exact complementarity (i.e., perfect base-pairing) to the targeted gene or nucleic acid sequence; guide RNAs having less than 100% complementarily to the target sequence can be used (e.g., a gRNA with a length of 20 nucleotides and 1-4 mismatches to the target sequence) but can increase the potential for off-target effects. The design of effective guide RNAs for use in plant genome editing is disclosed in US Patent Application Publication 2015/0082478 A1, the entire specification of which is incorporated herein by reference. More recently, efficient gene editing has been achieved using a chimeric "single guide RNA" ("sgRNA"), an engineered (synthetic) single RNA molecule that mimics a naturally occurring crRNA-tracrRNA complex and contains both a tracrRNA (for binding the nuclease) and at least one crRNA (to guide the nuclease to the sequence targeted for editing); see, for example, Cong et al. (2013) Science, 339:819-823; Xing et al. (2014) BMC Plant Biol., 14:327-340. Chemically modified sgRNAs have been demonstrated to be effective in genome editing; see, for example, Hendel et al. (2015) *Nature Biotechnol.*, 985-991. The design of effective gRNAs for use in plant genome editing is disclosed in US Patent Application Publication 2015/0082478 A1, the entire specification of which is incorporated herein by reference.

Genomic DNA may also be modified via base editing. Both adenine base editors (ABE) which convert A/T base pairs to G/C base pairs in genomic DNA as well as cytosine base pair editors (CBE) which effect C to T substitutions can be used in certain embodiments of the methods provided herein. In certain embodiments, useful ABE and CBE can comprise genome site specific DNA binding elements (e.g., RNA-dependent DNA binding proteins including catalytically inactive Cas9 and Cas12 proteins or Cas9 and Cas12 nickases) operably linked to adenine or cytidine deaminases and used with guide RNAs which position the protein near the nucleotide targeted for substitution. Suitable ABE and CBE disclosed in the literature (Kim, Nat Plants, 2018 March; 4(3):148-151) can be adapted for use in the methods set forth herein. In certain embodiments, a CBE can comprise a fusion between a catalytically inactive Cas9 (dCas9) RNA dependent DNA binding protein fused to a cytidine deaminase which converts cytosine (C) to uridine (U) and selected guide RNAs, thereby effecting a C to T substitution; see Komor et al. (2016) *Nature*, 533:420-424. In other embodiments, C to T substitutions are effected with Cas9 nickase [Cas9n(D10A)] fused to an improved cytidine deaminase and optionally a bacteriophage Mu dsDNA (double-stranded DNA) end-binding protein Gam; see Komor et al., *Sci Adv.* 2017 August; 3(8): eaao4774. In other embodiments, adenine base editors (ABEs) comprising an adenine deaminase fused to catalytically inactive Cas9 (dCas9) or a Cas9 D10A nickase can be used to convert A/T base pairs to G/C base pairs in genomic DNA (Gaudelli et al., (2017) *Nature* 551(7681):464-471.

In certain embodiments, zinc finger nucleases or zinc finger nickases can also be used in the methods provided herein. Zinc-finger nucleases are site-specific endonucleases comprising two protein domains: a DNA-binding domain, comprising a plurality of individual zinc finger repeats that each recognize between 9 and 18 base pairs, and a DNA-cleavage domain that comprises a nuclease domain (typically FokI). The cleavage domain dimerizes in order to cleave DNA; therefore, a pair of ZFNs are required to target non-palindromic target polynucleotides. In certain embodiments, zinc finger nuclease and zinc finger nickase design methods which have been described (Urnov et al. (2010) *Nature Rev. Genet.*, 11:636-646; Mohanta et al. (2017) *Genes* vol. 8, 12: 399; Ramirez et al. Nucleic Acids Res. (2012); 40(12): 5560-5568; Liu et al. (2013) *Nature Communications*, 4: 2565) can be adapted for use in the methods set forth herein. The zinc finger binding domains of the zinc finger nuclease or nickase provide specificity and can be engineered to specifically recognize any desired target DNA sequence. The zinc finger DNA binding domains are derived from the DNA-binding domain of a large class of eukaryotic transcription factors called zinc finger proteins (ZFPs). The DNA-binding domain of ZFPs typically contains a tandem array of at least three zinc "fingers" each recognizing a specific triplet of DNA. A number of strategies can be used to design the binding specificity of the zinc finger binding domain. One approach, termed "modular assembly", relies on the functional autonomy of individual zinc fingers with DNA. In this approach, a given sequence is targeted by identifying zinc fingers for each component triplet in the sequence and linking them into a multifinger peptide. Several alternative strategies for designing zinc finger DNA binding domains have also been developed. These methods are designed to accommodate the ability of zinc fingers to contact neighboring fingers as well as nucleotide bases outside their target triplet. Typically, the engineered zinc finger DNA binding domain has a novel binding specificity, compared to a naturally-occurring zinc finger protein. Engineering methods include, for example, rational design and various types of selection. Rational design includes, for example, the use of databases of triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, e.g., U.S. Pat. Nos. 6,453,242 and 6,534,261, both incorporated herein by reference in their entirety. Exemplary selection methods (e.g., phage display and yeast two-hybrid systems) can be adapted for use in the methods described herein. In addition, enhancement of binding specificity for zinc finger binding domains has been described in U.S. Pat. No. 6,794,136, incorporated herein by reference in its entirety. In addition, individual zinc finger domains may be linked together using any suitable linker sequences. Examples of linker sequences are publicly known, e.g., see U.S. Pat. Nos. 6,479,626; 6,903,185; and 7,153,949, incorporated herein by reference in their entirety. The nucleic acid cleavage domain is non-specific and is typically a restriction endonuclease, such as FokI. This endonuclease must dimerize to cleave DNA. Thus, cleavage by FokI as part of a ZFN requires two adjacent and independent binding events, which must occur in both the correct orientation and with appropriate spacing to permit dimer formation. The requirement for two DNA binding events enables more specific targeting of long and potentially unique recognition sites. FokI variants with enhanced activities have been described and can be adapted for use in the methods described herein; see, e.g., Guo et al. (2010) *J. Mol. Biol.,* 400:96-107.

Transcription activator like effectors (TALEs) are proteins secreted by certain *Xanthomonas* species to modulate gene expression in host plants and to facilitate the colonization by and survival of the bacterium. TALEs act as transcription factors and modulate expression of resistance genes in the plants. Recent studies of TALEs have revealed the code linking the repetitive region of TALEs with their target DNA-binding sites. TALEs comprise a highly conserved and repetitive region consisting of tandem repeats of mostly 33 or 34 amino acid segments. The repeat monomers differ from each other mainly at amino acid positions 12 and 13. A strong correlation between unique pairs of amino acids at positions 12 and 13 and the corresponding nucleotide in the TALE-binding site has been found. The simple relationship between amino acid sequence and DNA recognition of the TALE binding domain allows for the design of DNA binding domains of any desired specificity. TALEs can be linked to a non-specific DNA cleavage domain to prepare genome editing proteins, referred to as TAL-effector nucleases or TALENs. As in the case of ZFNs, a restriction endonuclease, such as FokI, can be conveniently used. Methods for use of TALENs in plants have been described and can be adapted for use in the methods described herein, see Mahfouz et al. (2011) Proc. Natl. Acad. Sci. USA, 108:2623-2628; Mahfouz (2011) GM Crops, 2:99-103; and Mohanta et al. (2017) *Genes* vol. 8, 12: 399). TALE nickases have also been described and can be adapted for use in methods described herein (Wu et al.; Biochem Biophys Res Commun. (2014); 446(1):261-6; Luo et al; *Scientific Reports* 6, Article number: 20657 (2016)).

Embodiments of the donor DNA template molecule having a sequence that is integrated at the site of at least one double-strand break (DSB) in a genome include double-stranded DNA, a single-stranded DNA, a single-stranded DNA/RNA hybrid, and a double-stranded DNA/RNA hybrid. In embodiments, a donor DNA template molecule that is a double-stranded (e.g., a dsDNA or dsDNA/RNA hybrid) molecule is provided directly to the plant protoplast or plant cell in the form of a double-stranded DNA or a double-stranded DNA/RNA hybrid, or as two single-stranded DNA (ssDNA) molecules that are capable of hybridizing to form dsDNA, or as a single-stranded DNA molecule and a single-stranded RNA (ssRNA) molecule that are capable of hybridizing to form a double-stranded DNA/RNA hybrid; that is to say, the double-stranded polynucleotide molecule is not provided indirectly, for example, by expression in the cell of a dsDNA encoded by a plasmid or other vector. In various non-limiting embodiments of the method, the donor DNA template molecule that is integrated (or that has a sequence that is integrated) at the site of at least one double-strand break (DSB) in a genome is double-stranded and blunt-ended; in other embodiments the donor DNA template molecule is double-stranded and has an overhang or "sticky end" consisting of unpaired nucleotides (e.g., 1, 2, 3, 4, 5, or 6 unpaired nucleotides) at one terminus or both termini. In an embodiment, the DSB in the genome has no unpaired nucleotides at the cleavage site, and the donor DNA template molecule that is integrated (or that has a sequence that is integrated) at the site of the DSB is a blunt-ended double-stranded DNA or blunt-ended double-stranded DNA/RNA hybrid molecule, or alternatively is a single-stranded DNA or a single-stranded DNA/RNA hybrid molecule. In another embodiment, the DSB in the genome has one or more unpaired nucleotides at one or both sides of the cleavage site, and the donor DNA template molecule that is integrated (or that has a sequence that is integrated) at the site of the DSB is a double-stranded DNA or double-stranded DNA/RNA hybrid molecule with an overhang or "sticky end" consisting of unpaired nucleotides at one or both termini, or alternatively is a single-stranded DNA or a single-stranded DNA/RNA hybrid molecule; in embodiments, the donor DNA template molecule DSB is a double-stranded DNA or double-stranded DNA/RNA hybrid molecule that includes an overhang at one or at both termini, wherein the overhang consists of the same number of unpaired nucleotides as the number of unpaired nucleotides created at the site of a DSB by a nuclease that cuts in an off-set fashion (e.g., where a Cas12 nuclease effects an off-set DSB with 5-nucleotide overhangs in the genomic sequence, the donor DNA template molecule that is to be integrated (or that has a sequence that is to be integrated) at the site of the DSB is double-stranded and has 5 unpaired nucleotides at one or both termini). In certain embodiments, one or both termini of the donor DNA template molecule contain no regions of sequence homology (identity or complementarity) to genomic regions flanking the DSB; that is to say, one or both termini of the donor DNA template molecule contain no regions of sequence that is sufficiently complementary to permit hybridization to genomic regions immediately adjacent to the location of the DSB. In embodiments, the donor DNA template molecule contains no homology to the locus of the DSB, that is to say, the donor DNA template molecule contains no nucleotide sequence that is sufficiently complementary to permit hybridization to genomic regions immediately adjacent to the location of the DSB. In embodiments, the donor DNA template molecule is at least partially double-stranded and includes 2-20 base-pairs, e. g., 2, 3, 4, 5, 6, 7, 8, 9, 10, 11, 12, 13, 14, 15, 16, 17, 18, 19, or 20 base-pairs; in embodiments, the donor DNA template molecule is double-stranded and blunt-ended and consists of 2-20 base-pairs, e.g., 2, 3, 4, 5, 6, 7, 8, 9, 10, 11, 12, 13, 14, 15, 16, 17, 18, 19, or 20 base-pairs; in other embodiments, the donor DNA template molecule is double-stranded and includes 2-20 base-pairs, e.g., 2, 3, 4, 5, 6, 7, 8, 9, 10, 11, 12, 13, 14, 15, 16, 17, 18, 19, or 20 base-pairs and in addition has at least one overhang or "sticky end" consisting of at least one additional, unpaired nucleotide at one or at both termini. In an embodiment, the donor DNA template molecule that is integrated (or that has a sequence that is integrated) at the site of at least one double-strand break (DSB) in a genome is a blunt-ended double-stranded DNA or a blunt-ended double-stranded DNA/RNA hybrid molecule of about 18 to about 300 base-pairs, or about 20 to about 200 base-pairs, or about 30 to about 100 base-pairs, and having at least one phosphorothioate bond between adjacent nucleotides at a 5' end, 3' end, or both 5' and 3' ends. In embodiments, the donor DNA template molecule includes single strands of at least 11, at least 18, at least 20, at least 30, at least 40, at least 60, at least 80, at least 100, at least 120, at least 140, at least 160, at least 180, at least 200, at least 240, at about 280, or at least 320 nucleotides. In embodiments, the donor DNA template molecule has a length of at least 2, at least 3, at least 4, at least 5, at least 6, at least 7, at least 8, at least 9, at least 10, or at least 11 base-pairs if double-stranded (or nucleotides if single-stranded), or between about 2 to about 320 base-pairs if double-stranded (or nucleotides if single-stranded), or between about 2 to about 500 base-pairs if double-stranded (or nucleotides if single-stranded), or between about 5 to about 500 base-pairs if double-stranded (or nucleotides if single-stranded), or between about 5 to about 300 base-pairs if double-stranded (or nucleotides if single-stranded), or between about 11 to about 300 base-pairs if double-stranded (or nucleotides if single-stranded), or about 18 to about 300 base-pairs if double-stranded (or nucleotides if single-stranded), or between about 30 to about 100 base-pairs if double-stranded (or nucleotides if single-stranded). In embodiments, the donor DNA template molecule includes chemically modified nucleotides (see, e.g., the various modifications of internucleotide linkages, bases, and sugars described in Verma and Eckstein (1998) Annu. Rev. Biochem., 67:99-134); in embodiments, the naturally occurring phosphodiester backbone of the donor DNA template molecule is partially or completely modified with phosphorothioate, phosphorodithioate, or methylphosphonate internucleotide linkage modifications, or the donor DNA template molecule includes modified nucleoside bases or modified sugars, or the donor DNA template molecule is labelled with a fluorescent moiety (e.g., fluorescein or rhodamine or a fluorescent nucleoside analogue) or other detectable label (e.g., biotin or an isotope). In another embodiment, the donor DNA template molecule contains secondary structure that provides stability or acts as an aptamer. Other related embodiments include double-stranded DNA/RNA hybrid molecules, single-stranded DNA/RNA hybrid donor molecules, and single-stranded donor DNA template molecules (including single-stranded, chemically modified donor DNA template molecules), which in analogous procedures are integrated (or have a sequence that is integrated) at the site of a double-strand break. Donor DNA templates provided herein include those comprising CgRRS sequences flanked by DNA with homology to a donor polynucleotide and include the donor DNA template set forth in SEQ ID NO: 9, 21, and equivalents thereof with longer or shorter homology arms. In certain embodiments, a donor DNA template can comprise an adapter molecule (e.g., a donor DNA template formed by annealing single stranded DNAs which do not overlap at their 5' and 3' terminal ends) with cohesive ends which can anneal to an overhanging cleavage site (e.g., introduced by a Cas12a nuclease and suitable gRNAs). In certain embodiments, integration of the donor DNA templates can be facilitated by use of a bacteriophage lambda exonuclease, a bacteriophage lambda beta SSAP protein, and an *E. coli* SSB essentially as set forth in US Patent Application Publication 20200407754, which is incorporated herein by reference in its entirety.

Donor DNA template molecules used in the methods provided herein include DNA molecules comprising, from 5' to 3', a first homology arm, a replacement DNA, and a second homology arm, wherein the homology arms containing sequences that are partially or completely homologous to genomic DNA (gDNA) sequences flanking a target site-specific endonuclease cleavage site in the gDNA. In certain embodiments, the replacement DNA can comprise an insertion, deletion, or substitution of 1 or more DNA base pairs relative to the target gDNA. In an embodiment, the donor DNA template molecule is double-stranded and perfectly base-paired through all or most of its length, with the possible exception of any unpaired nucleotides at either terminus or both termini. In another embodiment, the donor DNA template molecule is double-stranded and includes one or more non-terminal mismatches or non-terminal unpaired nucleotides within the otherwise double-stranded duplex. In an embodiment, the donor DNA template molecule that is integrated at the site of at least one double-strand break (DSB) includes between 2-20 nucleotides in one (if single-stranded) or in both strands (if double-stranded), e. g., 2, 3, 4, 5, 6, 7, 8, 9, 10, 11, 12, 13, 14, 15, 16, 17, 18, 19, or 20 nucleotides on one or on both strands, each of which can be base-paired to a nucleotide on the opposite strand (in the case of a perfectly base-paired double-stranded polynucleotide molecule). Such donor DNA templates can be integrated in genomic DNA containing blunt and/or staggered double stranded DNA breaks by homology-directed repair (HDR). In certain embodiments, a donor DNA template homology arm can be about 20, 50, 100, 200, 400, or 600 to about 800, or 1000 base pairs in length. In certain embodiments, a donor DNA template molecule can be delivered to a plant cell) in a circular (e.g., a plasmid or a viral vector including a geminivirus vector) or a linear DNA molecule. In certain embodiments, a circular or linear DNA molecule that is used can comprise a modified donor DNA template molecule comprising, from 5' to 3', a first copy of the target sequence-specific endonuclease cleavage site sequence, the first homology arm, the replacement DNA, the second homology arm, and a second copy of the target sequence-specific endonuclease cleavage site sequence. Without seeking to be limited by theory, such modified donor DNA template molecules can be cleaved by the same sequence-specific endonuclease that is used to cleave the target site gDNA of the eukaryotic cell to release a donor DNA template molecule that can participate in HDR-mediated genome modification of the target editing site in the plant cell genome. In certain embodiments, the donor DNA template can comprise a linear DNA molecule comprising, from 5' to 3', a cleaved target sequence-specific endonuclease cleavage site sequence, the first homology arm, the replacement DNA, the second homology arm, and a cleaved target sequence-specific endonuclease cleavage site sequence. In certain embodiments, the cleaved target sequence-specific endonuclease sequence can comprise a blunt DNA end or a blunt DNA end that can optionally comprise a 5' phosphate group. In certain embodiments, the cleaved target sequence-specific endonuclease sequence comprises a DNA end having a single-stranded 5' or 3' DNA overhang. Such cleaved target sequence-specific endonuclease cleavage site sequences can be produced by either cleaving an intact target sequence-specific endonuclease cleavage site sequence or by synthesizing a copy of the cleaved target sequence-specific endonuclease cleavage site sequence. Donor DNA templates can be synthesized either chemically or enzymatically (e.g., in a polymerase chain reaction (PCR)). Donor DNA templates provided herein include those comprising CgRRS sequences flanked by DNA with homology to a donor polynucleotide. An example of a useful DNA donor template provided herein is a DNA molecule comprising SEQ ID NO: 9 or 21.

Various treatments are useful in delivery of gene editing molecules and/or other molecules to a MON87701 or INIR20 plant cell. In certain embodiments, one or more treatments is employed to deliver the gene editing or other molecules (e.g., comprising a polynucleotide, polypeptide or combination thereof) into a eukaryotic or plant cell, e.g., through barriers such as a cell wall, a plasma membrane, a nuclear envelope, and/or other lipid bilayer. In certain embodiments, a polynucleotide-, polypeptide-, or RNP-containing composition comprising the molecules are delivered directly, for example by direct contact of the composition with a plant cell. Aforementioned compositions can be provided in the form of a liquid, a solution, a suspension, an emulsion, a reverse emulsion, a colloid, a dispersion, a gel, liposomes, micelles, an injectable material, an aerosol, a solid, a powder, a particulate, a nanoparticle, or a combination thereof can be applied directly to a plant, plant part, plant cell, or plant explant (e.g., through abrasion or puncture or otherwise disruption of the cell wall or cell membrane, by spraying or dipping or soaking or otherwise directly contacting, by microinjection). For example, a plant cell or plant protoplast is soaked in a liquid genome editing molecule-containing composition, whereby the agent is delivered to the plant cell. In certain embodiments, the agent-containing composition is delivered using negative or positive pressure, for example, using vacuum infiltration or application of hydrodynamic or fluid pressure. In certain embodiments, the agent-containing composition is introduced into a plant cell or plant protoplast, e.g., by microinjection or by disruption or deformation of the cell wall or cell membrane, for example by physical treatments such as by application of negative or positive pressure, shear forces, or treatment with a chemical or physical delivery agent such as surfactants, liposomes, or nanoparticles; see, e.g., delivery of materials to cells employing microfluidic flow through a cell-deforming constriction as described in US Published Patent Application 2014/0287509, incorporated by reference in its entirety herein. Other techniques useful for delivering the agent-containing composition to a eukaryotic cell, plant cell or plant protoplast include: ultrasound or sonication; vibration, friction, shear stress, vortexing, cavitation; centrifugation or application of mechanical force; mechanical cell wall or cell membrane deformation or breakage; enzymatic cell wall or cell membrane breakage or permeabilization; abrasion or mechanical scarification (e.g., abrasion with carborundum or other particulate abrasive or scarification with a file or sandpaper) or chemical scarification (e.g., treatment with an acid or caustic agent); and electroporation. In certain embodiments, the agent-containing composition is provided by bacterially mediated (e.g., *Agrobacterium* sp., *Rhizobium* sp., *Sinorhizobium* sp., *Mesorhizobium* sp., *Bradyrhizobium* sp., Azobacter sp., Phyllobacterium sp.) transfection of the plant cell or plant protoplast with a polynucleotide encoding the genome editing molecules (e.g., RNA dependent DNA endonuclease, RNA dependent DNA binding protein, RNA dependent nickase, ABE, or CBE, and/or guide RNA); see, e.g., Broothaerts et al. (2005) Nature, 433:629-633). Any of these techniques or a combination thereof are alternatively employed on the plant explant, plant part or tissue or intact plant (or seed) from which a plant cell is optionally subsequently obtained or isolated; in certain embodiments, the agent-containing composition is delivered in a separate step after the plant cell has been isolated.

In some embodiments, one or more polynucleotides or vectors driving expression of one or more genome editing molecules or trait-conferring genes (e.g., herbicide tolerance, insect resistance, and/or male sterility) are introduced into a MON87701 or INIR20 plant cell. In certain embodiments, a polynucleotide vector comprises a regulatory element such as a promoter operably linked to one or more polynucleotides encoding genome editing molecules and/or trait-conferring genes. In such embodiments, expression of these polynucleotides can be controlled by selection of the appropriate promoter, particularly promoters functional in a eukaryotic cell (e.g., plant cell); useful promoters include constitutive, conditional, inducible, and temporally or spatially specific promoters (e.g., a tissue specific promoter, a developmentally regulated promoter, or a cell cycle regulated promoter). Developmentally regulated promoters that can be used in plant cells include Phospholipid Transfer Protein (PLTP), fructose-1,6-bisphosphatase protein, NAD (P)-binding Rossmann-Fold protein, adipocyte plasma membrane-associated protein-like protein, Rieske [2Fe-2S] iron-sulfur domain protein, chlororespiratory reduction 6 protein, D-glycerate 3-kinase, chloroplastic-like protein, chlorophyll a-b binding protein 7, chloroplastic-like protein, ultraviolet-B-repressible protein, Soul heme-binding family protein, Photosystem I reaction center subunit psi-N protein, and short-chain dehydrogenase/reductase protein that are disclosed in US Patent Application Publication No. 20170121722, which is incorporated herein by reference in its entirety and specifically with respect to such disclosure. In certain embodiments, the promoter is operably linked to nucleotide sequences encoding multiple guide RNAs, wherein the sequences encoding guide RNAs are separated by a cleavage site such as a nucleotide sequence encoding a microRNA recognition/cleavage site or a self-cleaving ribozyme (see, e.g., Ferré-D'Amaré and Scott (2014) Cold Spring Harbor Perspectives Biol., 2:a003574). In certain embodiments, the promoter is an RNA polymerase III promoter operably linked to a nucleotide sequence encoding one or more guide RNAs. In certain embodiments, the RNA polymerase III promoter is a plant U6 spliceosomal RNA promoter, which can be native to the genome of the plant cell or from a different species, e.g., a U6 promoter from soybean, tomato, or soybean such as those disclosed U.S. Patent Application Publication 2017/0166912, or a homologue thereof; in an example, such a promoter is operably linked to DNA sequence encoding a first RNA molecule including a Cas12a gRNA followed by an operably linked and suitable 3' element such as a U6 poly-T terminator. In another embodiment, the RNA polymerase III promoter is a plant U3, 7SL (signal recognition particle RNA), U2, or U5 promoter, or chimerics thereof, e.g., as described in U.S. Patent Application Publication 20170166912. In certain embodiments, the promoter operably linked to one or more polynucleotides is a constitutive promoter that drives gene expression in eukaryotic cells (e.g., plant cells). In certain embodiments, the promoter drives gene expression in the nucleus or in an organelle such as a chloroplast or mitochondrion. Examples of constitutive promoters for use in plants include a CaMV 35S promoter as disclosed in U.S. Pat. Nos. 5,858,742 and 5,322,938, a rice actin promoter as disclosed in U.S. Pat. No. 5,641,876, a soybean chloroplast aldolase promoter as disclosed in U.S. Pat. No. 7,151,204, and the nopaline synthase (NOS) and octopine synthase (OCS) promoters from *Agrobacterium tumefaciens*. In certain embodiments, the promoter operably linked to one or more polynucleotides encoding elements of a genome-editing system is a promoter from figwort mosaic virus (FMV), a RUBISCO promoter, or a pyruvate phosphate dikinase (PPDK) promoter, which is active in photosynthetic tissues. Other contemplated promoters include cell-specific or tissue-specific or developmentally regulated promoters, for example, a promoter that limits the expression of the nucleic acid targeting system to germline or reproductive cells (e.g., promoters of genes encoding DNA ligases, recombinases, replicases, or other genes specifically expressed in germline or reproductive cells). In certain embodiments, the genome alteration is limited only to those cells from which DNA is inherited in subsequent generations, which is advantageous where it is desirable that expression of the genome-editing system be limited in order to avoid genotoxicity or other unwanted effects. All of the patent publications referenced in this paragraph are incorporated herein by reference in their entirety.

Expression vectors or polynucleotides provided herein may contain a DNA segment near the 3' end of an expression cassette that acts as a signal to terminate transcription and directs polyadenylation of the resultant mRNA and may also support promoter activity. Such a 3' element is commonly referred to as a "3'-untranslated region" or "3'-UTR" or a "polyadenylation signal." In some cases, plant gene-based 3' elements (or terminators) consist of both the 3'-UTR and downstream non-transcribed sequence (Nuccio et al., 2015). Useful 3' elements include: *Agrobacterium tumefaciens* nos 3', tml 3', tmr 3', tms 3', ocs 3', and tr7 3' elements disclosed in U.S. Pat. No. 6,090,627, incorporated herein by reference, and 3' elements from plant genes such as the heat shock protein 17, ubiquitin, and fructose-1,6-biphosphatase genes from wheat (*Triticum aestivum*), and the glutelin, lactate dehydrogenase, and beta-tubulin genes from rice (*Oryza sativa*), disclosed in US Patent Application Publication 2002/0192813 A1. All of the patent publications referenced in this paragraph are incorporated herein by reference in their entireties.

In certain embodiments, the MON87701 or INIR20 plant cells used herein can comprise haploid, diploid, or polyploid plant cells or plant protoplasts, for example, those obtained from a haploid, diploid, or polyploid plant, plant part or tissue, or callus. In certain embodiments, plant cells in culture (or the regenerated plant, progeny seed, and progeny plant) are haploid or can be induced to become haploid; techniques for making and using haploid plants and plant cells are known in the art, see, e.g., methods for generating haploids in *Arabidopsis thaliana* by crossing of a wild-type strain to a haploid-inducing strain that expresses altered forms of the centromere-specific histone CENH3, as described by Maruthachalam and Chan in "How to make haploid *Arabidopsis thaliana*", protocol available at www [dot]openwetware[dot]org/images/d/d3/Haploid_Arabidopsis_protocol[dot] pdf; (Ravi et al. (2014) *Nature Communications*, 5:5334, doi: 10.1038/ncomms6334). Haploids can also be obtained in a wide variety of monocot plants (e.g., soybean, wheat, rice, sorghum, barley) by crossing a plant comprising a mutated CENH3 gene with a wildtype diploid plant to generate haploid progeny as disclosed in U.S. Pat. No. 9,215,849, which is incorporated herein by reference in its entirety. Haploid-inducing soybean lines that can be used to obtain haploid soybean plants and/or cells include Stock 6, MHI (Moldovian Haploid Inducer), indeterminate gametophyte (ig) mutation, KEMS, RWK, ZEM, ZMS, KMS, and well as transgenic haploid inducer lines disclosed in U.S. Pat. No. 9,677,082, which is incorporated herein by reference in its entirety. Examples of haploid cells include but are not limited to plant cells obtained from haploid plants and plant cells obtained from reproductive tissues, e.g., from flowers, developing flowers or flower buds, ovaries, ovules, megaspores, anthers, pollen, megagametophyte, and microspores. In certain embodiments where the plant cell or plant protoplast is haploid, the genetic complement can be doubled by chromosome doubling (e.g., by spontaneous chromosomal doubling by meiotic non-reduction, or by using a chromosome doubling agent such as colchicine, oryzalin, trifluralin, pronamide, nitrous oxide gas, anti-microtubule herbicides, anti-microtubule agents, and mitotic inhibitors) in the plant cell or plant protoplast to produce a doubled haploid plant cell or plant protoplast wherein the complement of genes or alleles is homozygous; yet other embodiments include regeneration of a doubled haploid plant from the doubled haploid plant cell or plant protoplast. Another embodiment is related to a hybrid plant having at least one parent plant that is a doubled haploid plant provided by this approach. Production of doubled haploid plants provides homozygosity in one generation, instead of requiring several generations of self-crossing to obtain homozygous plants. The use of doubled haploids is advantageous in any situation where there is a desire to establish genetic purity (i.e., homozygosity) in the least possible time. Doubled haploid production can be particularly advantageous in slow-growing plants or for producing hybrid plants that are offspring of at least one doubled-haploid plant.

In certain embodiments, the MON87701 or INIR20 plant cells used in the methods provided herein can include non-dividing cells. Such non-dividing cells can include plant cell protoplasts, plant cells subjected to one or more of a genetic and/or pharmaceutically-induced cell-cycle blockage, and the like.

In certain embodiments, the MON87701 or INIR20 plant cells in used in the methods provided herein can include dividing cells. Dividing cells can include those cells found in various plant tissues including leaves, meristems, and embryos. These tissues include dividing cells from young soybean leaf, meristems and scutellar tissue from about 8 or 10 to about 12 or 14 days after pollination (DAP) embryos. The isolation of soybean embryos has been described in several publications (Brettschneider, Becker, and Lörz 1997; Leduc et al. 1996; Frame et al. 2011; K. Wang and Frame 2009). In certain embodiments, basal leaf tissues (e.g., leaf tissues located about 0 to 3 cm from the ligule of a soybean plant; Kirienko, Luo, and Sylvester 2012) are targeted for HDR-mediated gene editing. Methods for obtaining regenerable plant structures and regenerating plants from the NHEJ-, MMEJ-, or HDR-mediated gene editing of plant cells provided herein can be adapted from methods disclosed in US Patent Application Publication No. 20170121722, which is incorporated herein by reference in its entirety and specifically with respect to such disclosure. In certain embodiments, single plant cells subjected to the HDR-mediated gene editing will give rise to single regenerable plant structures. In certain embodiments, the single regenerable plant cell structure can form from a single cell on, or within, an explant that has been subjected to the NHEJ-, MMEJ-, or HDR-mediated gene editing.

In some embodiments, methods provided herein can include the additional step of growing or regenerating an INIR20 plant from a INIR20 plant cell that had been subjected to the gene editing or from a regenerable plant structure obtained from that INIR20 plant cell. In certain embodiments, the plant can further comprise an inserted transgene, a target gene edit, or genome edit as provided by the methods and compositions disclosed herein. In certain embodiments, callus is produced from the plant cell, and plantlets and plants produced from such callus. In other embodiments, whole seedlings or plants are grown directly from the plant cell without a callus stage. Thus, additional related aspects are directed to whole seedlings and plants grown or regenerated from the plant cell or plant protoplast having a target gene edit or genome edit, as well as the seeds of such plants. In certain embodiments wherein the plant cell or plant protoplast is subjected to genetic modification (for example, genome editing by means of, e.g., an RdDe), the grown or regenerated plant exhibits a phenotype associated with the genetic modification. In certain embodiments, the grown or regenerated plant includes in its genome two or more genetic or epigenetic modifications that in combination provide at least one phenotype of interest. In certain embodiments, a heterogeneous population of plant cells having a target gene edit or genome edit, at least some of which include at least one genetic or epigenetic modification, is provided by the method; related aspects include a plant having a phenotype of interest associated with the genetic or epigenetic modification, provided by either regeneration of a plant having the phenotype of interest from a plant cell or plant protoplast selected from the heterogeneous population of plant cells having a target gene or genome edit, or by selection of a plant having the phenotype of interest from a heterogeneous population of plants grown or regenerated from the population of plant cells having a targeted genetic edit or genome edit. Examples of phenotypes of interest include herbicide resistance, improved tolerance of abiotic stress (e.g., tolerance of temperature extremes, drought, or salt) or biotic stress (e.g., resistance to nematode, bacterial, or fungal pathogens), improved utilization of nutrients or water, modified lipid, carbohydrate, or protein composition, improved flavor or appearance, improved storage characteristics (e.g., resistance to bruising, browning, or softening), increased yield, altered morphology (e.g., floral architecture or color, plant height, branching, root structure). In an embodiment, a heterogeneous population of plant cells having a target gene edit or genome edit (or seedlings or plants grown or regenerated therefrom) is exposed to conditions permitting expression of the phenotype of interest; e.g., selection for herbicide resistance can include exposing the population of plant cells having a target gene edit or genome edit (or seedlings or plants grown or regenerated therefrom) to an amount of herbicide or other substance that inhibits growth or is toxic, allowing identification and selection of those resistant plant cells (or seedlings or plants) that survive treatment. Methods for obtaining regenerable plant structures and regenerating plants from plant cells or regenerable plant structures can be adapted from published procedures (Roest and Gilissen, Acta Bot. Neerl., 1989, 38(1), 1-23; Bhaskaran and Smith, Crop Sci. 30(6):1328-1337; Ikeuchi et al., Development, 2016, 143: 1442-1451). Methods for obtaining regenerable plant structures and regenerating plants from plant cells or regenerable plant structures can also be adapted from US Patent Application Publication No. 20170121722, which is incorporated herein by reference in its entirety and specifically with respect to such disclosure. Also provided are heterogeneous or homogeneous populations of such plants or parts thereof (e.g., seeds), succeeding generations or seeds of such plants grown or regenerated from the plant cells or plant protoplasts, having a target gene edit or genome edit. Additional related aspects include a hybrid plant provided by crossing a first plant grown or regenerated from a plant cell or plant protoplast having a target gene edit or genome edit and having at least one genetic or epigenetic modification, with a second plant, wherein the hybrid plant contains the genetic or epigenetic modification; also contemplated is seed produced by the hybrid plant. Also envisioned as related aspects are progeny seed and progeny plants, including hybrid seed and hybrid plants, having the regenerated plant as a parent or ancestor. The plant cells and derivative plants and seeds disclosed herein can be used for various purposes useful to the consumer or grower. In other embodiments, processed products are made from the INIR20 plant or its seeds, including: (a) soybean seed meal (defatted or non-defatted); (b) extracted proteins, oils, sugars, and starches; (c) fermentation products; (d) animal feed or human food products (e.g., feed and food comprising soybean seed meal (defatted or non-defatted) and other ingredients (e.g., other cereal grains, other seed meal, other protein meal, other oil, other starch, other sugar, a binder, a preservative, a humectant, a vitamin, and/or mineral; (e) a pharmaceutical; (f) raw or processed biomass (e.g., cellulosic and/or lignocellulosic material); and (g) various industrial products.

Embodiments

Various embodiments of the plants, genomes, methods, biological samples, and other compositions described herein are set forth in the following sets of numbered embodiments.

1a. A transgenic soybean plant cell comprising an INIR20 transgenic locus comprising an originator guide RNA recognition site (OgRRS) in a first DNA junction polynucleotide of a MON87701 transgenic locus and a cognate guide RNA recognition site (CgRRS) in a second DNA junction polynucleotide of the MON87701 transgenic locus.

1b. A transgenic soybean plant cell comprising an INIR20 transgenic locus comprising an insertion and/or substitution of DNA in a DNA junction polynucleotide of a MON87701 transgenic locus with DNA comprising a cognate guide RNA recognition site (CgRRS) or comprising a deletion in a 5' or 3' junction polynucleotide of a MON87701 transgenic locus.

2. The transgenic soybean plant cell of embodiment 1a or 1b, wherein said CgRRS comprises the DNA molecule set forth in SEQ ID NO: 8 or 7; and/or wherein said MON87701 transgenic locus is set forth in SEQ ID NO:1, is present in seed deposited at the ATCC under accession No. PTA-8194, is present in progeny thereof, is present in allelic variants thereof, or is present in other variants thereof.

3. The transgenic soybean plant cell of embodiments 1a, 1b, or 2, wherein said INIR20 transgenic locus comprises the DNA molecule set forth in SEQ ID NO: 2, 3, 15, or an allelic variant thereof.

4. A transgenic soybean plant part comprising the soybean plant cell of any one of embodiments 1a, 1b, 2, or 3, wherein said soybean plant part is optionally a seed.

5. A transgenic soybean plant comprising the soybean plant cell of any one of embodiments 1a, 1b, 2, or 3.

6. A method for obtaining a bulked population of inbred seed comprising selfing the transgenic soybean plant of embodiment 5 and harvesting seed comprising the INIR20 transgenic locus from the selfed soybean plant.

7. A method of obtaining hybrid soybean seed comprising crossing the transgenic soybean plant of embodiment 5 to a second soybean plant which is genetically distinct from the first soybean plant and harvesting seed comprising the INIR20 transgenic locus from the cross.

8. A DNA molecule comprising SEQ ID NO: 2, 3, 7, 8, 9, 14, 15, or 21.

9. A processed transgenic soybean plant product comprising the DNA molecule of embodiment 8.

10. A biological sample containing the DNA molecule of embodiment 8.

11. A nucleic acid molecule adapted for detection of genomic DNA comprising the DNA molecule of embodiment 8, wherein said nucleic acid molecule optionally comprises a detectable label.

12. A method of detecting a soybean plant cell comprising the INIR20 transgenic locus of any one of embodiments 1a, 1b, 2, or 3, comprising the step of detecting DNA molecule comprising SEQ ID NO: 2, 3, 7, 8, 9, 14, 15, or 21.

13. A method of excising the INIR20 transgenic locus from the genome of the soybean plant cell of any one of embodiments 1a, 1b, 2, or 3, comprising the steps of:
(a) contacting the plant cell or genome thereof with: (i) an RNA dependent DNA endonuclease (RdDe); and (ii) a guide RNA (gRNA) capable of hybridizing to the guide RNA hybridization site of the OgRRS and the CgRRS; wherein the RdDe recognizes a OgRRS/gRNA and a CgRRS/gRNA hybridization complex; and,
(b) selecting a transgenic plant cell, transgenic plant part, or transgenic plant wherein the INIR20 transgenic locus flanked by the OgRRS and the CgRRS has been excised.

14. The method of embodiment 13, wherein said INIR20 transgenic locus comprises the CgRRS in SEQ ID NO: 8 or 7 and the guide RNA comprises an RNA sequence encoded by SEQ ID NO: 11.

15. The method of embodiment 14, wherein said INIR20 transgenic locus comprises the DNA molecule set forth in SEQ ID NO: 3, 15, or an allelic variant thereof.

Examples

Figure 4:
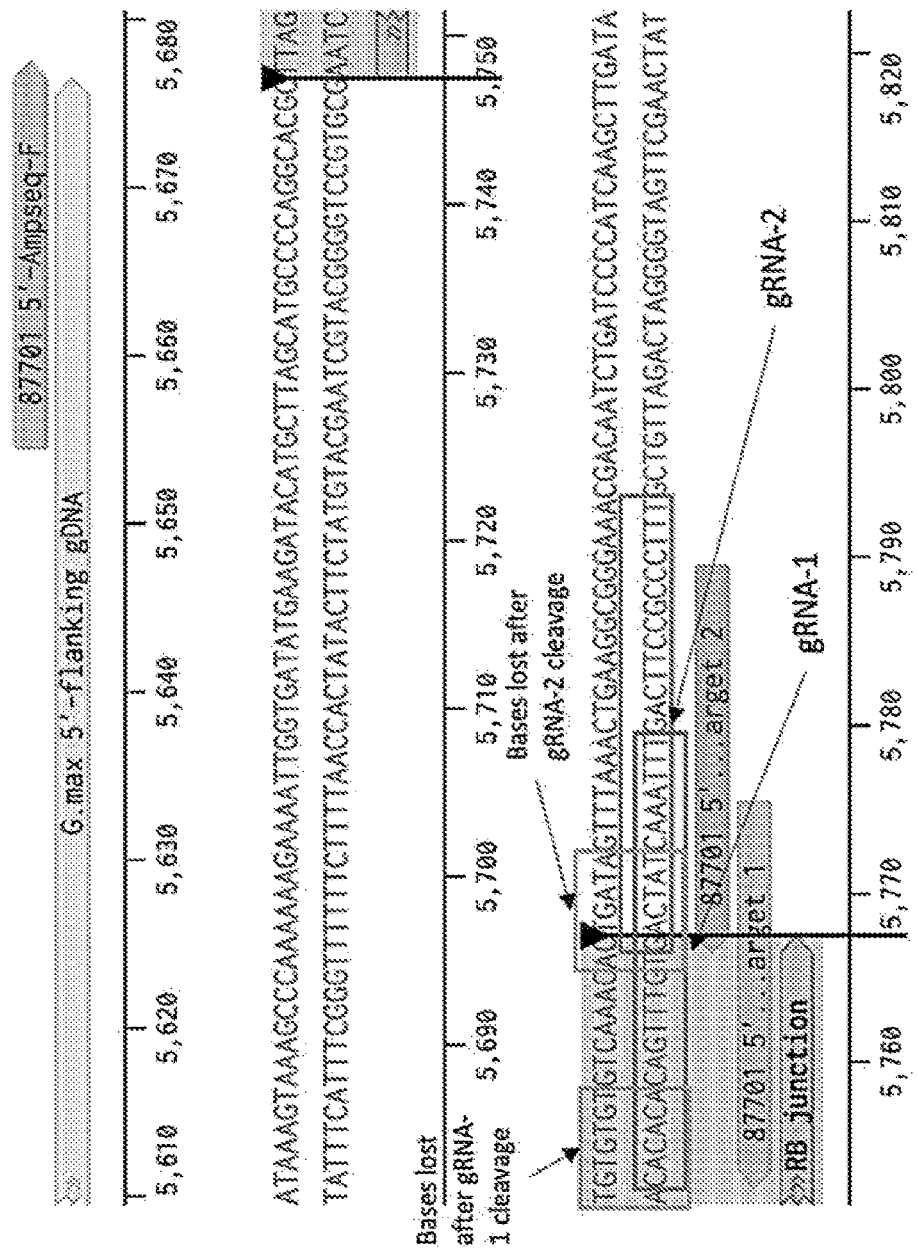
FIG. 4 illustrates the locations of gRNA-1 (SEQ ID NO: 4) and gRNA-2 (SEQ ID NO: 5) recognition sites in the 5' junction polynucleotide of SEQ ID NO: 1. Sequences in the figure are the corresponding sequences of SEQ ID NO: 1 and their reverse complement.

Example 1. Application of a Cas12a RNA Guided Endonuclease and Guide RNAs to Change or Excise the 5'-T-DNA Junction Sequence in the MON87701 Event The MON87701 5' junction polynucleotide sequence set forth in SEQ ID NO: 17 contains at least two Cas12a recognition sequences. The Guide-1 (gRNA-1) and Guide-2 (gRNA-2) sequence locations in the 5' junction polynucleotide are shown in FIG. 4. These guide RNAs can be used to modify some of the 5' junction polynucleotide sequence. In one embodiment, Guide-tor Guide-2 are used alone to disrupt the MON87701 5'-junction sequence (e.g., by using a Cas12a endonuclease and 1 of Guide-1 or Guide-2 to cleave the 5' junction polynucleotide sequence and recovering genomic edits where the 5' DNA junction polynucleotide sequence of MON87701 is disrupted.

The Cas12a nuclease and the guide RNA is introduced into soybean plant cells containing the MON87701 event. In certain embodiments, the Cas12a nuclease and gRNA(s) are encoded and expressed from a T-DNA transformed into the MON87701 event via Agrobacterium-mediated transformation. Alternatively, the T-DNA can be transformed into any convenient soy line, and then crossed with the MON87701 event to combine the Cas12a ribonucleoprotein expressing T-DNA with the MON87701 event. The Cas12a nuclease and gRNAs can also be assembled in vitro then delivered to MON87701 explants as ribonucleoprotein complexes using a biolistic approach (Svitashev et al., Nat Commun. 2016; 7:13274; Zhang et al., 2021, Plant Commun. 2(2):100168). Also, a plasmid encoding a Cas12a nuclease, and the gRNA(s) can be delivered to MON87701 explants using a biolistic approach. This will produce plant cells that have a high likelihood of incurring mutations that disrupt the MON87701 5' junction polynucleotide sequence.

In the Agrobacterium approach, a binary vector that contains a strong constitutive expression cassette like the AtUbi10 promoter::AtUbi10 terminator driving Cas12a, a PolII or PolII gene cassette driving the Cas12a gRNA(s) and a CaMV 35S:NPTII:NOS (e.g., for G418 or neomycin selection) or other suitable plant selectable marker (e.g., a phosphomannose isomerase (Reed et al. 2001, *In Vitro Cellular & Developmental Biology-Plant* 37: 127-132) or hygromycin phosphotransferase (Itaya, et al. 2018, *In Vitro Cellular & Developmental Biology-Plant* 54: 184-194)) is constructed and cells comprising the integrated T-DNA(s) are selected using an appropriate selection agent. An expression cassette driving a fluorescent protein like mScarlet may also be useful to monitor the plant transformation process.

The T-DNA-based expression cassettes are delivered from superbinary vectors in Agrobacterium strain LBA4404. Soy transformations are performed based on published methods (Zhang et al., 1999, Plant Cell, Tissue and Organ Culture 56(1), 37-46). Briefly, cotyledonary explants are prepared from the 5-day-old soybean seedlings by making a horizontal slice through the hypocotyl region, approximately 3-5 mm below the cotyledon. A subsequent vertical slice is made between the cotyledons, and the embryonic axis is removed. This generates 2 cotyledonary node explants. Approximately 7-12 vertical slices are made on the adaxial surface of the explant about the area encompassing 3 mm above the cotyledon/hypocotyl junction and 1 mm below the cotyledon/hypocotyl junction. Explant manipulations are done with a No. 15 scalpel blade.

Explants are immersed in the Agrobacterium inoculum for 30 min and then co-cultured on 100×15 mm Petri plates containing the Agrobacterium resuspension medium solidified with 0.5% purified agar (BBL Cat #11853). The co-cultivation plates are overlaid with a piece of Whatman #1 filter paper (Mullins et al., 1990; Janssen and Gardner, 1993; Zhang et al., 1997). The explants (5 per plate) are cultured adaxial side down on the co-cultivation plates, that are overlaid with filter paper, for 3 days at 24° C., under an 18/6 hour light regime with an approximate light intensity of 80 $\mu$mol s$^{-1}$ m$^{-2}$ (F17T8/750 cool white bulbs, Litetronics®). The co-cultivation plates are wrapped with Parafilm®.

Following the co-cultivation period explants are briefly washed in B5 medium supplemented with 1.67 mg l$^{-1}$ BAP, 3% sucrose, 500 mg l$^{-1}$ ticarcillin and 100 mg l$^{-1}$ cefotaxime. The medium is buffered with 3 mM MES, pH 5.6. Growth regulator, vitamins and antibiotics are filter sterilized post autoclaving. Following the washing step, explants are cultured (5 per plate) in 100×20 mm Petri plates, adaxial side up with the hypocotyl imbedded in the medium, containing the washing medium solidified with 0.8% purified agar (BBL Cat #11853) amended with either G418, neomycin, or kanamycin at concentrations permitting selection of transformants. This medium is referred to as shoot initiation medium (SI). Plates are wrapped with 3M pressure sensitive tape (Scotch™, 3M, USA) and cultured under the environmental conditions used during the seed germination step (at 24° C., 18/6 light regime, under a light intensity of approximately 150 μmol s$^{-1}$ m$^{-2}$.

After 2 weeks of culture, the hypocotyl region is excised from each of the explants, and the remaining explant, cotyledon with differentiating node, is subsequently subcultured onto fresh SI medium. Following an additional 2 weeks of culture on SI medium, the cotyledons are removed from the differentiating node. The differentiating node is subcultured to shoot elongation medium (SE) composed of Murashige and Skoog (MS) (1962) basal salts, B5 vitamins, 1 mg l$^{-1}$ zeatin-riboside, 0.5 mg l$^{-1}$ GA3 and 0.1 mg l$^{-1}$ IAA, 50 mg l$^{-1}$ glutamine, 50 mg l$^{-1}$ asparagine, 3% sucrose and 3 mM MES, pH 5.6. The SE medium is amended with G418, neomycin, or kanamycin at concentrations permitting selection of transformants. The explants are subcultured biweekly to fresh SI medium until shoots reach a length greater than 3 cm. The elongated shoots are rooted on Murashige and Skoog salts with B5 vitamins, 1% sucrose, 0.5 mg l$^{-1}$ NAA without further selection in Magenta Boxes®.

When a sufficient amount of viable tissue is obtained, it can be screened for mutations at the MON87701 junction sequence, using a PCR-based approach. One way to screen is to design DNA oligonucleotide primers that flank and amplify the MON87701 junction plus surrounding sequence. For example, the primers of SEQ ID NO: 12 and SEQ ID NO: 13 will produce a product in a PCR reaction that can be analyzed for edits at the target site. The size of this product will vary based on the nature of the edit. Amplicons can be sequenced directly using an amplicon sequencing approach or ligated to a convenient plasmid vector for Sanger sequencing. Those plants in which the MON87701 5'-junction sequence is disrupted are selected and grown to maturity. The DNA encoding the Cas12a reagents can be segregated away from the modified junction sequence in a subsequent generation.

Example 2. Insertion of a CgRRS Element in the 5'-Junction of the MON87701 Event Two plant gene expression vectors are prepared. Plant expression cassettes for expressing a bacteriophage lambda exonuclease, a bacteriophage lambda beta SSAP protein, and an *E. coli* SSB are constructed essentially as set forth in US Patent Application Publication 20200407754, which is incorporated herein by reference in its entirety. A DNA sequence encoding a tobacco c2 nuclear localization signal (NLS) is fused in-frame to the DNA sequences encoding the exonuclease, the bacteriophage lambda beta SSAP protein, and the *E. coli* SSB to provide a DNA sequence encoding the c2 NLS-Exo, c2 NLS lambda beta SSAP, and c2 NLS-SSB fusion proteins that are set forth in SEQ ID NO: 135, SEQ ID NO: 134, and SEQ ID NO: 133 of US Patent Application Publication 20200407754, respectively, and incorporated herein by reference in their entireties. DNA sequences encoding the c2 NLS-Exo, c2 NLS lambda beta SSAP, and c2NLS-SSB fusion proteins are operably linked to suitable promoter(s) (e.g., AtUbi10, CaMV35S, and/or SlUbi10 promoter) and suitable polyadenylation site(s) (e.g., nos 3', PeaE9 3', tmr 3', tms 3', AtUbi10 3', and tr7 3' elements), to provide the exonuclease, SSAP, and SSB plant expression cassettes.

Figure 5:
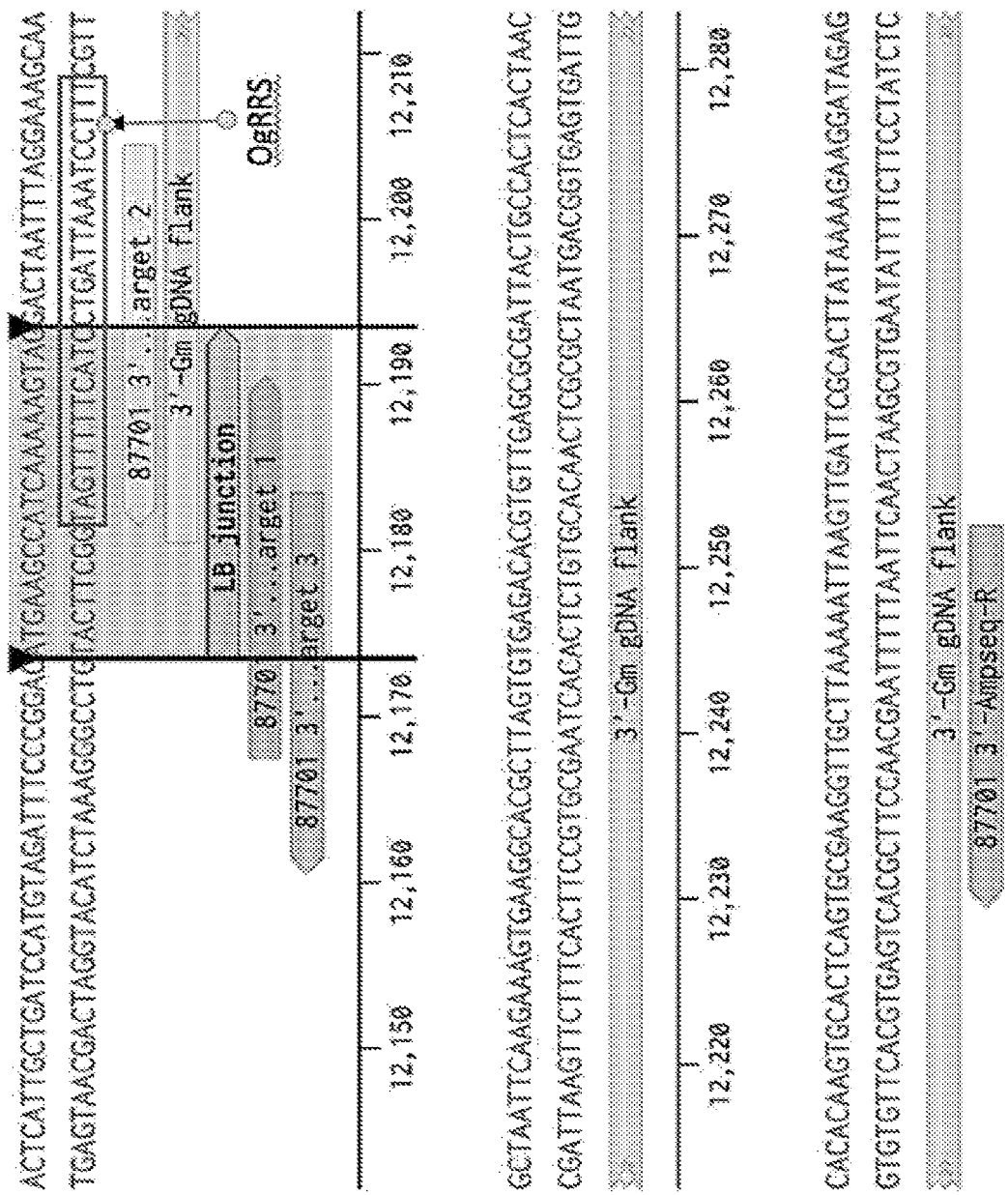
FIG. 5 illustrates the location of the OgRRS of SEQ ID NO: 6 in the 3' junction polynucleotide of SEQ ID NO:1. Sequences in the figure are the corresponding sequences of SEQ ID NO: 1 and their reverse complement.

A DNA donor template sequence (SEQ ID NO: 9 or 21) that targets the 5'-T-DNA junction polynucleotide of the MON87701 event (SEQ ID NO:1) for HDR-mediated insertion of a 27 base pair OgRRS sequence (SEQ ID NO: 6) that is identical to a Cas12a recognition site (i.e., OgRRS) at the 3'-junction polynucleotide of the MON87701 T-DNA insert is constructed. The location of the OgRRS in the 3' junction polynucleotide of SEQ ID NO: 1 is depicted in FIG. 5. The DNA donor sequence includes a replacement template with desired insertion region (27 base pairs long) flanked on both sides by homology arms about 500-635 bp in length. The homology arms match (i.e., are homologous to) gDNA (genomic DNA) regions flanking the target genomic DNA insertion site (SEQ ID NO: 10) in the MON87701 transgenic locus (SEQ ID NO: 1). The replacement template region comprising the donor DNA is flanked at each end by DNA sequences identical to the MON87701 5' junction polynucleotide sequence and contains a CgRRS element recognized by the same Cas12a RNA-guided nuclease and a gRNA (e.g., comprising an RNA encoded by SEQ ID NO: 11) that recognize the OgRRS located in the 3' junction polynucleotide.

A plant expression cassette that provides for expression of the RNA-guided sequence-specific Cas12a endonuclease is constructed. A plant expression cassette that provides for expression of a guide RNA (e.g., encoded by SEQ ID NO: 4 or 5) complementary to sequences adjacent to the insertion site is constructed. An *Agrobacterium* superbinary plasmid transformation vector containing a cassette that provides for the expression of a suitable plant selectable marker (e.g., a neomycin phosphotransferase (nptII) or hygromycin phosphotransferase (hpt)) is constructed. Once the cassettes, donor sequence and *Agrobacterium* superbinary plasmid transformation vector are constructed, they are combined to generate two soybean transformation plasmids. In other embodiments, other gRNAs (Guide-1 or Guide-2) can be used to introduce double stranded breaks in the MON87701 5' junction polynucleotide for insertion of a CgRRS using similar donor DNA templates and the aforementioned Cas12a, SSAP, SSB, and EXO reagents.

A soybean transformation plasmid is constructed with a neomycin phosphotransferase (nptII) or hygromycin phosphotransferase (hpt) cassette, the RNA-guided sequence-specific endonuclease cassette, the guide RNA cassette, and the MON87701 5'-T_DNA junction sequence DNA donor sequence into the *Agrobacterium* superbinary plasmid transformation vector (the control vector).

A soybean transformation plasmid is constructed with a neomycin phosphotransferase (nptII) or hygromycin phosphotransferase (hpt) cassette, the RNA-guided sequence-specific endonuclease cassette, the guide RNA cassette, the SSB cassette, the lambda beta SSAP cassette, the Exo cassette, and the MON87701 5'-T_DNA junction sequence donor DNA template sequence (SEQ ID NO: 9 or 21) into the *Agrobacterium* superbinary plasmid transformation vector (the lambda red vector).

All constructs are transformed into *Agrobacterium* strain LBA4404.

Soybean transformations are performed as described in Example 1 or based on published methods (Ishida et. al, Nature Protocols 2007; 2, 1614-1621). Briefly, immature embryos from inbred line GIBE0104, approximately 1.8-2.2 mm in size, are isolated from surface sterilized ears 10-14 days after pollination. Embryos are placed in an *Agrobacterium* suspension made with infection medium at a concentration of OD 600=1.0. Acetosyringone (200 μM) is added to the infection medium at the time of use. Embryos and *Agrobacterium* are placed on a rocker shaker at slow speed for 15 minutes. Embryos are then poured onto the surface of a plate of co-culture medium. Excess liquid media is removed by tilting the plate and drawing off all liquid with a pipette. Embryos are flipped as necessary to maintain a scutelum up orientation. Co-culture plates are placed in a box with a lid and cultured in the dark at 22° C. for 3 days. Embryos are then transferred to resting medium, maintaining the scutellum up orientation. Embryos remain on resting medium for 7 days at 27-28° C. Embryos that produced callus are transferred to Selection 1 medium with G418 or hygromycin at concentrations permitting selection of transformants when a nptII or hpt selectable marker, respectively, is used and cultured for an additional 7 days. Callused embryos are placed on Selection 2 medium with suitable concentrations of the selection agent for the selectable marker and cultured for 14 days at 27-28° C. Growing calli resistant to the selection agent are transferred to Pre-Regeneration media with suitable concentrations of the selection agent for the selctablew marker to initiate shoot development. Calli remains on Pre-Regeneration media for 7 days. Calli beginning to initiate shoots are transferred to Regeneration medium with G418 or hygromycin at concentrations permitting selection of transformants when a nptII or hpt selectable marker is used in Phytatrays and cultured in light at 27-28° C. Shoots that reached the top of the Phytatray with intact roots are isolated into Shoot Elongation medium prior to transplant into soil and gradual acclimatization to greenhouse conditions.

When a sufficient amount of viable tissue is obtained, it can be screened for insertion at the MON87701 junction sequence, using a PCR-based approach. The PCR primer on the 5'-end can be SEQ ID NO: 12. The PCR primer on the 3'-end can be SEQ ID NO: 13). The above primers that flank donor DNA homology arms are used to amplify the MON87701 5'-junction polynucleotide sequence. The correct donor sequence insertion will produce a PCR product which can be distinguished from PCR products obtained from unedited MON87701 loci. Unique DNA fragments comprising a CgRRS in the MON87701 5' junction polynucleotide are set forth in SEQ ID NO: 7, 8, 9, 14. Amplicons can be sequenced directly using an amplicon sequencing approach or ligated to a convenient plasmid vector for Sanger sequencing. Those plants in which the MON87701 junction sequence now contains the intended Cas12a recognition sequence (e.g., a CgRRS of SEQ ID NO: 7, 8, or 14) are selected and grown to maturity. The T-DNA encoding the Cas12a reagents can be segregated away from the modified junction sequence in a subsequent generation. The resultant INIR20 transgenic locus (SEQ ID NO: 2 or 15) comprising the CgRRS and OgRRS (e.g., which each comprise SEQ ID NO: 6) can be excised using Cas12a and a suitable gRNA which hybridizes to DNA comprising SEQ ID NO: 11 at both the OgRRS and the CgRRS.

The breadth and scope of the present disclosure should not be limited by any of the above-described embodiments.

What is claimed is:

1. A transgenic soybean plant cell comprising an INIR20 transgenic locus comprising a DNA molecule having at least 95% sequence identity across the entire length of SEQ ID NO: 3, wherein the INIR20 transgenic locus comprises an originator guide RNA recognition site (OgRRS) and a cognate guide RNA recognition site (CgRRS), and wherein said CgRRS comprises the DNA molecule set forth in SEQ ID NO: 8.

2. The transgenic soybean plant cell of claim 1, wherein said INIR20 transgenic locus comprises the DNA molecule set forth in SEQ ID NO: 3.

3. A transgenic soybean plant part comprising the soybean plant cell of claim 1.

4. The transgenic soybean plant part of claim 3, wherein said soybean plant part is a seed.

5. A transgenic soybean plant comprising the soybean plant cell of claim 1.

6. A method for obtaining a bulked population of inbred seed comprising selfing the transgenic soybean plant of claim 5 and harvesting seed comprising the INIR20 transgenic locus from the selfed soybean plant.

7. A method of obtaining hybrid soybean seed comprising crossing the transgenic soybean plant of claim 5 to a second soybean plant which is genetically distinct from the first soybean plant and harvesting seed comprising the INIR20 transgenic locus from the cross.

8. A DNA molecule comprising SEQ ID NO: 3.

9. A processed transgenic soybean plant product comprising the DNA molecule of claim 8.

10. A biological sample containing the DNA molecule of claim 8.

11. A method of detecting a soybean plant cell comprising the INIR20 transgenic locus of claim 1, comprising the step of detecting a DNA molecule comprising SEQ ID NO: 8.

12. A method of excising the INIR20 transgenic locus from the genome of the soybean plant cell of claim 1, comprising the steps of:
- (a) contacting the genome of the soybean plant cell with:
  - (i) an RNA dependent DNA endonuclease (RdDe); and
  - (ii) a guide RNA (gRNA) capable of hybridizing to the guide RNA hybridization site of the OgRRS and the CgRRS of SEQ ID NO: 3; wherein the RdDe recognizes a OgRRS/gRNA and a CgRRS/gRNA hybridization complex; and,
- (b) selecting a plant cell, plant part, or plant wherein the INIR20 transgenic locus flanked by the OgRRS and the CgRRS has been excised.

13. The method of claim 12, wherein the guide RNA comprises an RNA sequence encoded by SEQ ID NO: 11.

* * * * *